US012648833B2

(12) United States Patent
Inglese et al.

(10) Patent No.: US 12,648,833 B2
(45) Date of Patent: Jun. 9, 2026

(54) RECONSTRUCTION OF A VIRTUAL COMPUTED-TOMOGRAPHY VOLUME TO TRACK ORTHODONTICS TREATMENT EVOLUTION

(71) Applicant: Carestream Dental Technology Topco Limited, London (GB)

(72) Inventors: Jean-Marc Inglese, Bussy-Saint-Georges (FR); Shoupu Chen, Rochester, NY (US); Chuanmao Fan, Rochester, NY (US); Jacques Faure, Courbevoie (FR); Sebastien Henry, Croissy-Beaubourg (FR); Sabrina Capron-Richard, Noisiel (FR); Delphine Reynard, Montreuil (FR); Xavier Ripoche, Mandres les Roses (FR); Jacques Treil, Toulouse (FR); Victor C. Wong, Pittsford, NY (US)

( * ) Notice: Subject to any disclaimer, the term of this patent is extended or adjusted under 35 U.S.C. 154(b) by 570 days.

(21) Appl. No.: 17/989,749

(22) Filed: Nov. 18, 2022

(65) Prior Publication Data

US 2023/0320818 A1     Oct. 12, 2023

Related U.S. Application Data

(62) Division of application No. 16/475,253, filed as application No. PCT/GB2017/053894 on Dec. 27, 2017, now Pat. No. 11,638,626.

(Continued)

(51) Int. Cl.
| | |
|---|---|
| *G06K 9/00* | (2022.01) |
| *A61B 6/00* | (2006.01) |
| *A61B 6/03* | (2006.01) |
| *A61B 6/46* | (2024.01) |
| *A61B 6/51* | (2024.01) |

(Continued)

(52) U.S. Cl.
CPC ................ *A61C 7/002* (2013.01); *A61B 6/03* (2013.01); *A61B 6/463* (2013.01); *A61B 6/51* (2024.01); *A61B 6/5217* (2013.01); *A61B 6/5247* (2013.01); *G06T 7/0012* (2013.01);
(Continued)

(58) Field of Classification Search
None
See application file for complete search history.

(56) References Cited

U.S. PATENT DOCUMENTS

| | | | | |
|---|---|---|---|---|
| 2014/0314291 A1* | 10/2014 | Souza | ................... | G06T 7/0012 |
| | | | | 382/131 |
| 2014/0348405 A1* | 11/2014 | Chen | ..................... | A61C 7/002 |
| | | | | 382/131 |

* cited by examiner

*Primary Examiner* — Wei Wen Yang

(57) ABSTRACT

Method and/or apparatus embodiments for 3-D cephalometric analysis of a patient according to the application can display reconstructed volume image data from a computed tomographic scan of a patient's head including segmented dentition elements having an initial arrangement from one or more 2D/3D views; can compute and display a plurality of cephalometric parameters for the patient according to the reconstructed volume image data; then use the patient specific cephalometric parameters and population biometry data, to identify one or more maxillofacial/dental abnormalities; and compose patient specific treatment plans to correct selected dentition abnormalities using maxillofacial/dental structure, which can be composed in a final tooth arrangement in a final virtual CT volume. One or more aligners can be generated to incrementally move dentition from the initial arrangement to the final tooth arrangement.

12 Claims, 66 Drawing Sheets

Related U.S. Application Data

(60) Provisional application No. 62/575,006, filed on Oct. 20, 2017, provisional application No. 62/539,577, filed on Aug. 1, 2017, provisional application No. 62/440,435, filed on Dec. 30, 2016.

(51) Int. Cl.
    *A61C 7/00*        (2006.01)
    *G06T 7/00*        (2017.01)
    *G06T 12/30*      (2026.01)

(52) U.S. Cl.
    CPC .... *G06T 12/30* (2026.01); *G06T 2207/10081* (2013.01); *G06T 2207/30036* (2013.01)

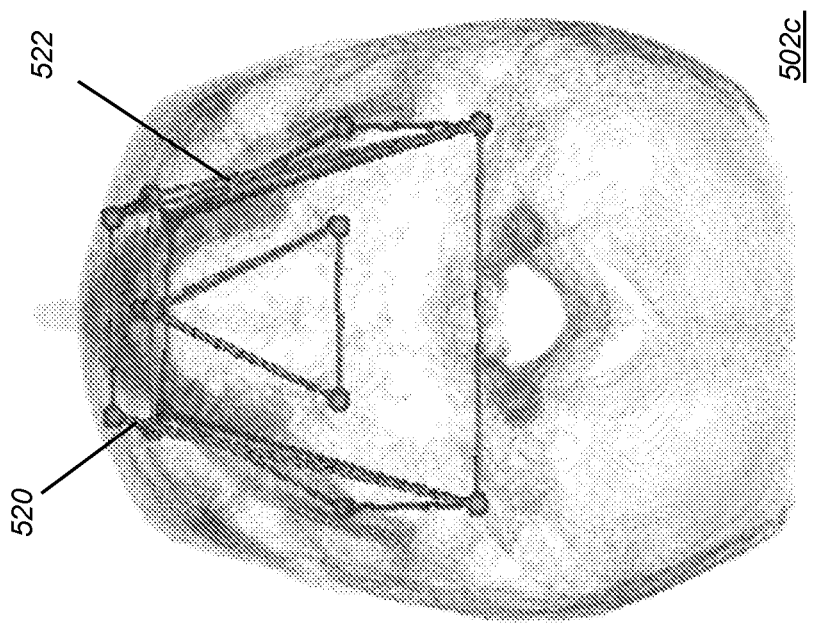
*FIG. 7C*
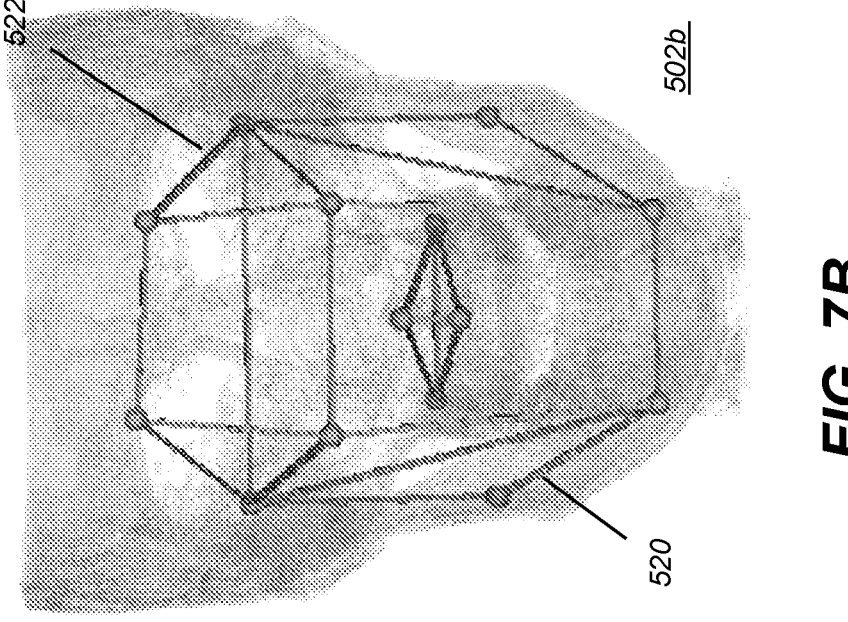
*FIG. 7B*

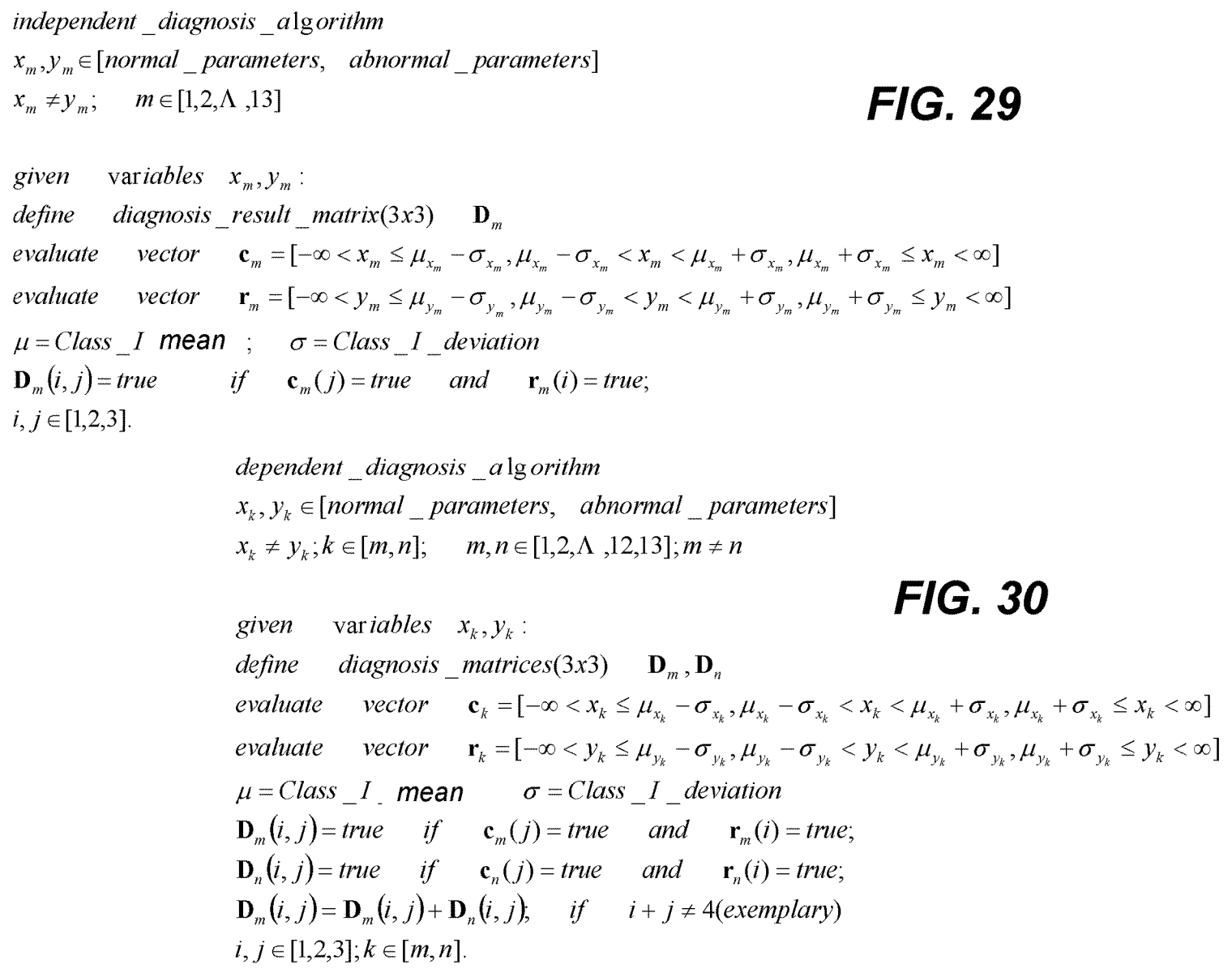

*independent_diagnosis_algorithm*

$x_m, y_m \in [normal\_parameters, \ abnormal\_parameters]$ $x_m \neq y_m; \quad m \in [1, 2, \Lambda, 13]$

*given    variables* $x_m, y_m$:

*define    diagnosis_result_matrix*(3x3)    $\mathbf{D}_m$

*evaluate    vector*    $\mathbf{c}_m = [-\infty < x_m \leq \mu_{x_m} - \sigma_{x_m}, \mu_{x_m} - \sigma_{x_m} < x_m < \mu_{x_m} + \sigma_{x_m}, \mu_{x_m} + \sigma_{x_m} \leq x_m < \infty]$

*evaluate    vector*    $\mathbf{r}_m = [-\infty < y_m \leq \mu_{y_m} - \sigma_{y_m}, \mu_{y_m} - \sigma_{y_m} < y_m < \mu_{y_m} + \sigma_{y_m}, \mu_{y_m} + \sigma_{y_m} \leq y_m < \infty]$ $\mu = Class\_1 \ mean$ ;    $\sigma = Class\_1\_deviation$ $\mathbf{D}_m(i, j) = true$    *if*    $\mathbf{c}_m(j) = true$    *and*    $\mathbf{r}_m(i) = true;$ $i, j \in [1, 2, 3]$.

FIG. 30

*dependent_diagnosis_algorithm*

$x_k, y_k \in [normal\_parameters, \ abnormal\_parameters]$ $x_k, y_k; k \in [m, n]; \quad m, n \in [1, 2, \Lambda, 12, 13]; m \neq n$ $x_k \neq y_k; k \in [m, n]$

*given    variables*    $x_k, y_k$:

*define    diagnosis_matrices*(3x3)    $\mathbf{D}_m, \mathbf{D}_n$

*evaluate    vector*    $\mathbf{c}_k = [-\infty < x_k \leq \mu_{x_k} - \sigma_{x_k}, \mu_{x_k} - \sigma_{x_k} < x_k < \mu_{x_k} + \sigma_{x_k}, \mu_{x_k} + \sigma_{x_k} \leq x_k < \infty]$

*evaluate    vector*    $\mathbf{r}_k = [-\infty < y_k \leq \mu_{y_k} - \sigma_{y_k}, \mu_{y_k} - \sigma_{y_k} < y_k < \mu_{y_k} + \sigma_{y_k}, \mu_{y_k} + \sigma_{y_k} \leq y_k < \infty]$ $\mu = Class\_1\_mean$        $\sigma = Class\_1\_deviation$ $\mathbf{D}_m(i, j) = true$    *if*    $\mathbf{c}_m(j) = true$    *and*    $\mathbf{r}_m(i) = true;$ $\mathbf{D}_n(i, j) = true$    *if*    $\mathbf{c}_n(j) = true$    *and*    $\mathbf{r}_n(i) = true;$ $\mathbf{D}_m(i, j) = \mathbf{D}_m(i, j) + \mathbf{D}_n(i, j),$    *if*    $i + j \neq 4(exemplary)$ $i, j \in [1, 2, 3]; k \in [m, n]$.

| 1 | Case name : CII III9 | | |
|---|---|---|---|
| 2 | Eighteen Parameters | | |
| 3 | Antero-posterior | | |
| 4 | alveolar~GIM-Gim | -10.479 | Overjet, GIMx-Gimx, centers of inertia of upper and lower incisors |
| 5 | alveolar~GM-Gm | -8.899 | Dental class II, Gmy-Gmy |
| 6 | alveolar~TqIM | 37.0168 | Angular maxillar incisors protrusion (torque), medium upper incisors torque |
| 7 | alveolar~Tqim | 11.2776 | Angular mandibular incisors protrusion (torque), medium lower incisors torque |
| 8 | alveolar~GIM-Gim/2 or Giy | 23.0233 | Linear biprotrusion, (GIMy+Gimy)/2 |
| 9 | basis~MNP-MM | -10.028 | Basic class II, MNPy-MMy |
| 10 | basis~MFM-MM | 58.0601 | Corpus length, this is the real length between MFM and MM |
| 11 | architecture~MMy | 19.0165 | Chin protrusion, y coordinate of medium mental |
| 12 | architecture~MHM-MM | 106.922 | Mandibular global length, this is the real length getween MHM and MM |
| 13 | Vertical | | |
| 14 | alveolar~Gdz | 37.0501 | arches altitude, z coordinate of the inertia center of all teeth |
| 15 | alveolar~MxII-MdII | -6.8922 | Inter-arches divergence, MxII/V2(SP) |
| 16 | basis~<MHM-MIO, MFM-MM> | 27.609 | Pseudo FMA (orbital floor/corpus angle) |
| 17 | architecture~MMz | 61.97 | Maxillo-mandibular height |
| 18 | architecture~13 | 35.4216 | Facial global divergence, angle between MHM-MIO axis and MHM-MM axis |
| 19 | Transverse | | |
| 20 | alveolar~dM-dm | -0.4271 | Inter-first molars diameter relationship |
| 21 | alveolar~TqM-Tqm | 27.5746 | Class III or mandibular excess angular compensation |
| 22 | basis~RGP-LGP/RFM-LFM | 36.2319 | Basis maxillar/mandibular excess, LGPx-RGPx/LFMx-RFMx |
| 23 | architecture~RIO-LIO/RM-LM | 115.909 | Infra-orbital (anterior mandibular width, formula RIOx-LIOx/RMx-LMx) |
| 24 | Deduced | | |
| 25 | hidden~GIM | 17.7837 | Upper incisors group protrusion |
| 26 | hidden~GiM | 28.2629 | Lower incisors group protrusion |
| 27 | hidden~(TqIM+Tqim)/2 | 24.1472 | Medium upper and lower incisors torque |
| 28 | hidden~(TqIM+Tqim) | 25.7392 | Upper and lower incisors torque difference |
| 29 | hidden~MNPy | 8.98866 | Maxilla protrusion |
| 30 | hidden~GIM-MNP(y) | 8.79502 | Upper linear class III compensation |
| 31 | hidden~GiM-MM(y) | 9.24639 | Upper linear class II compensation |
| 32 | hidden~Gdz/(MMz~Gdz) | 0.44603 | Maxi/mandi ratio of maxi mandi global height |

| Index | measure | Comment | Norm | mean | std | -S | +S | -Ss | +Ss |
|---|---|---|---|---|---|---|---|---|---|
| | m/dec | | am/deqm | deqm | deqm | deqm | deqm | deqm | degr |
| Anterior-posterior | | | | | | | | | |
| 1 abrodar.AP.RL.G16y-G26y | -0.11 | AP 16/26 difference (T16) | 0 | -0.05 | 1.22 | 1.32 | 1.22 | 1.29 | 1.19 |
| 2 alveolar.misGap~G46y-G36y | 0.34 | AP 46/36 difference (T16) | 0 | 0.12 | 1.32 | -1.2 | 1.44 | -1.17 | 1.4 |
| 3 ak.AP.mar~(G16y-G36y)-(RSPy-LGPy) | -0.5 | Upper molar AP position/maxilla right/left difference | 0 | -0.37 | 1.49 | 1.86 | 1.12 | 1.81 | 1.09 |
| 4 alv.cmp.shiftmg~(G46-G36)y-(RFM-LFM)y | 0.93 | Lower molar AP position/mandible right/left difference | 0 | -0.05 | 2.26 | -2.31 | 2.21 | -2.26 | 2.16 |
| 5 alveolar.AP.CII.R~G16y-G46y | 1.5 | Right Class II, negative value means Class III relationship (T17) | 3.09 | -3.09 | 1.55 | -4.63 | 1.54 | -4.53 | -1.5 |
| 6 alveolar.AP.CII_L~G26y-G36y | 2 | Left Class II; negative value means Class II relationship (T17) | -2.92 | -2.92 | 1.21 | -4.13 | -1.71 | -4.03 | -1.67 |
| 7 bass.RL.(RM-RFM)-(LM-LFM) | -0.48 | Horizontal branches right/left difference projected on X (T19) | 0 | -0.93 | 3.24 | 3.10 | 1.31 | 3.09 | 1.28 |
| 8 bass.morpho~RGPy-LGPy | 0.38 | AP great palatal right/left position difference (T18) | 0 | 0.32 | 1.34 | -1.02 | 1.66 | -0.99 | 1.62 |
| 9 bass.diff~RFMy-LFMy | -0.59 | AP mandible foramen right/left position difference (T18) | 0 | 0.17 | 2.55 | -2.38 | 2.72 | -2.32 | 2.66 |
| 10 arch.AP.RL.FcExcss~(RIO-RHM)-(LIO-LHM) | -0.33 | Facial depth right/left difference (IFO level) | 0 | -0.09 | 2.95 | -3.05 | 2.86 | -2.98 | 2.79 |
| 11 arch.AP.RL.FcExcss~(RSO-RHM)-(LSO-LHM) | 0.22 | Facial depth right/left difference (SPO level) | 0 | 0.22 | 2.22 | -2 | 2.44 | -1.86 | 2.38 |
| 12 arch.AP.RL.FcExcss~RSOy-LSOy | 0.55 | AP SPO positions, right/left difference | 0 | 0.31 | 1.46 | -1.15 | 1.77 | -1.12 | 1.73 |
| 13 arch.AP.RL.FcExcss~RMy-LMy | -1.07 | AP mental positions, right/left difference (T19) | 0 | -0.76 | 1.7 | -2.46 | 0.93 | -2.4 | 0.93 |
| 14 arch.AP.RL.FcExcss~(RM-RHM)-(LM-LHM) | -1.4 | Facial depth right/left difference (mental level) projected on Y | 0 | -0.85 | 2.63 | -3.48 | 1.78 | -3.39 | 1.74 |
| 15 arch.AP.RL.FcExcss~(RHM,RIO,RM)-(LHM,LIO,LM) | -1.29 | Mandible global opening right/left difference | 0 | 0.3 | 3.06 | -2.77 | 3.36 | -2.77 | 3.36 |
| 16 addmbn.AP.RL~(G16y-G46y)-(G26y-G36y) | -0.45 | Class 2 right/left difference | 0 | -0.17 | 0.81 | -0.98 | 0.64 | -0.95 | 0.63 |

*FIG. 31C*

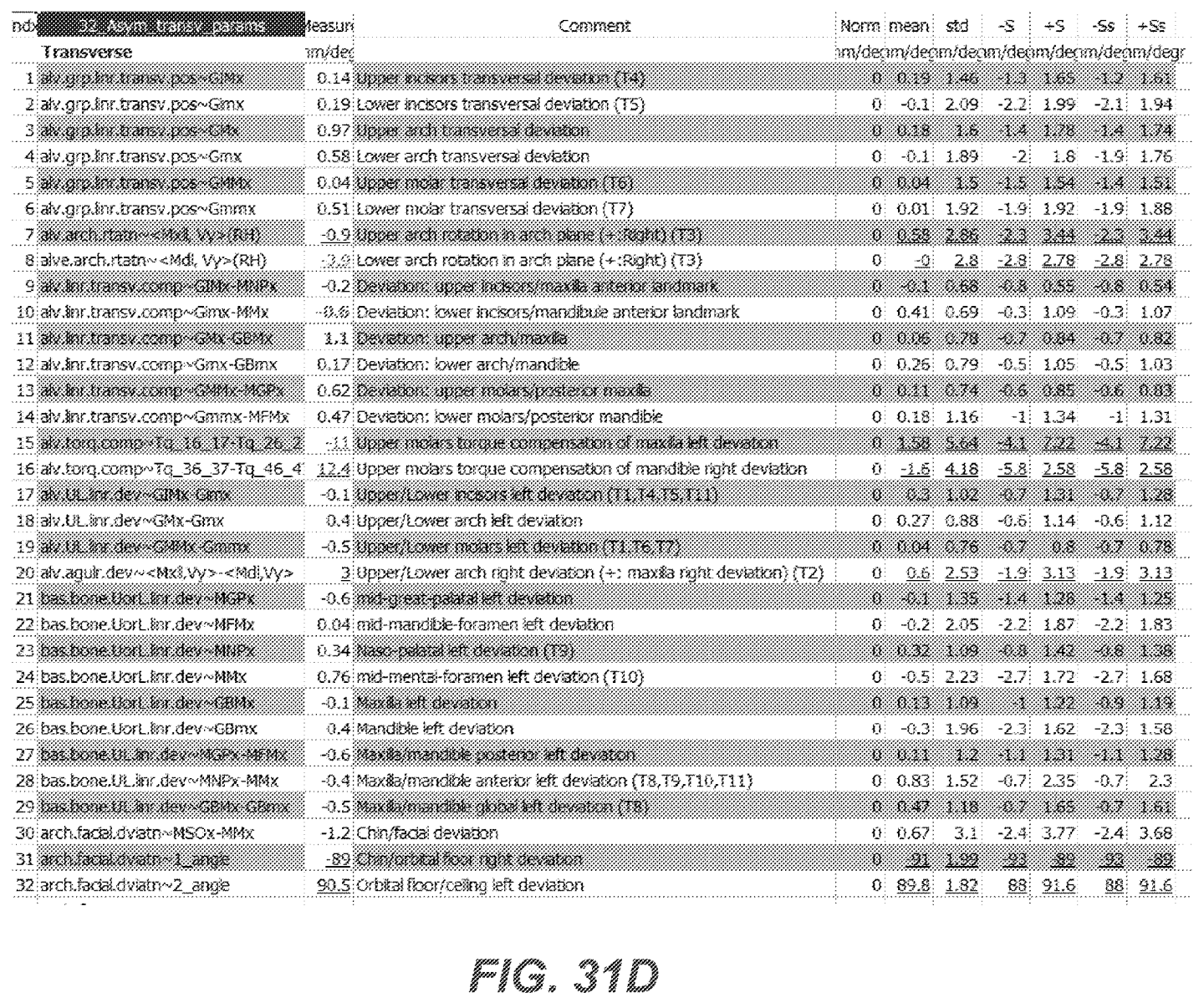

| ndx | Measure | m/deg | Comment | Norm | mean | std | -S | +S | -Ss | +Ss |
|---|---|---|---|---|---|---|---|---|---|---|
| | | m/deg | | m/deg | m/deg | m/deg | m/deg | m/deg | m/deg | m/degr |
| | Transverse | | | | | | | | | |
| 1 | av.grp.inr.transv.pos~Gmx | 0.14 | Upper incisors transversal deviation (T4) | 0 | 0.13 | 1.46 | -1.3 | 1.65 | -1.2 | 1.81 |
| 2 | av.grp.inr.transv.pos~Gmx | 0.19 | Lower incisors transversal deviation (T5) | 0 | -0.1 | 2.09 | -2.2 | 1.99 | -2.1 | 1.94 |
| 3 | av.grp.inr.transv.pos~Gmx | 0.97 | Upper arch transversal deviation | 0 | 0.18 | 1.6 | -1.4 | 1.78 | -1.4 | 1.74 |
| 4 | av.grp.inr.transv.pos~Gmx | 0.58 | Lower arch transversal deviation | 0 | -0.1 | 1.89 | -2 | 1.8 | -1.9 | 1.76 |
| 5 | av.grp.inr.transv.pos~GMx | 0.04 | Upper molar transversal deviation (T6) | 0 | 0.04 | 1.5 | -1.3 | 1.54 | -1.4 | 1.51 |
| 6 | av.grp.inr.transv.pos~Gmmx | 0.51 | Lower molar transversal deviation (T7) | 0 | 0.01 | 1.92 | -1.9 | 1.92 | -1.9 | 1.88 |
| 7 | av.arch.tatn~<Mdl.Vy>(RH) | -0.9 | Upper arch rotation in arch plane (+:Right) (T3) | 0 | 0.53 | 2.86 | -2.3 | 3.44 | -2.2 | 3.44 |
| 8 | av.arch.tatn~<Mdl.Vy>(RH) | -3.4 | Lower arch rotation in arch plane (+:Right) (T3) | 0 | -0 | 2.8 | -2.8 | 2.78 | -2.8 | 2.78 |
| 9 | av.inr.transv.comp~GMx-MMPx | -0.2 | Deviation: upper incisors/maxilla anterior landmark | 0 | 0.06 | 0.66 | -0.6 | 0.55 | -0.6 | 0.54 |
| 10 | av.inr.transv.comp~Gmx-MMx | -3.6 | Deviation: lower incisors/mandible anterior landmark | 0 | 0.41 | 0.69 | -0.3 | 1.09 | -0.3 | 1.07 |
| 11 | av.inr.transv.comp~GMx-GBMx | 1.1 | Deviation: upper arch/maxilla | 0 | 0.06 | 0.78 | -0.7 | 0.84 | -0.7 | 0.82 |
| 12 | av.inr.transv.comp~Gmx-GBmx | 0.17 | Deviation: lower arch/mandible | 0 | 0.26 | 0.79 | -0.5 | 1.05 | -0.5 | 1.03 |
| 13 | av.inr.transv.comp~GMx-MGPx | 0.62 | Deviation: upper molars/posterior maxilla | 0 | 0.11 | 0.74 | -0.6 | 0.85 | -0.6 | 0.83 |
| 14 | av.inr.transv.comp~Gmmx-MFMx | 0.47 | Deviation: lower molars/posterior mandible | 0 | 0.18 | 1.16 | -1 | 1.34 | -1 | 1.31 |
| 15 | av.torq.comp~Tg_36_37-Tg_46_4 | -1.1 | Upper molars torque compensation of mandible left deviation | 0 | 1.58 | 5.64 | -4.1 | 2.22 | -4.1 | 2.22 |
| 16 | av.torq.comp~Tg_36_37-Tg_46_4 | 12.4 | Upper molars torque compensation of mandible right deviation | 0 | -1.6 | 4.18 | -5.8 | 2.58 | -5.8 | 2.58 |
| 17 | av.UL.inr.dev~GMx-Gmx | -0.1 | Upper/Lower incisors left deviation (T1,T4,T5,T11) | 0 | 0.3 | 1.02 | -0.7 | 1.31 | -0.7 | 1.28 |
| 18 | av.UL.inr.dev~GMx-Gmx | 0.4 | Upper/Lower arch left deviation | 0 | 0.27 | 0.88 | -0.6 | 1.14 | -0.6 | 1.12 |
| 19 | av.UL.inr.dev~GMx-Gmmx | -0.5 | Upper/Lower molars left deviation (T1,T6,T7) | 0 | 0.04 | 0.76 | -0.7 | 0.8 | -0.7 | 0.78 |
| 20 | av.agul.dev~<Ntxl.Vy>-<Mdl.Vy> | 3 | Upper/Lower arch right deviation (+: maxilla right deviation) (T2) | 0 | 0.6 | 2.53 | -1.9 | 3.13 | -1.9 | 3.13 |
| 21 | bas.bone.Uorl.lnr.dev~MGPx | -0.6 | mid-great-palatal left deviation | 0 | -1.1 | 1.35 | -1.4 | 1.26 | -1.4 | 1.26 |
| 22 | bas.bone.Uorl.lnr.dev~MFMx | 0.04 | mid-mandible-foramen left deviation | 0 | -0.2 | 2.05 | -2.2 | 1.87 | -2.2 | 1.83 |
| 23 | bas.bone.Uorl.lnr.dev~MMPx | 0.34 | Maxilla/mandible posterior left deviation (T9) | 0 | 0.32 | 1.09 | -0.8 | 1.43 | -0.8 | 1.38 |
| 24 | bas.bone.Uorl.lnr.dev~MMx | 0.76 | mid-menta-foramen left deviation (T10) | 0 | -0.5 | 2.23 | -2.7 | 1.72 | -2.7 | 1.68 |
| 25 | bas.bone.Uorl.lnr.dev~GBMx | -0.1 | Maxilla left deviation | 0 | 0.13 | 1.03 | -1 | 1.22 | -0.9 | 1.19 |
| 26 | bas.bone.Uorl.lnr.dev~GBmx | 0.4 | Mandible left deviation | 0 | -0.3 | 1.96 | -2.3 | 1.62 | -2.3 | 1.58 |
| 27 | bas.bone.UL.lnr.dev~MGPx-MFMx | -0.6 | Maxilla/mandible posterior left deviation | 0 | 0.11 | 1.2 | -1.1 | 1.31 | -1.1 | 1.28 |
| 28 | bas.bone.UL.lnr.dev~MMPx-MMx | -0.4 | Maxilla/mandible anterior left deviation (T8,T9,T10,T11) | 0 | 0.83 | 1.52 | -0.7 | 2.35 | -0.7 | 2.3 |
| 29 | bas.bone.UL.lnr.dev~GBMx-GBmx | -0.5 | Maxilla/mandible global left deviation (T8) | 0 | 0.47 | 1.18 | -0.7 | 1.65 | -0.7 | 1.61 |
| 30 | arch.facial.dvatn~MSOx-MMx | -1.2 | Chin/facial deviation | 0 | 0.67 | 3.1 | -2.4 | 3.77 | -2.4 | 3.68 |
| 31 | arch.facial.dvatn~1_angle | -.89 | Orbital floor right deviation | 0 | .21 | 1.09 | .2 | .93 | .2 | .92 |
| 32 | arch.facial.dvatn~2_angle | 90.5 | Orbital floor/ceiling left deviation | 0 | 89.8 | 1.82 | 88 | 91.6 | 88 | 91.6 |

*FIG. 31D*

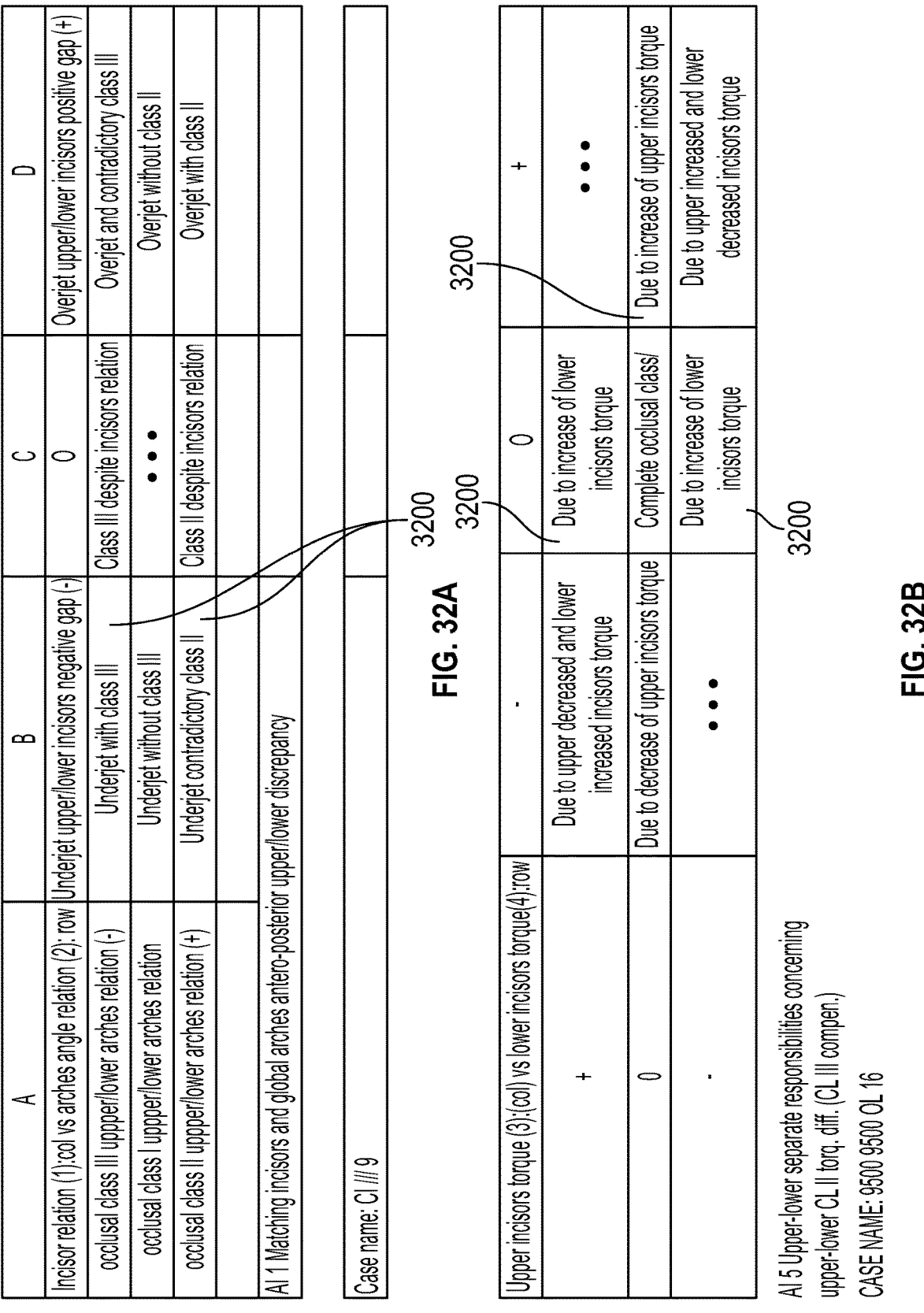

| | A | B | C | D |
|---|---|---|---|---|
| Incisor relation (1):col vs arches angle relation (2): row | | Underjet upper/lower incisors negative gap (-) | O | Overjet upper/lower incisors positive gap (+) |
| occlusal class III uppper/lower arches relation (-) | | Underjet with class III | Class III despite incisors relation | Overjet and contradictory class III |
| occlusal class I uppper/lower arches relation | | Underjet without class III | ... | Overjet without class II |
| occlusal class II uppper/lower arches relation (+) | | Underjet contradictory class II | Class II despite incisors relation | Overjet with class II |
| AI 1 Matching incisors and global arches antero-posterior upper/lower discrepancy | | | | |

Case name: Cl /// 9

| Upper incisors torque (3):(col) vs lower incisors torque(4):row | | - | O | + |
|---|---|---|---|---|
| + | | Due to upper decreased and lower increased incisors torque | Due to increase of lower incisors torque | ... |
| 0 | | Due to decrease of upper incisors torque | Complete occlusal class/ | Due to increase of upper incisors torque |
| - | | ... | Due to increase of lower incisors torque | Due to upper increased and lower decreased incisors torque |

AI 5 Upper-lower separate responsibilities concerning
upper-lower CL II torq. diff. (CL III compen.)
CASE NAME: 9500 9500 OL 16

Figures 32C, 32E:
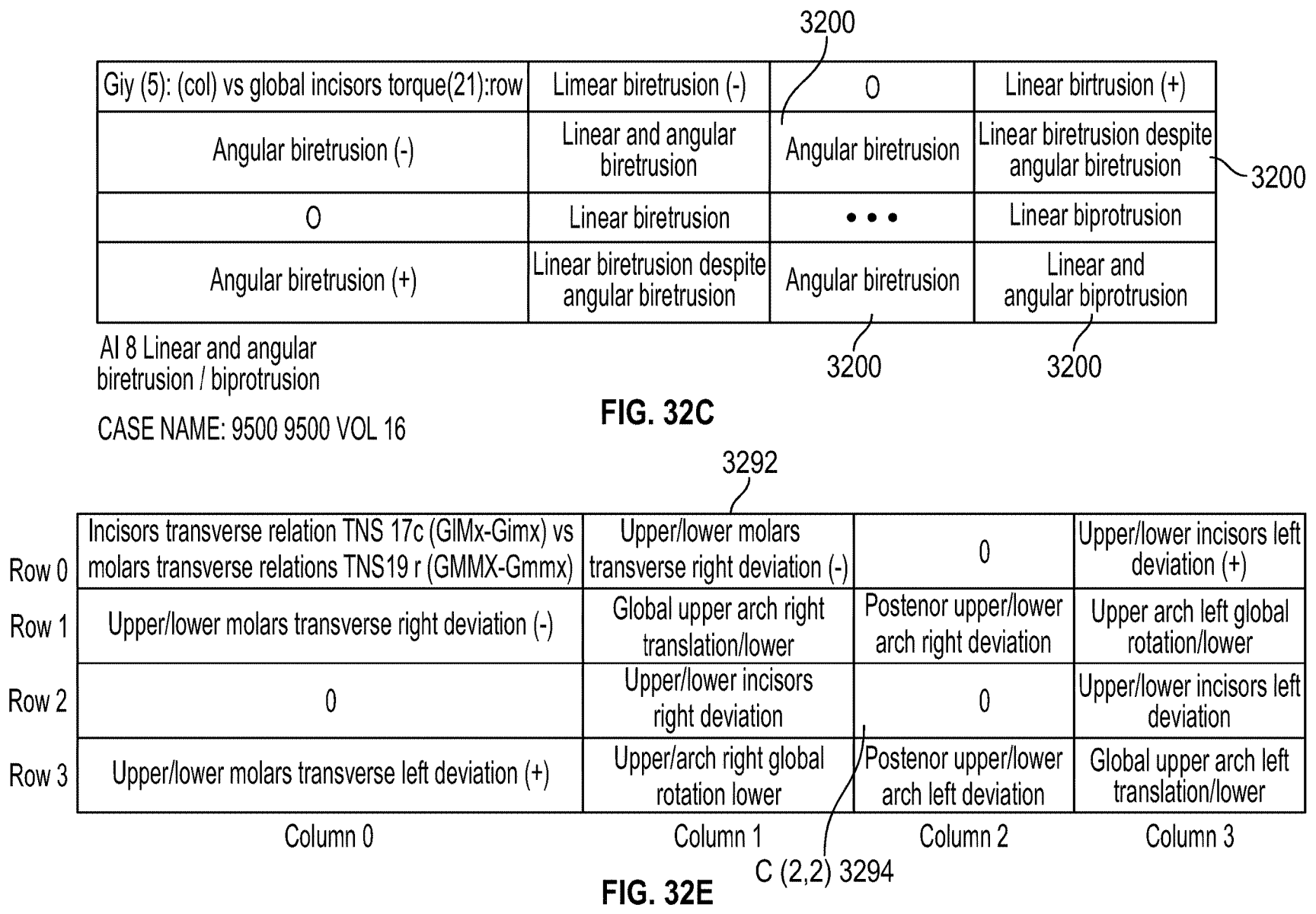

| Giy (5) : (col) vs global incisors torque(21):row | Linear biretrusion (-) | 0 | Linear birtrusion (+) |
|---|---|---|---|
| Angular biretrusion (-) | Linear and angular biretrusion | Angular biretrusion | Linear biretrusion despite angular biretrusion |
| 0 | Linear biretrusion | ... | Linear biprotrusion |
| Angular biretrusion (+) | Linear biretrusion despite angular biretrusion | Angular biretrusion | Linear and angular biprotrusion |

3200

AI 8 Linear and angular biretrusion / biprotrusion

CASE NAME: 9500 9500 VOL 16

| | Incisors transverse relation TNS 17c (GIMx-Gimx) vs molars transverse relations TNS19 r (GMMX-Gmmx) | Upper/lower molars transverse right deviation (-) | 0 | Upper/lower incisors left deviation (+) |
|---|---|---|---|---|
| Row 0 | | | | |
| Row 1 | Upper/lower molars transverse right deviation (-) | Global upper arch right translation/lower | Posterior upper/lower arch right deviation | Upper arch left global rotation/lower |
| Row 2 | 0 | Upper/lower incisors right deviation | 0 | Upper/lower incisors left deviation |
| Row 3 | Upper/lower molars transverse left deviation (+) | Upper/arch right global rotation lower | Posterior upper/lower arch left deviation | Global upper arch left translation/lower |
| | Column 0 | Column 1 | Column 2 | Column 3 |

CASE NAME: 9500 9500 VOL 16

3200

| AI | | PARAMETERS | DIAGOSIS |
|---|---|---|---|
| AI 1 | MATCHING INCISORS AND GLOBAL ARCHES ANTERO-POSTERIOR UPPER LOWER DISCREPANCY | INCISORS RELATION (1):COL VS ARCHES ANGLE RELATION (2): ROW | UNDERJET WITHOUT CLASS III |
| AI 2 | MATCHING INCISORS DISCREPANCY AND SEPARATE LINEAR UPPER (AND LOWER) INCISORS POSITIONS | INCISORS RELATION (1):COL VS UPPER INCISOR POSITION (19): ROW | UNDERJET BY UPPER INCISOR RETRUSION |
| AI 3 | MATCHING INCISORS DISCREPANCY AND SEPARATE LINEAR (UPPER AND) LOWER INCISORS POSITIONS | INCISORS RELATION (1):COL VS LOWER INCISOR POSITION (20): ROW | 0 |
| AI 4 | MATCHING INCISORS GAP & UPPER-LOWER CL II TORQUE DIFFERENTIAL (CL III COMPENSATION) | INCISORS RELATION (1):COL VS TORQUE UPPER/LOWER DIFFERENCE (22): ROW | 0 |
| AI 5 | UPPER-LOWER SEPARATE RESPONSIBILITIES CONCERNING UPPER-LOWER CL II TORQUE DIFFERENTIAL (CLIII COMPEN.) | INCISORS RELATION (1):(COL) VS LOWER INCISOR TORQUE (4): ROW | ... |
| AI 6 | MATCHING ALVEOLAR AND BASIC UPPER/LOWER RELATIONSHIP | DENTAL CLASS II (2): (COL) VS BASIC CLASS II (6): ROW | OCCLUSAL CLASS /DESPITE BASIC CLASS III |
| AI 7 | UPPER/LOWER SEPARATE RESPONSIBILITIES CONCERNING SKELETTAL CL II AND CL III | MNPY (23): (COL) VS MMY (8): ROW | ... |
| AI 8 | LINEAR AND ANGULAR BIRETRUSION/BIPROTRUSION | GIY (5): (COL) VS GLOBAL INCISORS TORQUE (21): ROW | LONG FACE SYNDROM (LINEAR) |
| AI 9 | GLOBAL LINEAR FACIAL VERTICAL HEIGHT AND ITS DISTRIBUTION | MMZ (10):(COL) VS GDZ (MMZ-GDXIZ) (26): ROW | DUE TO MANDIBLE EXCESS |
| AI 10 | LINEAR AND ANGULAR FACIAL DISHARMONY | MMZ (10): (COL) VS 13 (14): ROW | BASIC HYPERDIVERGENCE IN AGREEMENTWITH |
| AI 11 | ALVEOLAR AND BASI DIVERGENCES | MX//-MD// (11): (COL) VS FMA (12): ROW | FACIAL HYPERDIVERGENCE |
| AI 12 | TRANSVERSE LINEAR AND ANGULAR UPPER/LOWER ALVEOLAR RELATIONSHIP | DM-DM (15): (COL) VS TQM-TQM (16): ROW | ... |
| AI 13 | TRANSVERSE LINEAR AND ANGULAR UPPER/LOWER BASIC RELATIONSHIP | RGP-LGP/RFM-LFM (17): (COL) VS RIO-LIO/RM-LM (18): ROW | MIXILLA BASIC EXCESS AND MENTAL DEFICIT |

FIG. 32D

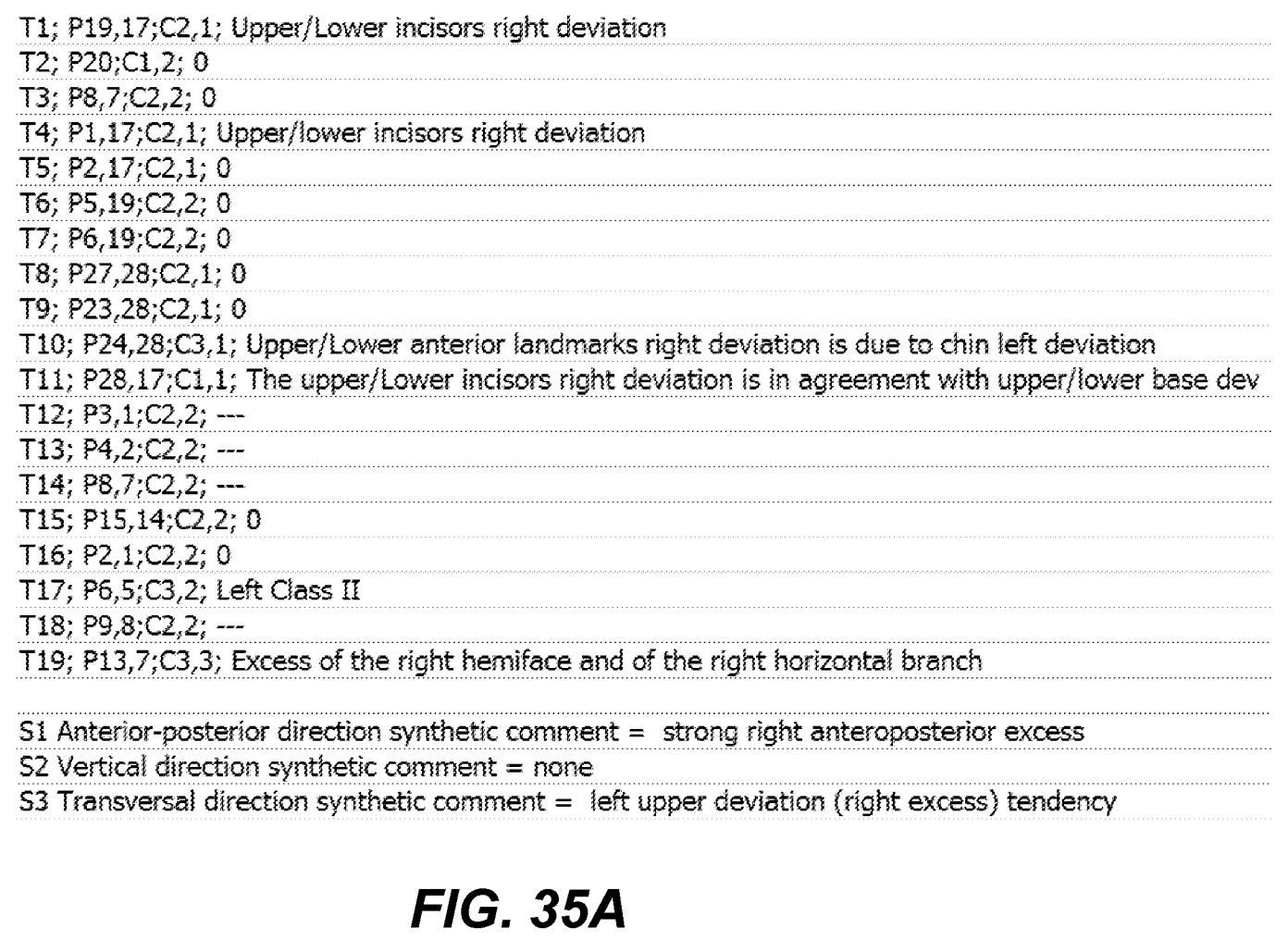

T1; P19,17;C2,1; Upper/Lower incisors right deviation

T2; P20;C1,2; 0

T3; P8,7;C2,2; 0

T4; P1,17;C2,1; Upper/lower incisors right deviation

T5; P2,17;C2,1; 0

T6; P5,19;C2,2; 0

T7; P6,19;C2,2; 0

T8; P27,28;C2,1; 0

T9; P23,28;C2,1; 0

T10; P24,28;C3,1; Upper/Lower anterior landmarks right deviation is due to chin left deviation T11; P28,17;C1,1; The upper/Lower incisors right deviation is in agreement with upper/lower base dev

T12; P3,1;C2,2; —

T13; P4,2;C2,2; —

T14; P8,7;C2,2; —

T15; P15,14;C2,2; 0

T16; P2,1;C2,2; 0

T17; P6,5;C3,2; Left Class II

T18; P9,8;C2,2; —

T19; P13,7;C3,3; Excess of the right hemiface and of the right horizontal branch S1 Anterior-posterior direction synthetic comment = strong right anteroposterior excess S2 Vertical direction synthetic comment = none S3 Transversal direction synthetic comment = left upper deviation (right excess) tendency

*FIG. 35A*

| Complete comments |
|---|
| T1; P2,1;C3,3; Overjet with Class II |
| T2; P19,1;C3,3; overjet by upper incisors protrusion |
| T3; P20,1;C1,3; (and) despite lower incisor protrusion, linear lower Class II compensation |
| T4; P22,1;C2,3; --- |
| T5; P4,3;C1,1; due to upper decrease and lower increase of incisors torque |
| T15; P3;C1,1; Typical Class II-2 aspect |
| T6; P6,2;C2,3; Occlusal Class II is not in agreement with a skeletal Class II |
| T7; P8,23;C3,2; Class II (skeletal or occlusal) is tied with mandible retrusion |
| T14; P7,9;C2,2; --- |
| T8; P21,5;C2,2; --- |
| T9; P26,13;C1,2; Maxilla height deficit versus mandible |
| T10; P14,13;C3,2; Facial hyperdivergence |
| T16; P14,27;C3,1; despite global dentition anterior convergence |
| T11; P12,11;C3,1; Alveolar hypodivergence despite basic hyperdivergence, in opposition to facial |
| T12; P16,15;C1,3; Maxilla alveolar linear excess with a torque compensation |
| T13; P18,17;C3,2; Architect anterior upper excess, maxilla vs mandible, (mental deïct) |
| Synthetic comments: |
| Anterior-posterior direction comment = Strong Class II. |

*FIG. 35B*

Applying an analysis engine or artificial intelligence in 3D biometry analysis

- A data-driven approach based on 3D biometry computation

Biometry data computation

- Example: Tooth Euler angles (i, a, and r angles)
- Euler angles
  - i = inclination
  - a = angulation
  - r = rotation Biometry data computation

- Example: Pseudo FMA (orbital floor/corpus angle)
  - *Angle of <MHM-MIO,MFM-MM>*

- Example: Difference of right/left basic mandible divergence

<RFM-RM,RHM-RIO>-<LFM-LM,LHM-LIO>

FIG. 44

AI biometry analysis system

- Disharmony (Off asymmetry) analysis with 16 AI tables (engines), Asymmetry analysis with 19 AI tables (engines)

$T$ – AI table

*asym T* – AI table

*D* – biometry data input

*C* – diagnosis comment output

Machine intelligence in 3D maxilla-facial biometry analysis report

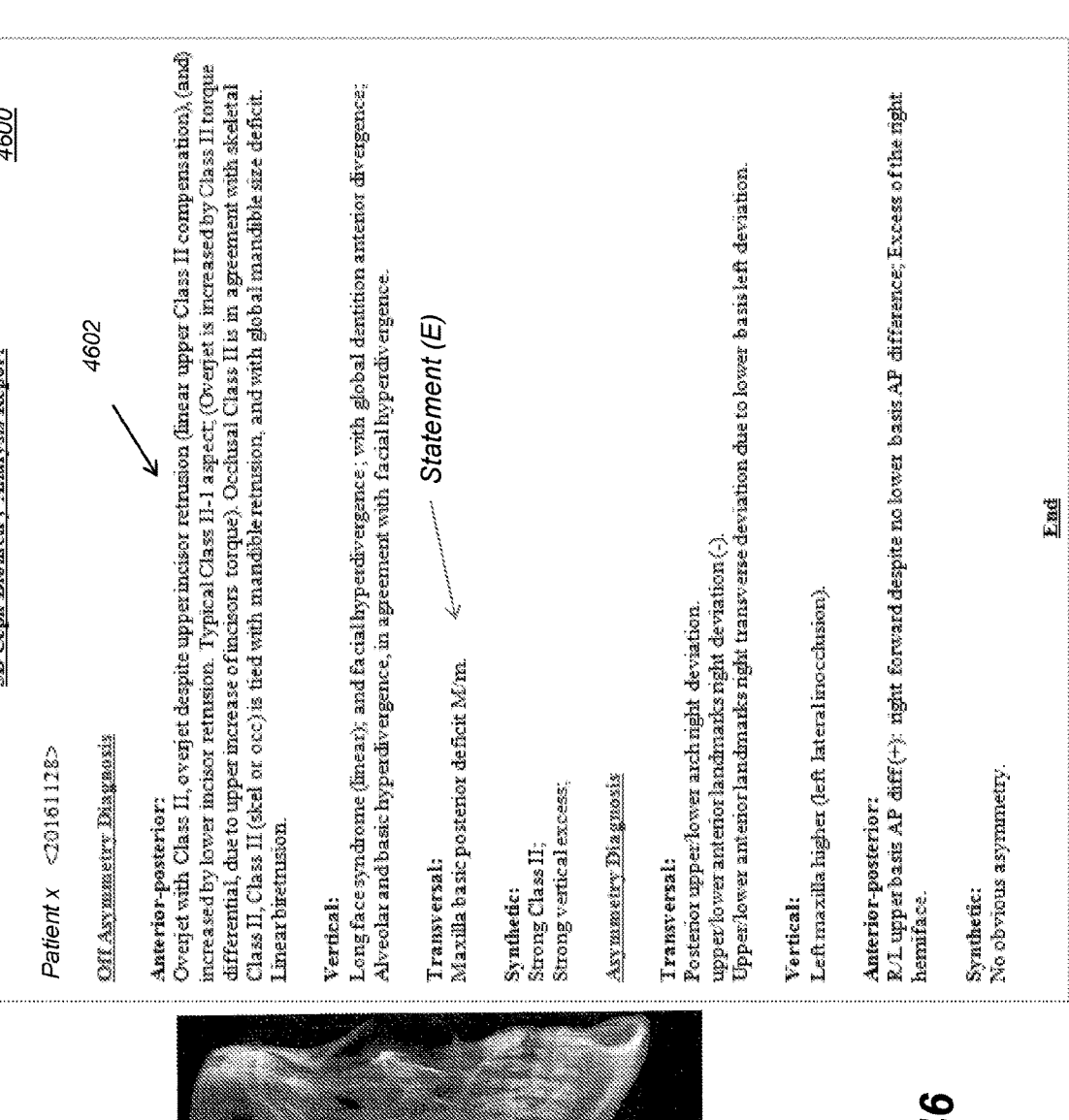

3D Ceph Biometry Analysis Report _4600_

_Patient x_ <20161128>

_4602_

Off Asymmetry Diagnosis

Anterior-posterior:
Overjet with Class II, overjet despite upper incisor retrusion (linear upper Class II compensation), (and) increased by lower incisor retrusion. Typical Class II-1 aspect (Overjet is increased by Class II torque differential, due to upper increase of incisors torque). Occlusal Class II is in agreement with skeletal Class II, Class II (skel or occ) is tied with mandible retrusion, and with global mandible size deficit. Linear biretrusion.

Vertical:
Long face syndrome (linear); and facial hyperdivergence; with global dentition anterior divergence; Alveolar and basic hyperdivergence, in agreement with facial hyperdivergence.

Statement (E)

Transversal:
Maxilla basic posterior deficit M/m.

Synthetic:
Strong Class II,
Strong vertical excess;

Asymmetry Diagnosis

Transversal:
Posterior upper/lower arch right deviation.
upper/lower anterior landmarks right deviation (-).
Upper/lower anterior landmarks right transverse deviation due to lower basis left deviation.

Vertical:
Left maxilla higher (left lateral in occlusion).

Anterior-posterior:
R/L upper basis AP diff (+): right forward despite no lower basis AP difference; Excess of the right hemiface.

Synthetic:
No obvious asymmetry.

End

*FIG. 46*

Diagnosis statement composition

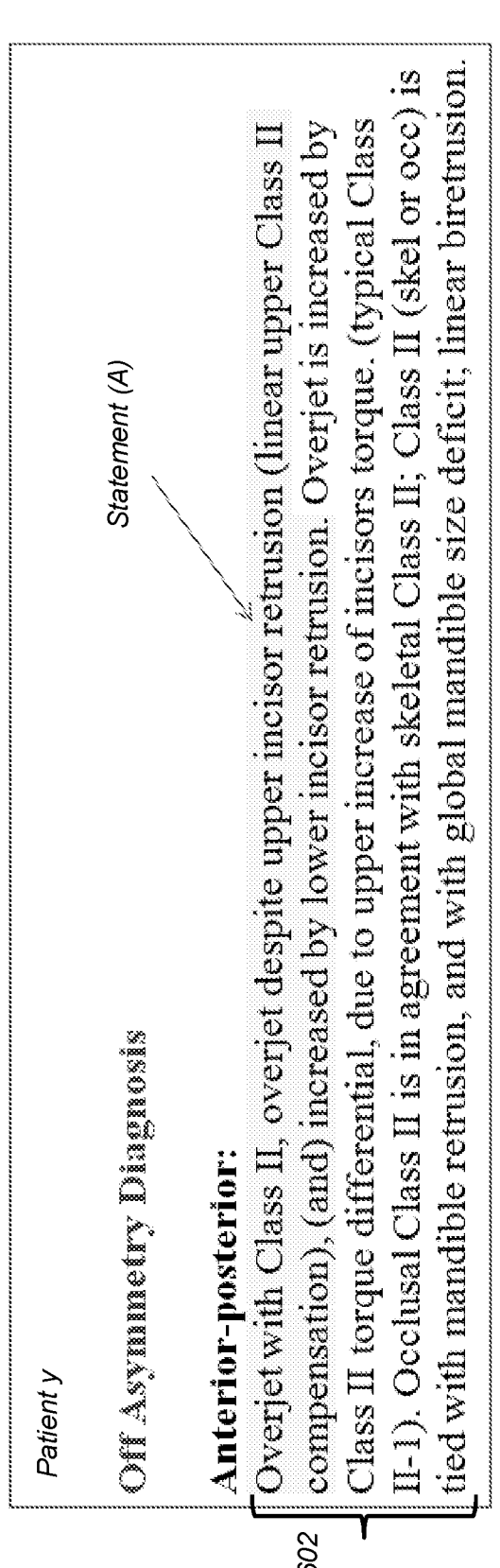

*Patient y*

Off Asymmetry Diagnosis

Anterior-posterior:
Overjet with Class II, overjet despite upper incisor retrusion (linear upper Class II compensation), (and) increased by lower incisor retrusion. Overjet is increased by Class II torque differential, due to upper increase of incisors torque. (typical Class II-1). Occlusal Class II is in agreement with skeletal Class II; Class II (skel or occ) is tied with mandible retrusion, and with global mandible size deficit; linear biretrusion.

*Statement (A)*

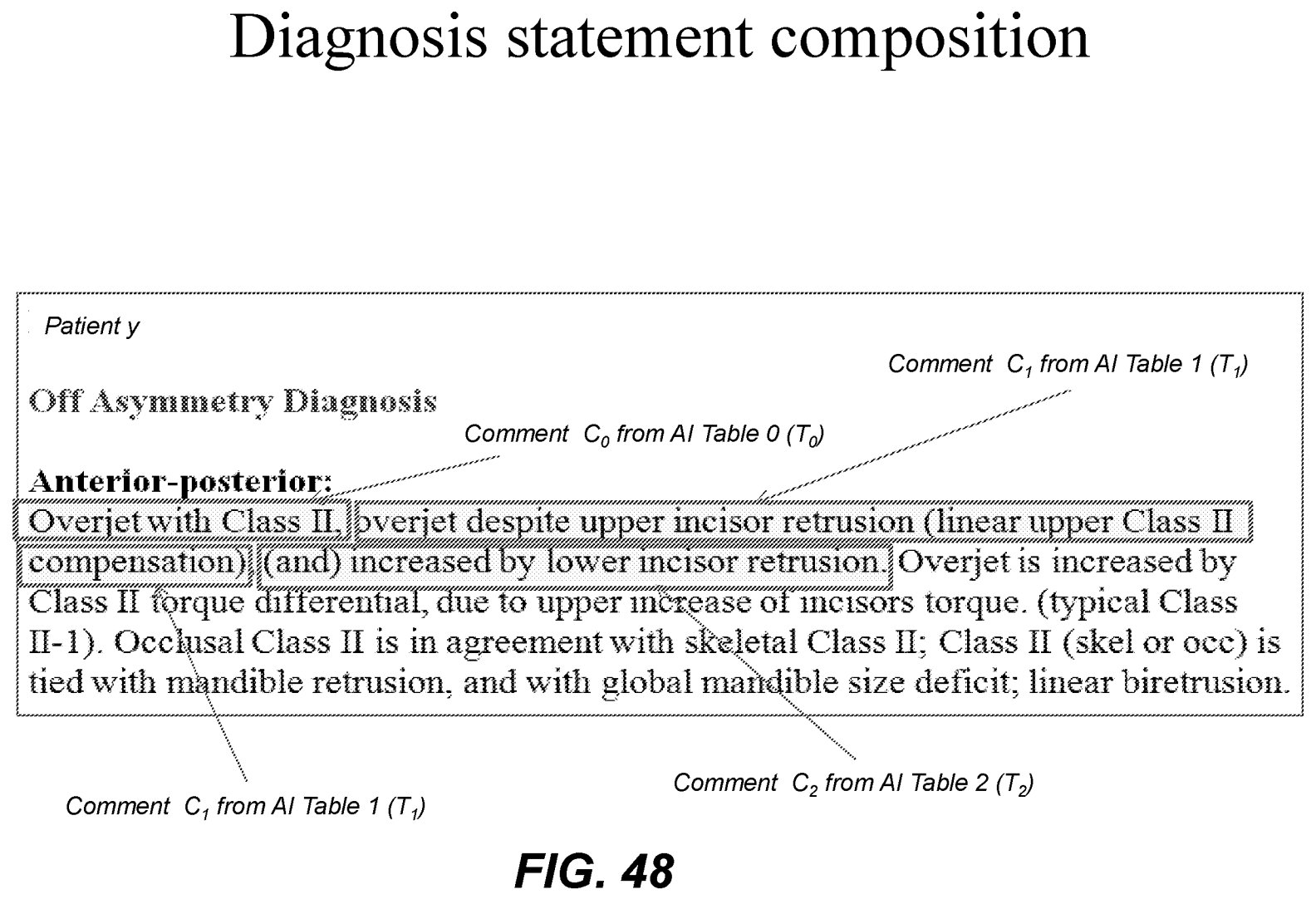

Diagnosis statement composition

Patient y

Off Asymmetry Diagnosis

Comment $C_0$ from AI Table 0 ($T_0$)

Anterior-posterior:
Overjet with Class II, overjet despite upper incisor retrusion (linear upper Class II compensation) (and) increased by lower incisor retrusion. Overjet is increased by Class II torque differential, due to upper increase of incisors torque. (typical Class II-1). Occlusal Class II is in agreement with skeletal Class II; Class II (skel or occ) is tied with mandible retrusion, and with global mandible size deficit; linear biretrusion.

Comment $C_1$ from AI Table 1 ($T_1$)

Comment $C_1$ from AI Table 1 ($T_1$)

Comment $C_2$ from AI Table 2 ($T_2$)

FIG. 48

Diagnosis statement (A) composition logic truth table (A) 4900

| | | | | Desired output |
|---|---|---|---|---|
| 1 | 1 | 1 | 1 | $C_0$ |
| 1 | 1 | 1 | 0 | $C_0$ |
| 1 | 1 | 0 | 1 | $C_0$ |
| 1 | 1 | 0 | 0 | $C_0$ |
| 1 | 0 | 1 | 1 | $C_0$ |
| 1 | 0 | 1 | 0 | $C_0+C_2$ |
| 1 | 0 | 0 | 1 | $C_0$ |
| 1 | 0 | 0 | 0 | $C_0+C_2$ |
| 0 | 1 | 1 | 1 | $C_0$ |
| 0 | 1 | 1 | 0 | $C_0$ |
| 0 | 1 | 0 | 1 | $C_0+C_1$ |
| 0 | 1 | 0 | 0 | $C_0+C_1$ |
| 0 | 0 | 1 | 1 | $C_0$ |
| 0 | 0 | 1 | 0 | $C_0+C_2$ |
| 0 | 0 | 0 | 1 | $C_0+C_1$ |
| 0 | 0 | 0 | 0 | $C_0+C_1+C_2$ |

*FIG. 49*

*Diagnosis statement (A) composition logic truth table (A) 4900*

*Diagnosis statement (A) composition logic circuitry (A) (build based on the logic truth table (A))*

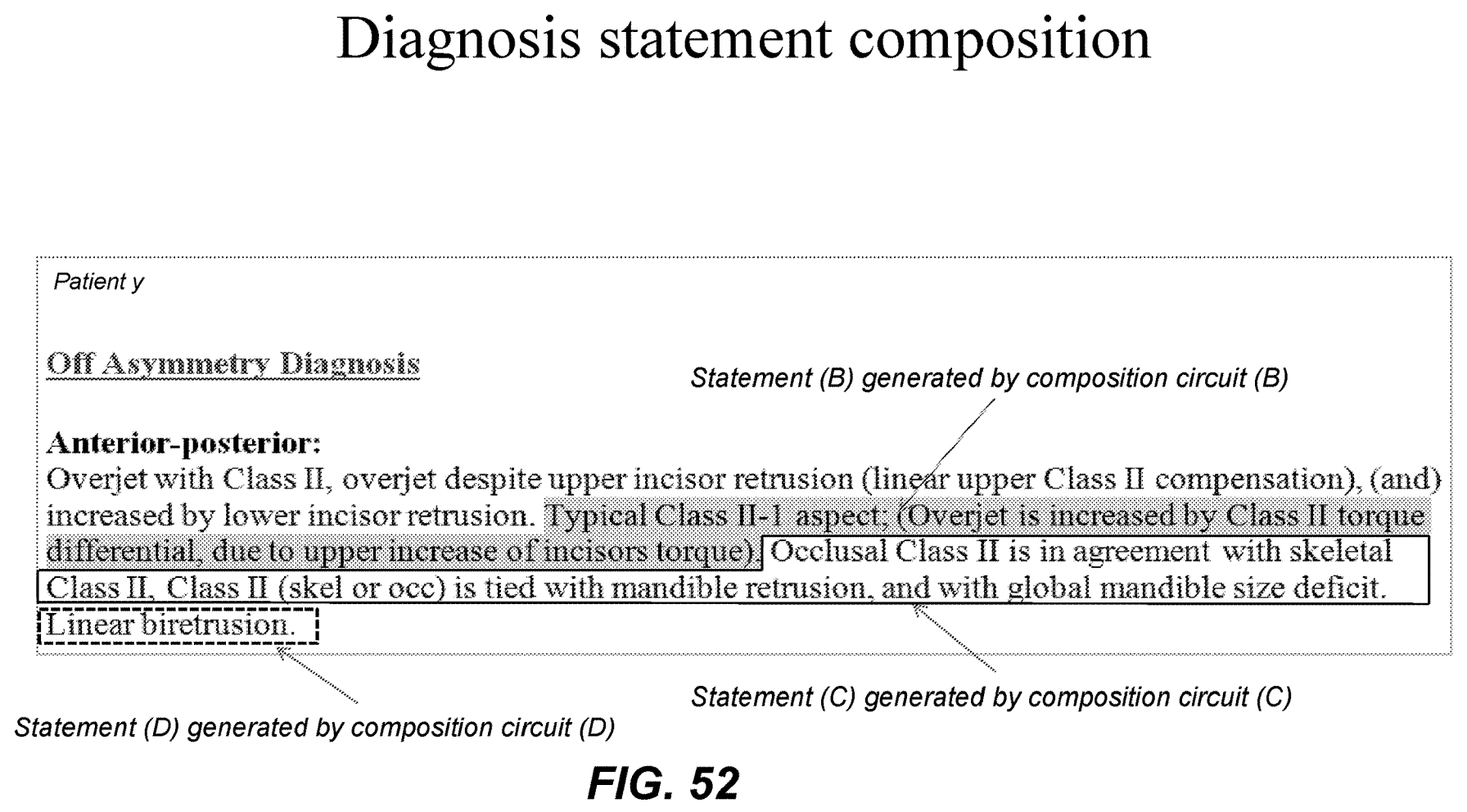

Diagnosis statement composition

*Patient y*

Off Asymmetry Diagnosis

Anterior-posterior:
Overjet with Class II, overjet despite upper incisor retrusion (linear upper Class II compensation), (and) increased by lower incisor retrusion. Typical Class II-1 aspect (Overjet is increased by Class II torque differential due to upper increase of incisors torque) Occlusal Class II is in agreement with skeletal Class II. Class II (skel or occ) is tied with mandible retrusion, and with global mandible size deficit.

Linear biretrusion.

*Statement (B) generated by composition circuit (B)*

*Statement (C) generated by composition circuit (C)*

*Statement (D) generated by composition circuit (D)*

*FIG. 52*

Diagnosis statement understanding

- Statement (E)

Statement (E)

Transversal:
Maxilla basic posterior deficit M/m.

- Not obvious just through CBCT volume examination

*It is evident, through biometry data computation, that maxilla posterior width is shorter than mandible posterior width*

RECONSTRUCTION OF A VIRTUAL COMPUTED-TOMOGRAPHY VOLUME TO TRACK ORTHODONTICS TREATMENT EVOLUTION

FIELD OF THE INVENTION

The present invention relates generally to image processing in x-ray computed tomography and, in particular, to acquiring 3-D data for three dimensional cephalometric analysis.

BACKGROUND OF THE INVENTION

Cephalometric analysis is the study of the dental and skeletal relationships for the head and is used by dentists and orthodontists as an assessment and planning tool for improved treatment of a patient. Conventional cephalometric analysis identifies bony and soft tissue landmarks in 2-D cephalometric radiographs in order to diagnose facial features and abnormalities prior to treatment, or to evaluate the progress of treatment.

For example, a dominant abnormality that can be identified in cephalometric analysis is the anteroposterior problem of malocclusion, relating to the skeletal relationship between the maxilla and mandible. Malocclusion is classified based on the relative position of the maxillary first molar. For Class I, neutrocclusion, the molar relationship is normal but other teeth may have problems such as spacing, crowding, or over- or under-eruption. For Class II, distocclusion, the mesiobuccal cusp of the maxillary first molar rests between the first mandible molar and second premolar. For Class III, mesiocclusion, the mesiobuccal cusp of the maxillary first molar is posterior to the mesiobuccal grooves of the mandibular first molar.

An exemplary conventional 2-D cephalometric analysis method described by Steiner in an article entitled "Cephalometrics in Clinical Practice" (paper read at the Charles H. Tweed Foundation for Orthodontic Research, October 1956, pp. 8-29) assesses maxilla and mandible in relation to the cranial base using angular measures. In the procedure described, Steiner selects four landmarks: Nasion, Point A, Point B and Sella. The Nasion is the intersection of the frontal bone and two nasal bones of the skull. Point A is regarded as the anterior limit of the apical base of the maxilla. Point B is regarded as the anterior limit of the apical base of the mandible. The Sella is at the mid-point of the sella turcica. The angle SNA (from Sella to Nasion, then to Point A) is used to determine if the maxilla is positioned anteriorly or posteriorly to the cranial base; a reading of about 82 degrees is regarded as normal. The angle SNB (from Sella to Nasion then to Point B) is used to determine if the mandible is positioned anteriorly or posteriorly to the cranial base; a reading of about 80 degrees is regarded as normal.

Recent studies in orthodontics indicate that there are persistent inaccuracies and inconsistencies in results provided using conventional 2-D cephalometric analysis. One notable study is entitled "In vivo comparison of conventional and cone beam CT synthesized cephalograms" by Vandana Kumar et al. in *Angle Orthodontics*, September 2008, pp. 873-879.

Due to fundamental limitations in data acquisition, conventional 2-D cephalometric analysis is focused primarily on aesthetics, without the concern of balance and symmetry about the human face. As stated in an article entitled "The human face as a 3D model for cephalometric analysis" by Treil et al. in *World Journal of Orthodontics*, pp. 1-6, plane geometry is inappropriate for analyzing anatomical volumes and their growth; only a 3-D diagnosis is able to suitably analyze the anatomical maxillofacial/dental complex. The normal relationship has two more significant aspects: balance and symmetry, when balance and symmetry of the model are stable, these characteristics define what is normal for each person.

U.S. Pat. No. 6,879,712, entitled "System and method of digitally modeling craniofacial features for the purposes of diagnosis and treatment predictions" to Tuncay et al., discloses a method of generating a computer model of craniofacial features. The three-dimensional facial features data are acquired using laser scanning and digital photographs; dental features are acquired by physically modeling the teeth. The models are laser scanned. Skeletal features are then obtained from radiographs. The data are combined into a single computer model that can be manipulated and viewed in three dimensions. The model also has the ability for animation between the current modeled craniofacial features and theoretical craniofacial features.

U.S. Pat. No. 6,250,918, entitled "Method and apparatus for simulating tooth movement for an orthodontic patient" to Sachdeva et al., discloses a method of determining a 3-D direct path of movement from a 3-D digital model of an actual orthodontic structure and a 3-D model of a desired orthodontic structure. This method simulates tooth movement based on each tooth's corresponding three-dimensional direct path using laser scanned crown and markers on the tooth surface for scaling. There is no true whole tooth 3-D data using the method described.

Although significant strides have been made toward developing techniques that automate entry of measurements and computation of biometric data for craniofacial features based on such measurements, there is considerable room for improvement. Even with the benefit of existing tools, the practitioner requires sufficient training in order to use the biometric data effectively. The sizable amount of measured and calculated data complicates the task of developing and maintaining a treatment plan and can increase the risks of human oversight and error.

Thus it can be seen that there would be particular value in development of analysis utilities that generate and report cephalometric results that can help to direct treatment planning and to track patient progress at different stages of ongoing treatment.

SUMMARY OF THE INVENTION

It is an object of the present disclosure to address the need for improved ways to acquire 3-D anatomical data for cephalometric analysis.

With this object in mind, the present disclosure provides a method for 3-D cephalometric analysis, the method executed at least in part on a computer processor and comprising providing an initial CT volume of a patient, the initial CT volume ($CT_0$) comprising maxilla bone and mandible bone, and crowns and roots for a plurality of teeth; segmenting crowns, roots and bones out of the initial CT volume ($CT_0$) to produce an initial segmented CT volume ($SCT_0$); producing an initial set of biometric parameters ($S_0$) from the initial segmented CT volume ($SCT_0$) and other anatomical features within the SCT0, using an artificial intelligence engine whose data structure contains information reflecting relationship between segmented crowns, roots and bones; re-arranging the segmented crowns, roots and bones according to a modified relationship between segmented crowns, roots and bones determined by the artificial intelligence engine to produce a final virtual CT volume ($CT_{end}$), said rearrangement step being done using the at least one invariant landmark; and displaying, storing or transmitting the final CT Volume ($CT_{end}$).

Embodiments of the present disclosure, in a synergistic manner, integrate skills of a human operator of the system with computer capabilities for feature identification. This takes advantage of human skills of creativity, use of heuristics, flexibility, and judgment, and combines these with computer advantages, such as speed of computation, capability for exhaustive and accurate processing, and reporting and data access capabilities.

These and other aspects, objects, features and advantages of the present disclosure will be more clearly understood and appreciated from a review of the following detailed description of the preferred embodiments and appended claims, and by reference to the accompanying drawings.

BRIEF DESCRIPTION OF THE DRAWINGS

The foregoing and other objects, features, and advantages of the invention will be apparent from the following more particular description of the embodiments of the disclosure, as illustrated in the accompanying drawings. The elements of the drawings are not necessarily to scale relative to each other.

FIG. 6 is a view of 3-D rendered CBCT head volume images with a set of 3-D reference marks displayed.

FIGS. 7A, 7B, and 7C are perspective views that show identified anatomical features that provide a framework for cephalometric analysis.

FIG. 29 shows pseudo-code for an algorithm using the independent network arrangement of FIG. 27.

FIG. 30 shows pseudo-code for an algorithm using the dependent network arrangement of FIG. 28.

FIG. 31A lists example parameters as numerical values and their interpretation.

FIGS. 31B, 31C and 31D list, for a particular patient, example parameters as numerical values and their interpretation with respect to maxilofacial asymmetry, based on exemplary total maxilofacial asymmetry parameters according to exemplary embodiments of this application.

FIG. 32A shows exemplary tabulated results for a particular example with bite analysis and arches angle characteristics.

FIG. 32B shows exemplary tabulated results for a particular example for torque of upper and lower incisors.

FIG. 32C shows exemplary tabulated results for another example with assessment of biretrusion or biprotrusion.

FIG. 32D shows an exemplary summary listing of results for cephalometric analysis of a particular patient.

FIG. 32E shows a detailed listing for one of the conditions listed in FIG. 35A.

FIG. 35A shows an exemplary report for asymmetry according to an embodiment of the present disclosure.

FIG. 35B shows an exemplary report for off-asymmetry according to an embodiment of the present disclosure.

FIGS. 42, 43, and 44 are diagrams that illustrate exemplary data terms that include tooth Euler angles, Pseudo FMA, and Difference of right/left basic mandible divergence, respectively.

FIG. 46 presents an exemplary biometry analysis report generated through a machine intelligence mechanism according to exemplary method and/or apparatus embodiments of this application.

FIGS. 47-48 are diagrams that show an exemplary Anterior-posterior description for an Off Asymmetry Diagnosis that includes at least one composite statement according to certain exemplary embodiments.

FIGS. 49-50 are diagrams that show an exemplary composition logic truth table for controlling the intelligent reporting system, which can be used for implementing a representative composite statement representing a maxillofacial/dental abnormality.

FIG. 52 is a diagram that shows that statement A of Anterior-posterior description includes four composite descriptive statements, which each can be generated by a composition circuit.

DETAILED DESCRIPTION OF THE INVENTION

Figure 1:
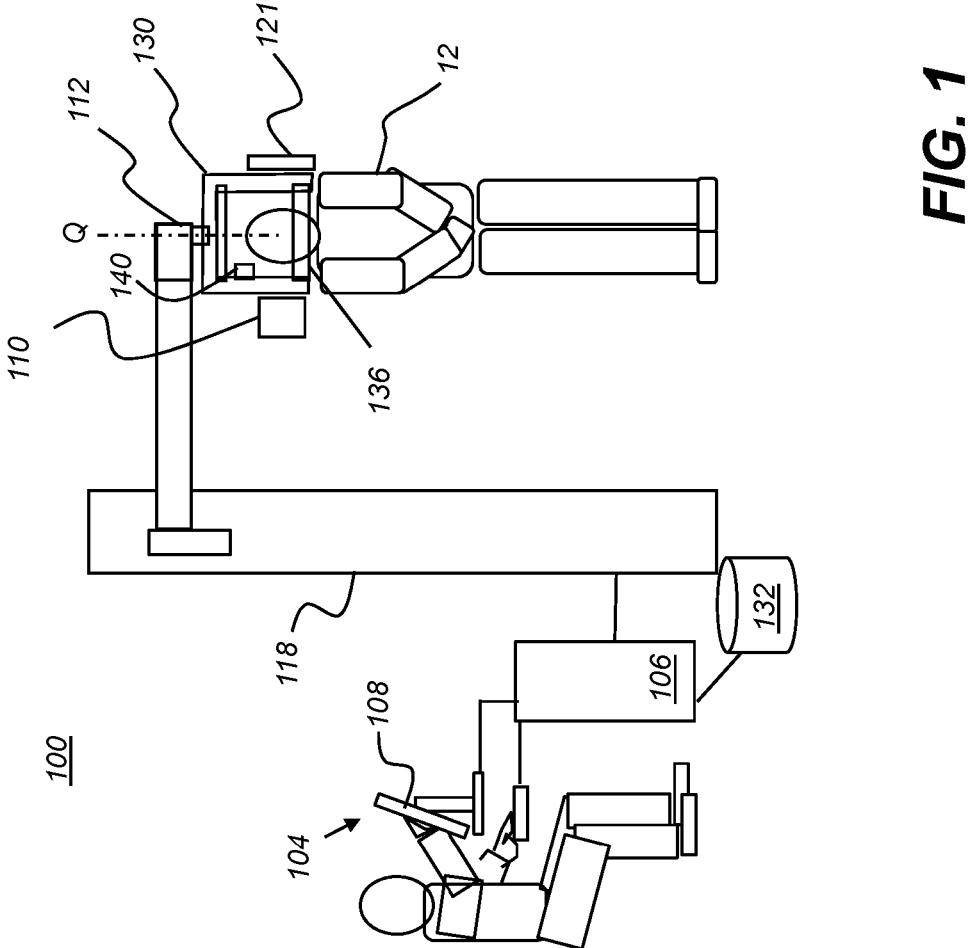
FIG. 1 is a schematic diagram showing an imaging system for providing cephalometric analysis.

In the following detailed description of embodiments of the present disclosure, reference is made to the drawings in which the same reference numerals are assigned to identical elements in successive figures. It should be noted that these figures are provided to illustrate overall functions and relationships according to embodiments of the present invention and are not provided with intent to represent actual size or scale.

Where they are used, the terms "first", "second", "third", and so on, do not necessarily denote any ordinal or priority relation, but may be used for more clearly distinguishing one element or time interval from another.

In the context of the present disclosure, the term "image" refers to multi-dimensional image data that is composed of discrete image elements. For 2-D images, the discrete image elements are picture elements, or pixels. For 3-D images, the discrete image elements are volume image elements, or voxels. The term "volume image" is considered to be synonymous with the term "3-D image".

In the context of the present disclosure, the term "code value" refers to the value that is associated with each 2-D image pixel or, correspondingly, each volume image data element or voxel in the reconstructed 3-D volume image. The code values for computed tomography (CT) or cone-beam computed tomography (CBCT) images are often, but not always, expressed in Hounsfield units that provide information on the attenuation coefficient of each voxel.

In the context of the present disclosure, the term "geometric primitive" relates to an open or closed shape such as a rectangle, circle, line, traced curve, or other traced pattern. The terms "landmark" and "anatomical feature" are considered to be equivalent and refer to specific features of patient anatomy as displayed.

In the context of the present disclosure, the terms "viewer", "operator", and "user" are considered to be equivalent and refer to the viewing practitioner or other person who views and manipulates an image, such as a dental image, on a display monitor. An "operator instruction" or "viewer instruction" is obtained from explicit commands entered by the viewer, such as using a computer mouse or touch screen or keyboard entry.

The term "highlighting" for a displayed feature has its conventional meaning as is understood to those skilled in the information and image display arts. In general, highlighting uses some form of localized display enhancement to attract the attention of the viewer. Highlighting a portion of an image, such as an individual organ, bone, or structure, or a path from one chamber to the next, for example, can be achieved in any of a number of ways, including, but not limited to, annotating, displaying a nearby or overlaying symbol, outlining or tracing, display in a different color or at a markedly different intensity or gray scale value than other image or information content, blinking or animation of a portion of a display, or display at higher sharpness or contrast. In the context of the present disclosure, the descriptive term "derived parameters" relates to values calculated from processing of acquired or entered data values. Derived parameters may be a scalar, a point, a line, a volume, a vector, a plane, a curve, an angular value, an image, a closed contour, an area, a length, a matrix, a tensor, or a mathematical expression.

The term "set", as used herein, refers to a non-empty set, as the concept of a collection of elements or members of a set is widely understood in elementary mathematics. The term "subset", unless otherwise explicitly stated, is used herein to refer to a non-empty proper subset, that is, to a subset of the larger set, having one or more members. For a set S, a subset may comprise the complete set S. A "proper subset" of set S, however, is strictly contained in set S and excludes at least one member of set S. Alternately, more formally stated, as the term is used in the present disclosure, a subset B can be considered to be a proper subset of set S if (i) subset B is non-empty and (ii) if B∩S is also non-empty and subset B further contains only elements that are in set S and has a cardinality that is less than that of set S.

In the context of the present disclosure, a "plan view" or "2-D view" is a 2-dimensional (2-D) representation or projection of a 3-dimensional (3-D) object from the position of a horizontal plane through the object. This term is synonymous with the term "image slice" that is conventionally used to describe displaying a 2-D planar representation from within 3-D volume image data from a particular perspective. 2-D views of the 3-D volume data are considered to be substantially orthogonal if the corresponding planes at which the views are taken are disposed at 90 (+/−10) degrees from each other, or at an integer multiple n of 90 degrees from each other (n*90 degrees, +/−10 degrees).

In the context of the present disclosure, the general term "dentition element" relates to teeth, prosthetic devices such as dentures and implants, and supporting structures for teeth and associated prosthetic device, including jaws.

In the context of the present disclosure, the general term "aligner or aligners" relates to conventional orthodontic appliances, including but not limited to traditional metal wired braces, clear braces, lingual braces, multi-loop edgewise archwire technique appliances, customized orthodontic treatment systems, progressive clear removable aligners, smart brackets, A-braces, partial braces, and/or custom brackets (e.g., vestibular or lingual).

The subject matter of the present disclosure relates to digital image processing and computer vision technologies, which is understood to mean technologies that digitally process data from a digital image to recognize and thereby assign useful meaning to human-understandable objects, attributes or conditions, and then to utilize the results obtained in further processing of the digital image.

As noted earlier in the background section, conventional 2-D cephalometric analysis has a number of significant drawbacks. It is difficult to center the patient's head in the cephalostat or other measuring device, making reproducibility unlikely. The two dimensional radiographs that are obtained produce overlapped head anatomy images rather than 3-D images. Locating landmarks on cephalograms can be difficult and results are often inconsistent (see the article entitled "Cephalometrics for the next millennium" by P. Planche and J. Treil in *The Future of Orthodontics*, ed. Carine Carels, Guy Willems, Leuven University Press, 1998, pp. 181-192). The job of developing and tracking a treatment plan is complex, in part, because of the significant amount of cephalometric data that is collected and calculated.

An embodiment of the present disclosure utilizes Treil's theory in terms of the selection of 3-D anatomic feature points, parameters derived from these feature points, and the way to use these derived parameters in cephalometric analysis. Reference publications authored by Treil include "The Human Face as a 3D Model for Cephalometric Analysis" Jacques Treil, B, Waysenson, J. Braga and J. Casteigt in *World Journal of Orthodontics*, 2005 Supplement, Vol. 6, issue 5, pp. 33-38; and "3D Tooth Modeling for Orthodontic Assessment" by J. Treil, J. Braga, J.-M. Loubes, E. Maza, J.-M. Inglese, J. Casteigt, and B. Waysenson in *Seminars in Orthodontics*, Vol. 15, No. 1, March 2009).

The schematic diagram of FIG. 1 shows an imaging apparatus 100 for 3-D CBCT cephalometric imaging. For imaging a patient 12, a succession of multiple 2-D projection images is obtained and processed using imaging apparatus 100. A rotatable mount 130 is provided on a column 118, preferably adjustable in height to suit the size of patient 12. Mount 130 maintains an x-ray source 110 and a radiation sensor 121 on opposite sides of the head of patient 12 and rotates to orbit source 110 and sensor 121 in a scan pattern about the head. Mount 130 rotates about an axis Q that corresponds to a central portion of the patient's head, so that components attached to mount 130 orbit the head. Sensor 121, a digital sensor, is coupled to mount 130, opposite x-ray source 110 that emits a radiation pattern suitable for CBCT volume imaging. An optional head support 136, such as a chin rest or bite element, provides stabilization of the patient's head during image acquisition. A computer 106 has an operator interface 104 and a display 108 for accepting operator commands and for display of volume images of the orthodontia image data obtained by imaging apparatus 100. Computer 106 is in signal communication with sensor 121 for obtaining image data and provides signals for control of source 110 and, optionally, for control of a rotational actuator 112 for mount 130 components. Computer 106 is also in signal communication with a memory 132 for storing image data. An optional alignment apparatus 140 is provided to assist in proper alignment of the patient's head for the imaging process.

Figure 2:
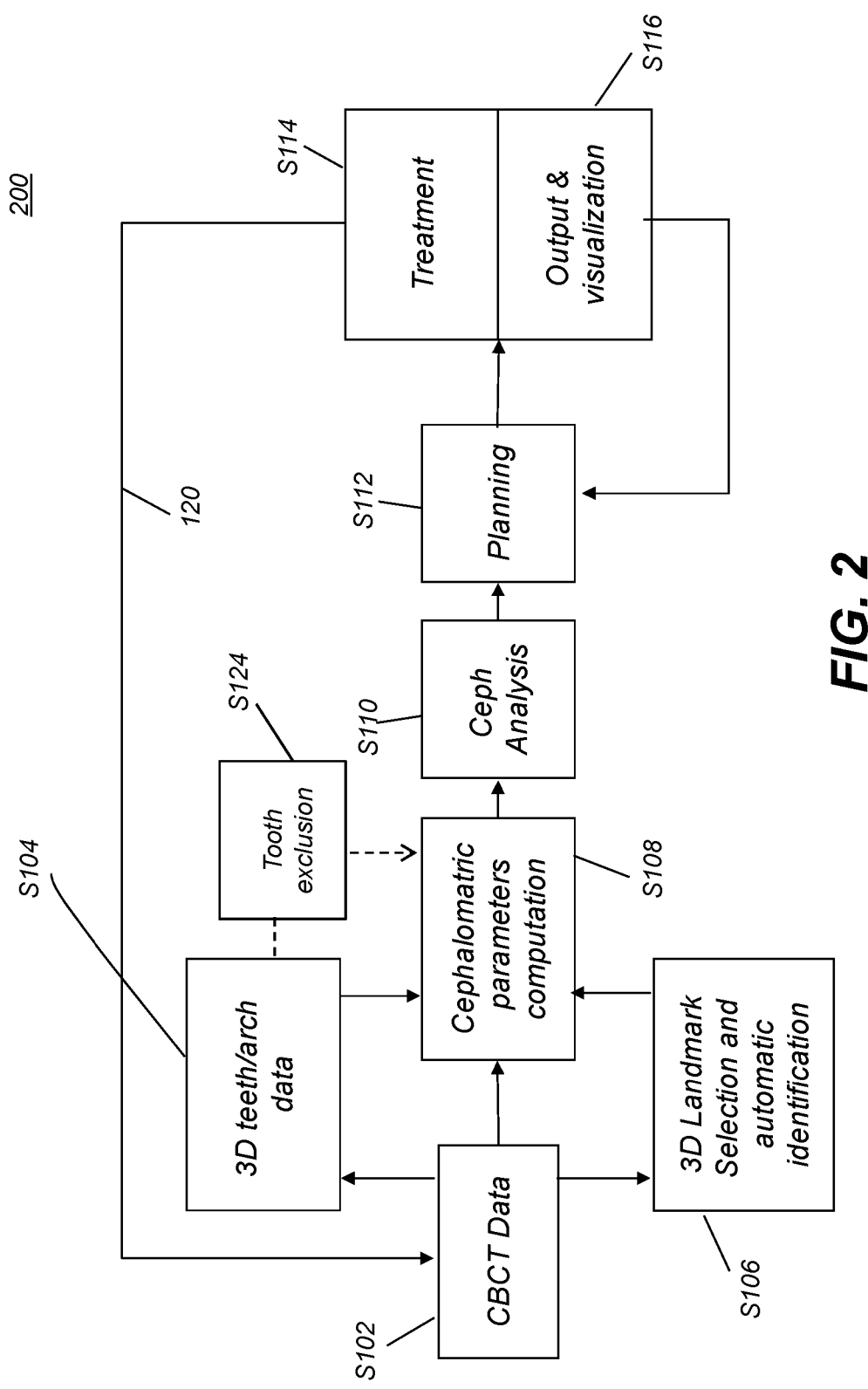
FIG. 2 is a logic flow diagram showing processes for 3-D cephalometric analysis according to an embodiment of the present disclosure.
Figure 3:
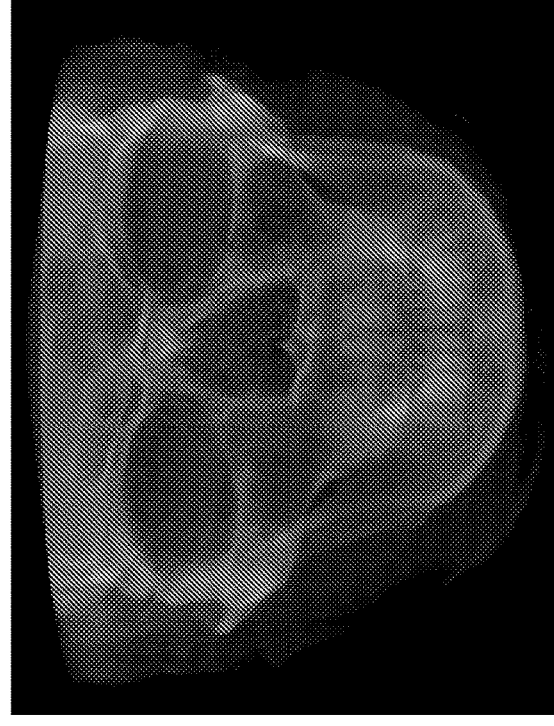
FIG. 3 is a view of 3-D rendered CBCT head volume images.

Referring to the logic flow diagram of FIG. 2, there is shown a sequence 200 of steps used for acquiring orthodontia data for 3-D cephalometric analysis with a dental CBCT volume according to an embodiment of the present disclosure. The CBCT volume image data is accessed in a data acquisition step S102. A volume contains image data for one or more 2-D images (or equivalently, slices). An original reconstructed CT volume is formed using standard reconstruction algorithms using multiple 2-D projections or sinograms obtained from a CT scanner. By way of example, FIG. 3 shows an exemplary dental CBCT volume 202 that contains bony anatomy, soft tissues, and teeth.

Continuing with the sequence of FIG. 2, in a segmentation step S104, 3-D dentition element data are collected by applying a 3-D tooth segmentation algorithm to the dental CBCT volume 202. Segmentation algorithms for teeth and related dentition elements are well known in the dental imaging arts. Exemplary tooth segmentation algorithms are described, for example, in commonly assigned U.S. Patent Application Publication No. 2013/0022252 entitled "PANORAMIC IMAGE GENERATION FROM CBCT DENTAL IMAGES" by Chen et al.; in U.S. Patent Application Publication No. 2013/0022255 entitled "METHOD AND SYSTEM FOR TOOTH SEGMENTATION IN DENTAL IMAGES" by Chen et al.; and in U.S. Patent Application Publication No. 2013/0022254 entitled "METHOD FOR TOOTH DISSECTION IN CBCT VOLUME" by Chen, incorporated herein by reference in its entirety.

Figure 4:
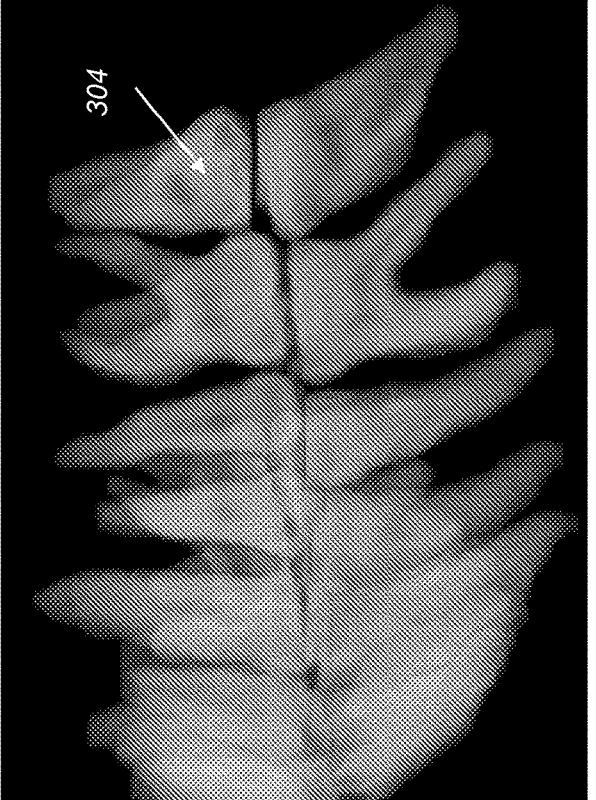
FIG. 4 is a view of a 3-D rendered teeth volume image after teeth segmentation.

As is shown in FIG. 4, tooth segmentation results are rendered with an image 302, wherein teeth are rendered as a whole but are segmented individually. Each tooth is a separate entity called a tooth volume, for example, tooth volume 304.

Each tooth of the segmented teeth or, more broadly, each dentition element that has been segmented has, at a minimum, a 3-D position list that contains 3-D position coordinates for each of the voxels within the segmented dentition element, and a code value list of each of the voxels within the segmented element. At this point, the 3-D position for each of the voxels is defined with respect to the CBCT volume coordinate system.

In a reference mark selection step S106 in the sequence of FIG. 2, the CBCT volume images display with two or more different 2-D views, obtained with respect to different view angles. The different 2-D views can be at different angles and may be different image slices, or may be orthographic or substantially orthographic projections, or may be perspective views, for example. According to an embodiment of the present disclosure, the three views are mutually orthogonal.

Figure 5:
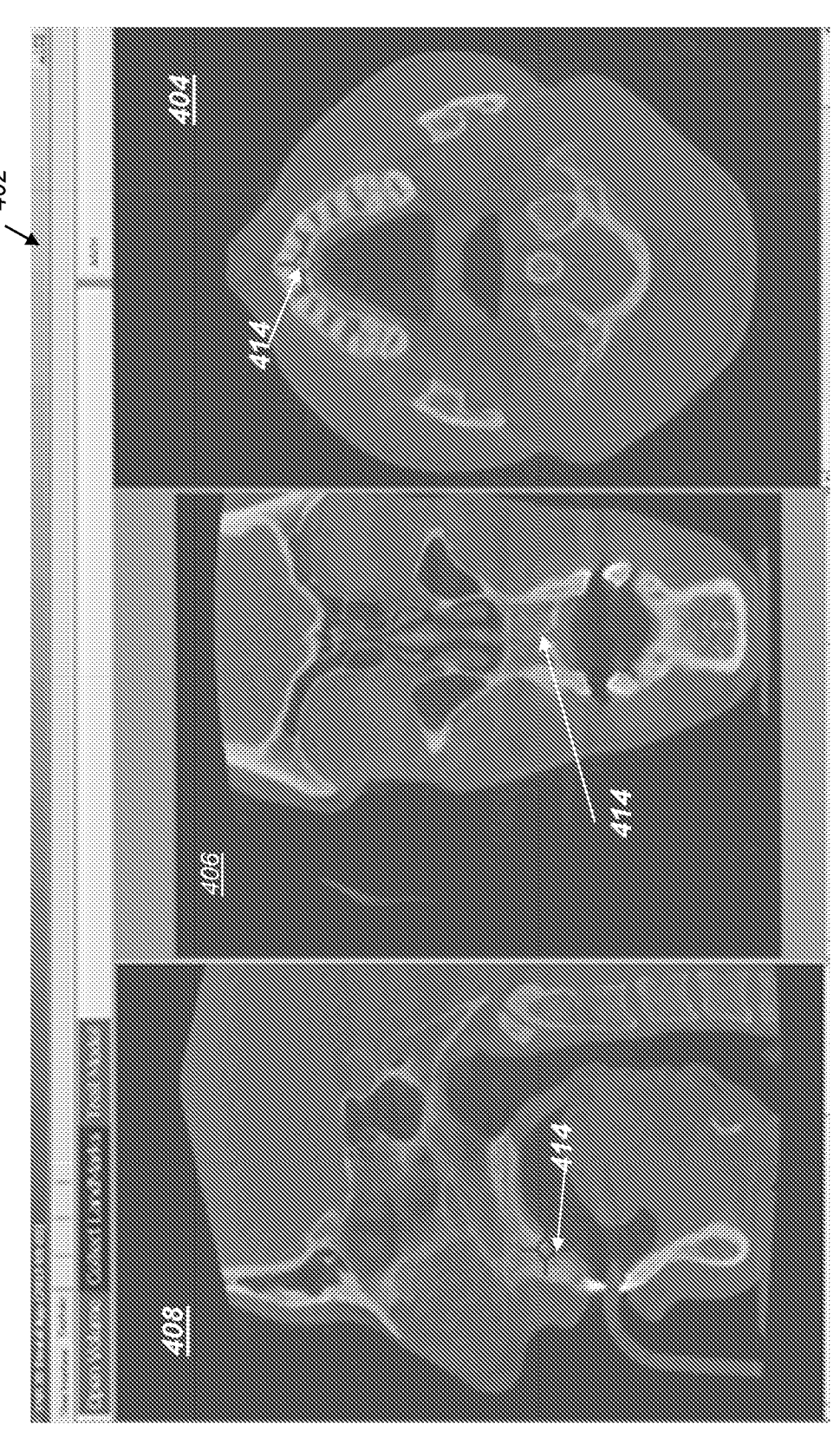
FIG. 5 is a view of a user interface that displays three orthogonal views of the CBCT head volume images and operator-entered reference marks.

FIG. 5 shows an exemplary format with a display interface 402 showing three orthogonal 2-D views. In display interface 402, an image 404 is one of the axial 2-D views of the CBCT volume image 202 (FIG. 3), an image 406 is one of the coronal 2-D views of the CBCT volume image 202, and an image 408 is one of the sagittal 2-D views of the CBCT volume image 202. The display interface allows a viewer, such as a practitioner or technician, to interact with the computer system that executes various image processing/computer algorithms in order to accomplish a plurality of 3-D cephalometric analysis tasks. Viewer interaction can take any of a number of forms known to those skilled in the user interface arts, such as using a pointer such as a computer mouse joystick or touchpad, or using a touch screen for selecting an action or specifying a coordinate of the image, for interaction described in more detail subsequently.

Figures 6, 7A:
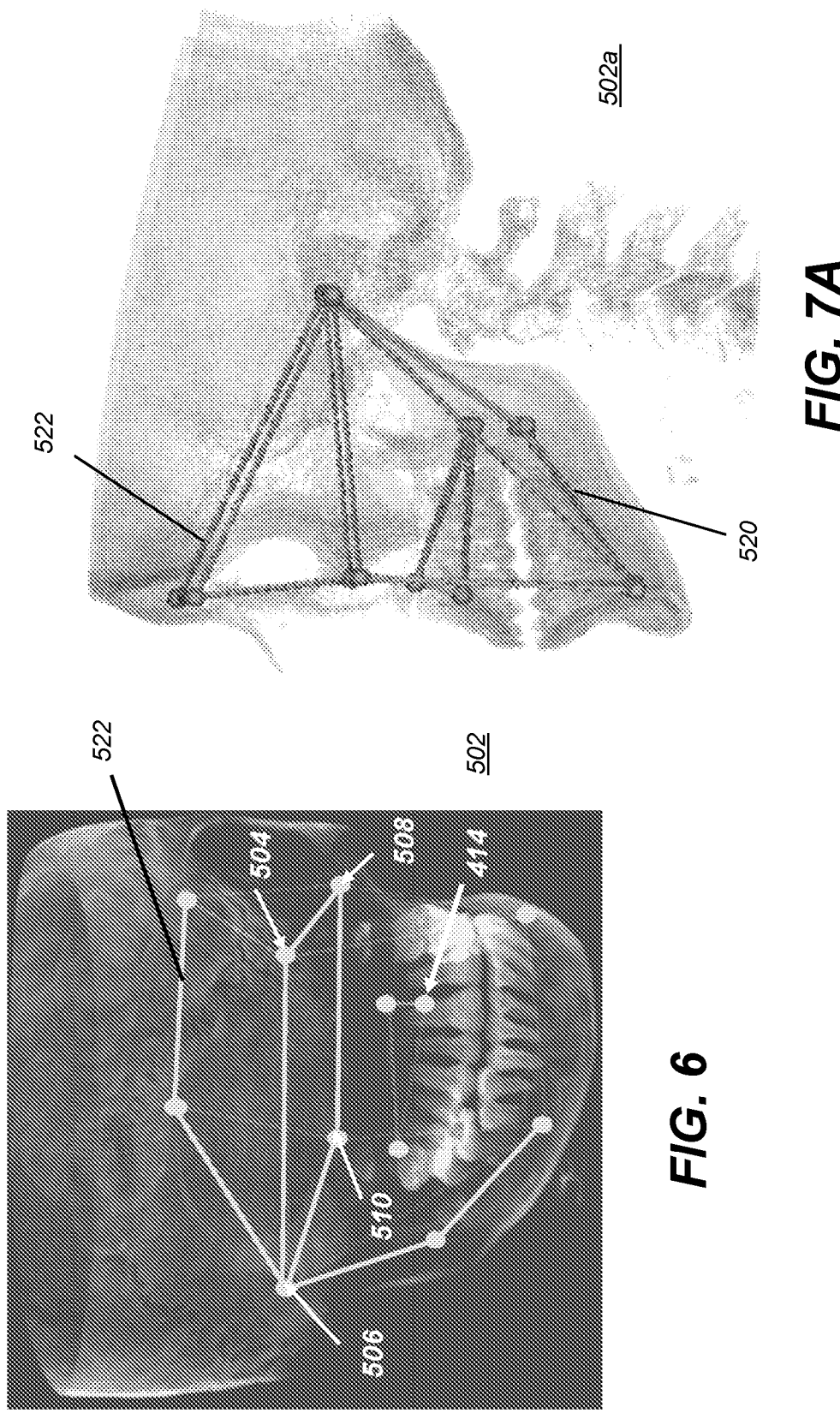

One of the 3-D cephalometric analysis tasks is to perform automatic identification in 3-D reference mark selection step S106 of FIG. 2. The 3-D reference marks, equivalent to a type of 3-D landmark or feature point identified by the viewer on the displayed image, are shown in the different mutually orthogonal 2-D views of display interface 402 in FIG. 5. Exemplary 3-D anatomic reference marks shown in FIG. 5 are lower nasal palatine foramen at reference mark 414. As shown in the view of FIG. 6, other anatomic reference marks that can be indicated by the viewer on a displayed image 502 include infraorbital foramina at reference marks 508 and 510, and malleus at reference marks 504 and 506.

In step S106 of FIG. 2, the viewer uses a pointing device (such as a mouse or touch screen, for example) to place a reference mark as a type of geometric primitive at an appropriate position in any one of the three views. According to an embodiment of the present disclosure that is shown in FIGS. herein, the reference mark displays as a circle. Using the display interface screen of FIG. 5, for example, the viewer places a small circle in the view shown as image 404 at location 414 as the reference mark for a reference point. Reference mark 414 displays as a small circle in image 404 as well as at the proper position in corresponding views in images 406 and 408. It is instructive to note that the viewer need only indicate the location of the reference mark 414 in one of the displayed views 404, 406 or 408; the system responds by showing the same reference mark 414 in other views of the patient anatomy. Thus, the viewer can identify the reference mark 414 in the view in which it is most readily visible.

After entering the reference mark 414, the user can use operator interface tools such as the keyboard or displayed icons in order to adjust the position of the reference mark 414 on any of the displayed views. The viewer also has the option to remove the entered reference mark and enter a new one.

The display interface 402 (FIG. 5) provides zoom in/out utilities for re-sizing any or all of the displayed views. The viewer can thus manipulate the different images efficiently for improved reference mark positioning.

The collection of reference marks made with reference to and appearing on views of the 3-D image content, provides a set of cephalometric parameters that can be used for a more precise characterization of the patient's head shape and structure. Cephalometric parameters include coordinate information that is provided directly by the reference mark entry for particular features of the patient's head. Cephalometric parameters also include information on various measurable characteristics of the anatomy of a patient's head that are not directly entered as coordinate or geometric structures but are derived from coordinate information, termed "derived cephalometric parameters". Derived cephalometric parameters can provide information on relative size or volume, symmetry, orientation, shape, movement paths and possible range of movement, axes of inertia, center of mass, and other data. In the context of the present disclosure, the term "cephalometric parameters" applies to those that are either directly identified, such as by the reference marks, or those derived cephalometric parameters that are computed according to the reference marks. For example, as particular reference points are identified by their corresponding reference marks, framework connecting lines 522 are constructed to join the reference points for a suitable characterization of overall features, as is more clearly shown in FIG. 6. Framework connecting lines 522 can be considered as vectors in 3-D space; their dimensional and spatial characteristics provide additional volume image data that can be used in computation for orthodontia and other purposes.

Each reference mark 414, 504, 506, 508, 510 is the terminal point for one or more framework connecting lines 522, generated automatically within the volume data by computer 106 of image processing apparatus 100 and forming a framework that facilitates subsequent analysis and measurement processing. FIGS. 7A, 7B, and 7C show, for displayed 3-D images 502a, 502b, and 502c from different perspective views, how a framework 520 of selected reference points, with the reference points at the vertices, helps to define dimensional aspects of the overall head structure. According to an embodiment of the present disclosure, an operator instruction allows the operator to toggle between 2-D views similar to those shown in FIG. 5 and the volume representation shown in FIG. 6, with partial transparency for voxels of the patient's head. This enables the operator to examine reference mark placement and connecting line placement from a number of angles; adjustment of reference mark position can be made on any of the displayed views. In addition, according to an embodiment of the present disclosure, the operator can type in more precise coordinates for a specific reference mark.

Figure 8:
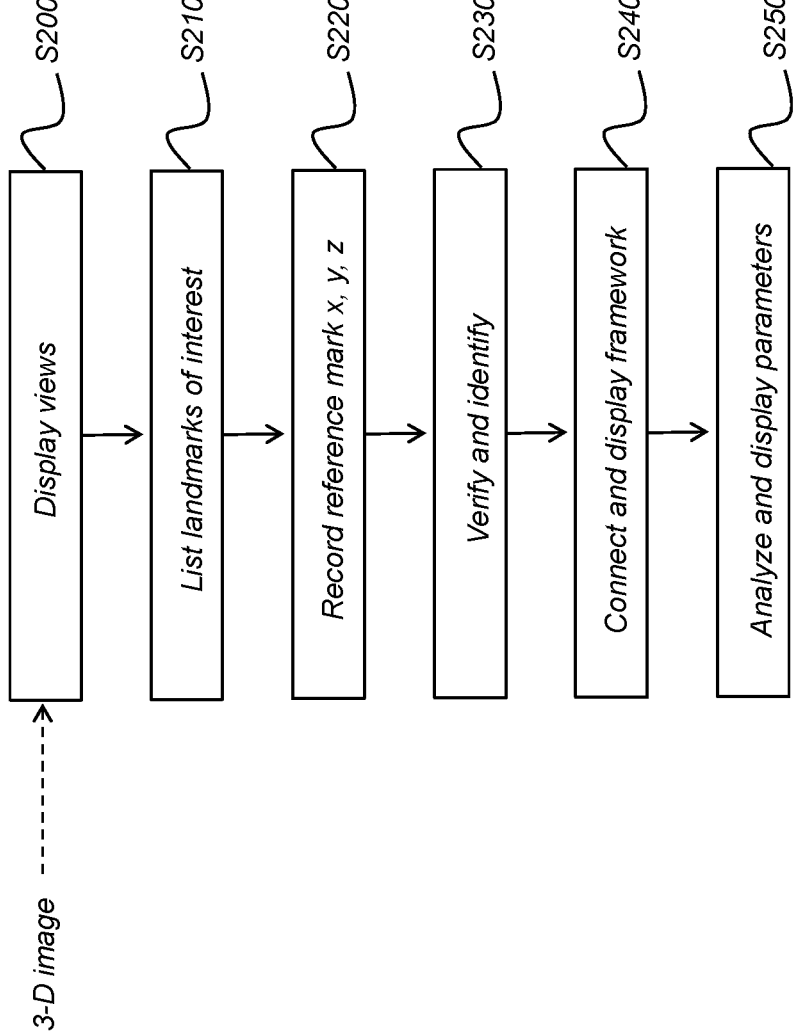
FIG. 8 is a logic flow diagram that shows steps for accepting operator instructions that generate the framework used for cephalometric analysis.

The logic flow diagram of FIG. 8 shows steps in a sequence for accepting and processing operator instructions for reference mark entry and identification and for providing computed parameters according to the image data and reference marks. A display step S200 displays one or more 2-D views, from different angles, such as from mutually orthogonal angles, for example, of reconstructed 3-D image data from a computed tomographic scan of a patient's head. In an optional listing step S210, the system provides a text listing such as a tabular list, a series of prompts, or a succession of labeled fields for numeric entry that requires entry of positional data for a number of landmarks or anatomical features in the reconstructed 3-D image. This listing may be explicitly provided for the operator in the form of user interface prompts or menu selection, as described subsequently. Alternately, the listing may be implicitly defined, so that the operator need not follow a specific sequence for entering positional information. Reference marks that give the x, y, z positional data for different anatomical features are entered in a recording step S220. Anatomical features can lie within or outside of the mouth of the patient. Embodiments of the present disclosure can use a combination of anatomical features identified on the display, as entered in step S220, and segmentation data automatically generated for teeth and other dentition elements, as noted previously with reference to FIG. 2.

In recording step S220 of FIG. 8, the system accepts operator instructions that position a reference mark corresponding to each landmark feature of the anatomy. The reference mark is entered by the operator on either the first or the second 2-D view, or on any of the other views if more than two views are presented and, following entry, displays on each of the displayed views. An identification step S230 identifies the anatomical feature or landmark that corresponds to the entered reference mark and, optionally, verifies the accuracy of the operator entry. Proportional values are calculated to determine the likelihood that a given operator entry accurately identifies the position of a reference mark for a particular anatomical feature. For example, the infraorbital foramen is typically within a certain distance range from the palatine foramen; the system checks the entered distance and notifies the operator if the corresponding reference mark does not appear to be properly positioned.

Continuing with the sequence of FIG. 8, in a construction step S240, framework connecting lines are generated to connect reference marks for frame generation. A computation and display step S250 is then executed, computing one or more cephalometric parameters according to the positioned reference marks. The computed parameters are then displayed to the operator.

Figure 9A:
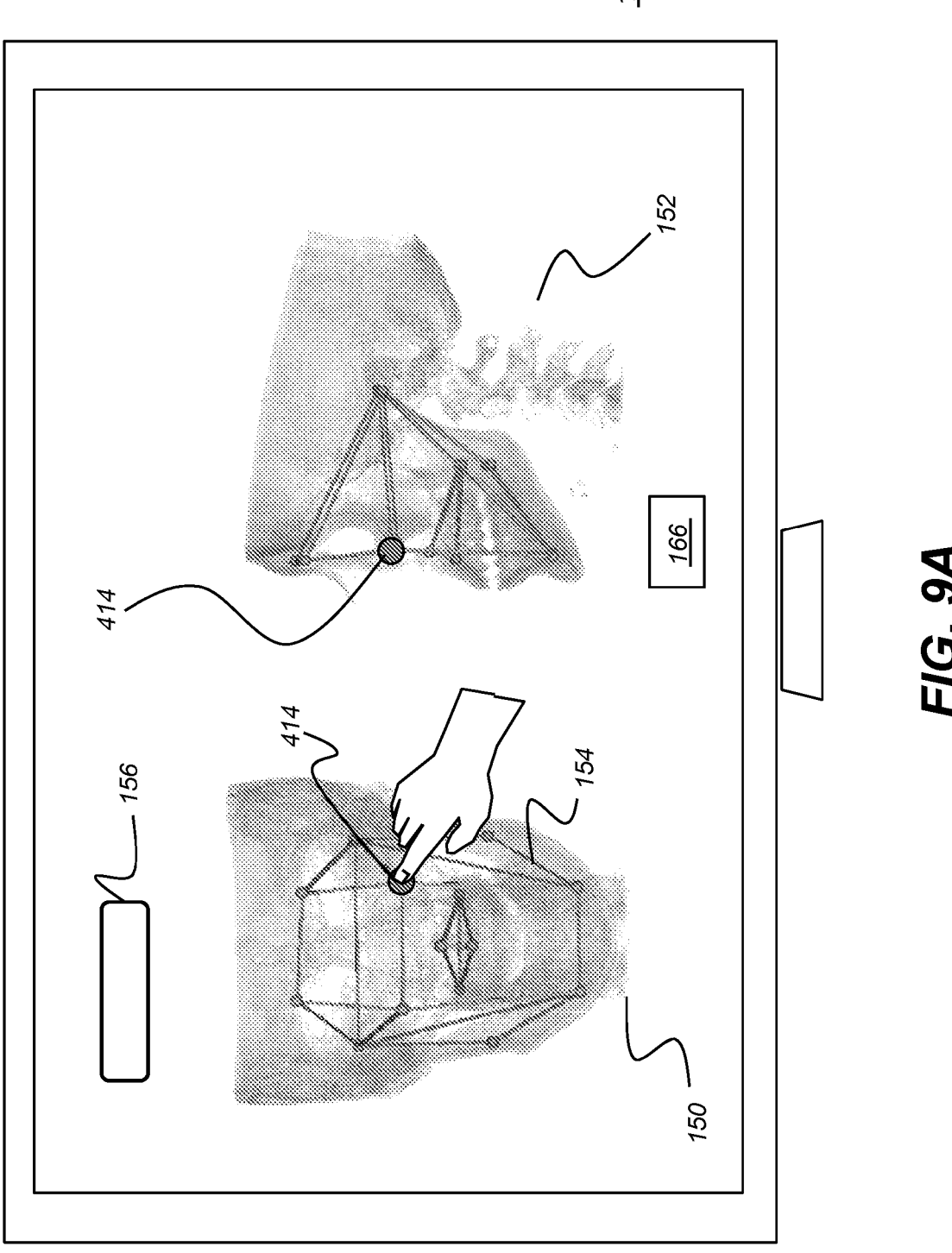
FIGS. 9A, 9B, and 9C show an operator interface for specifying the location of anatomical features using operator-entered reference marks.
Figure 9B:
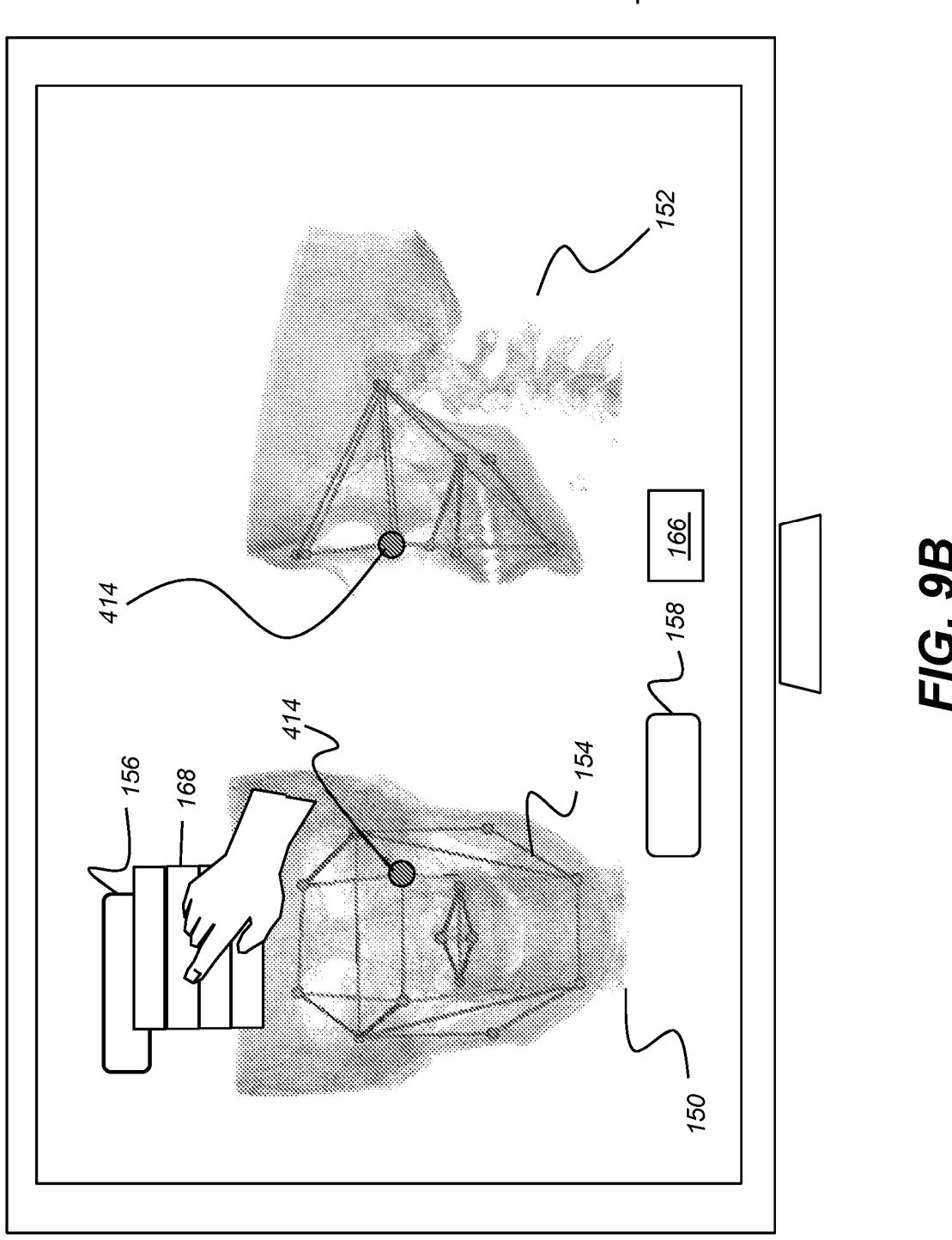
Figure 9C:
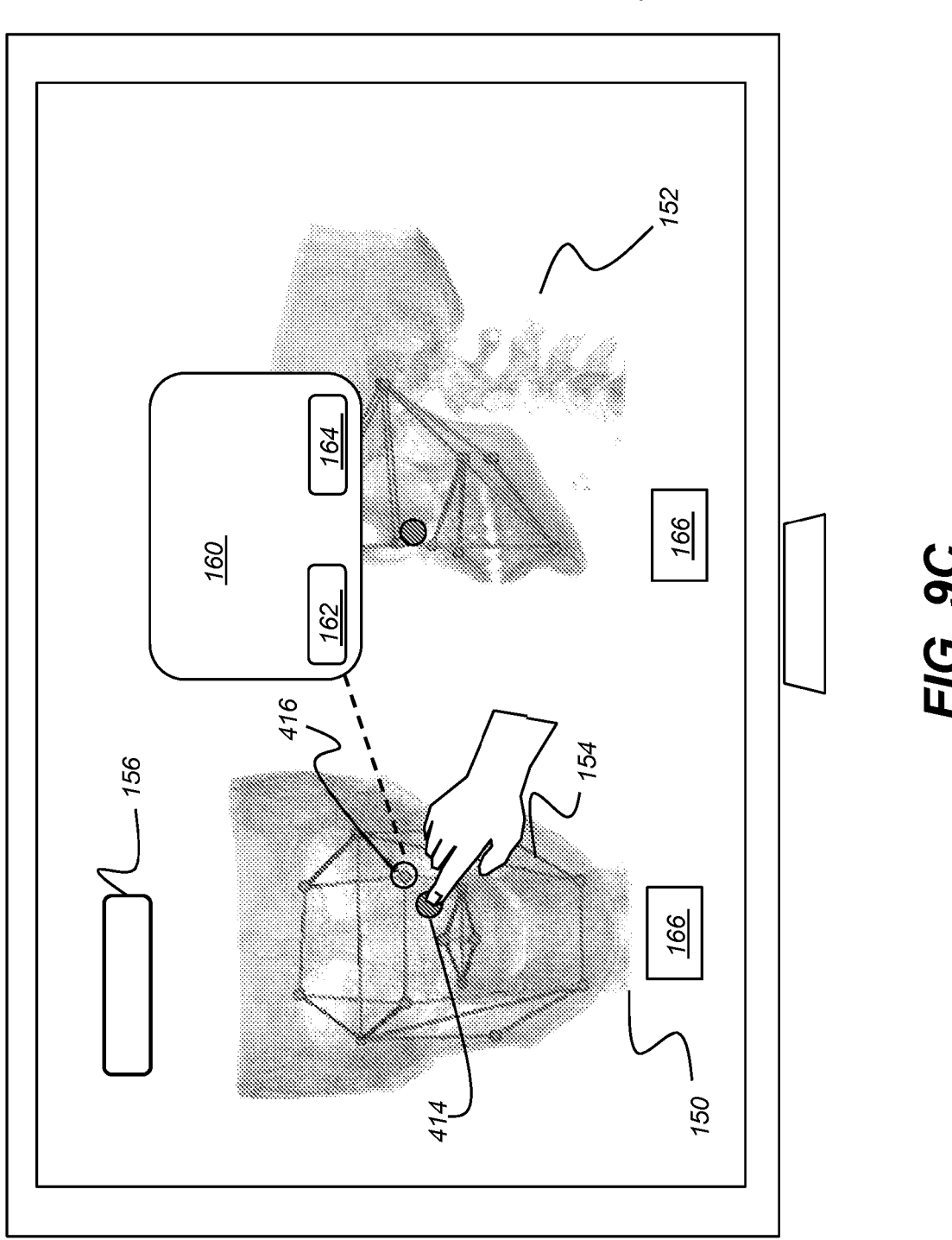

FIGS. 9A, 9B, and 9C show an operator interface appearing on display 108. The operator interface provides, on display 108, an interactive utility for accepting operator instructions and for displaying computation results for cephalometric parameters of a particular patient. Display 108 can be a touch screen display for entry of operator-specified reference marks and other instructions, for example. Display 108 simultaneously displays at least one 2-D view of the volume image data or two or more 2-D views of the volume image data from different angles or perspectives. By way of example, FIG. 9A shows a frontal or coronal view 150 paired with a side or sagittal view 152. More than two views can be shown simultaneously and different 2-D views can be shown, with each of the displayed views independently positioned according to an embodiment of the present disclosure. Views can be mutually orthogonal or may simply be from different angles. As part of the interface of display 108, an optional control 166 enables the viewer to adjust the perspective angle from which one or more of the 2-D views are obtained, either by toggling between alternate fixed views or by changing the relative perspective angle in increments along any of the 3-D axes (x, y, z). A corresponding control 166 can be provided with each 2-D view, as shown in FIG. 9-C. Using the operator interface shown for display 108, each reference mark 414 is entered by the operator using a pointer of some type, which may be a mouse or other electronic pointer or may be a touchscreen entry as shown in FIG. 9A. As part of the operator interface, an optional listing 156 is provided to either guide the operator to enter a specific reference mark according to a prompt, or to identify the operator entry, such as by selection from a drop-down menu 168 as shown in the example of FIG. 9B. Thus, the operator can enter a value in listing 156 or may enter a value in field 158, then select the name associated with the entered value from drop-down menu 168. FIGS. 9A-9C show a framework 154 constructed between reference points. As FIG. 9A shows, each entered reference mark 414 may be shown in both views 150 and 152. A selected reference mark 414 is highlighted on display 108, such as appearing in bold or in another color. A particular reference mark is selected in order to obtain or enter information about the reference mark or to perform some action, such as to shift its position, for example.

In the embodiment shown in FIG. 9B, the reference mark 414 just entered or selected by the operator is identified by selection from a listing 156. For the example shown, the operator selects the indicated reference mark 414, then makes a menu selection such as "infraorbital foramen" from menu 168. An optional field 158 identifies the highlighted reference mark 414. Calculations based on a model or based on standard known anatomical relationships can be used to identify reference mark 414, for example.

FIG. 9C shows an example in which the operator enters a reference mark 414 instruction that is detected by the system as incorrect or unlikely. An error prompt or error message 160 displays, indicating that the operator entry appears to be in error. The system computes a probable location for a particular landmark or anatomical feature based on a model or based on learned data, for example. When the operator entry appears to be inaccurate, message 160 displays, along with an optional alternate location 416. An override instruction 162 is displayed, along with a repositioning instruction 164 for repositioning the reference mark according to the calculated information from the system. Repositioning can be done by accepting another operator entry from the display screen or keyboard or by accepting the system-computed reference mark location, at alternate location 416 in the example of FIG. 9C.

According to an alternate embodiment of the present disclosure, the operator does not need to label reference marks as they are entered. Instead the display prompts the operator to indicate a specific landmark or anatomical feature on any of the displayed 2-D views and automatically labels the indicated feature. In this guided sequence, the operator responds to each system prompt by indicating the position of the corresponding reference mark for the specified landmark.

According to another alternate embodiment of the present disclosure, the system determines which landmark or anatomical feature has been identified as the operator indicates a reference mark; the operator does not need to label reference marks as they are entered. The system computes the most likely reference mark using known information about anatomical features that have already been identified and, alternately, by computation using the dimensions of the reconstructed 3-D image itself.

According to another alternate embodiment of the present disclosure, the system determines or the operator selects a set of "cephalometric parameters" such as reference land-marks or anatomical features or derivatives of said land-marks and features including features derived from the teeth (e.g., from a pull-down menu of various cephalometric parameter sets) and the system (e.g., biometrics analysis engine 3906) can compute the most likely reference mark or anatomical feature location then names and positions each landmark or anatomical feature in the selected cephalomet-ric parameter set by computation using the dimensions of the reconstructed 3-D image itself and later known information about anatomical features that have already been identified.

Using the operator interface shown in the examples of FIGS. 9A-9C, embodiments of the present disclosure pro-vide a practical 3-D cephalometric analysis system that synergistically integrates the skills of the human operator of the system with the power of the computer in the process of 3-D cephalometric analysis. This takes advantage of human skills of creativity, use of heuristics, flexibility, and judg-ment, and combines these with computer advantages, such as speed of computation, capability for accurate and repeat-able processing, reporting and data access and storage capabilities, and display flexibility.

Referring back to the sequence of FIG. 2, derived cepha-lometric parameters are computed in a computation step S108 once a sufficient set of landmarks is entered. FIGS. 10A through 10E show a processing sequence for computing and analyzing cephalometric data and shows how a number of cephalometric parameters are obtained from combined volume image data and anatomical features information according to operator entered instructions and according to segmentation of the dentition elements. According to an embodiment of the present disclosure, portions of the fea-tures shown in FIGS. 10A through 10E are displayed on display 108 (FIG. 1).

Figure 10A:
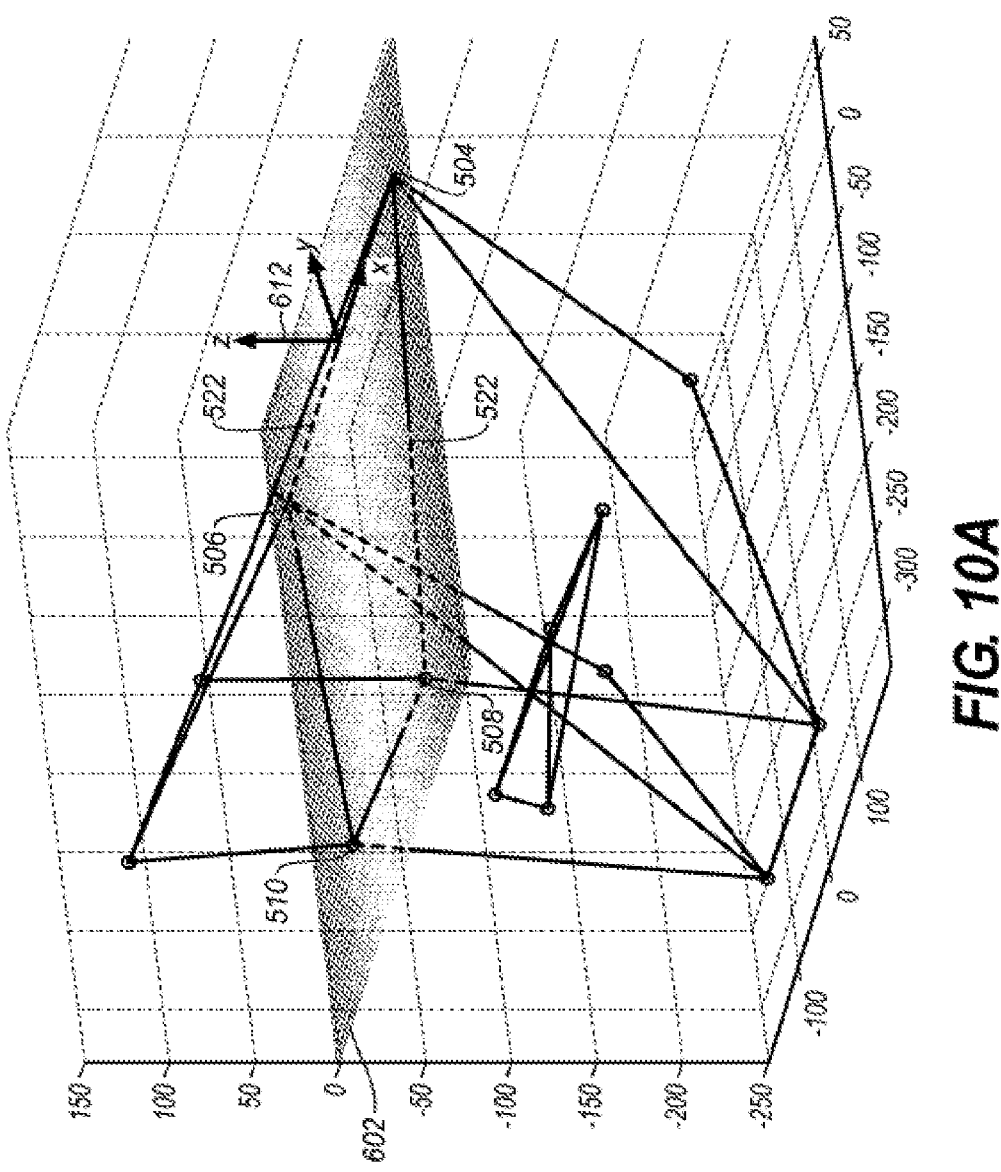
FIGS. 10A, 10B, 10C, 10D, and 10E are graphs that show how various derived parameters are calculated using the volume image data and corresponding operator-entered reference marks.

An exemplary derived cephalometric parameter shown in FIG. 10A is a 3-D plane 602 (termed a t-reference plane in cephalometric analysis) that is computed by using a subset of the set of first geometric primitives with reference marks 504, 506, 508 and 510 as previously described with refer-ence to FIG. 6. A further derived cephalometric parameter is 3-D coordinate reference system 612 termed a t-reference system and described by Treil in publications noted previ-ously. The z axis of the t-reference system 612 is chosen as perpendicular to the 3-D t-reference plane 602. The y axis of the t-reference system 612 is aligned with framework con-necting line 522 between reference marks 508 and 504. The x axis of the t-reference system 612 is in plane 602 and is orthogonal to both z and x axes of the t-reference system. The directions of t-reference system axes are indicated in FIG. 10A and in subsequent FIGS. 10B, 10C, 10D, and 10E. The origin of the t-reference system is at the middle of framework connecting line 522 that connects reference marks 504 and 506.

With the establishment of t-reference system 612, 3-D reference marks from step S106 and 3-D teeth data (3-D position list of a tooth) from step S104 are transformed from the CBCT volume coordinate system to t-reference system 612. With this transformation, subsequent computations of derived cephalometric parameters and analyses can now be performed with respect to t-reference system 612.

Figure 10B:
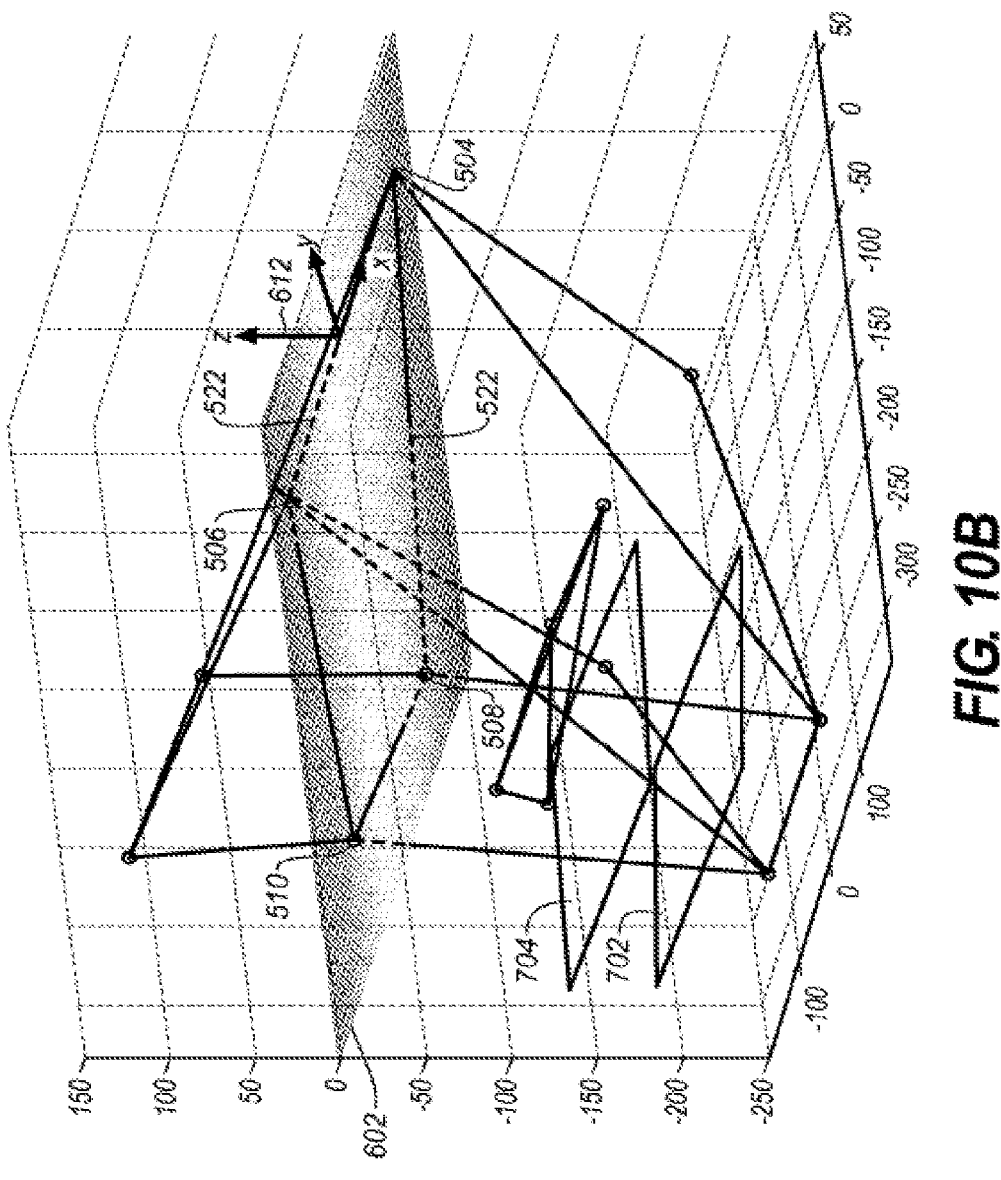

Referring to FIG. 10B, a 3-D upper jaw plane 704 and a 3-D lower jaw plane 702 can be derived from cephalometric parameters from the teeth data in t-reference system 612. The derived upper jaw plane 704 is computed according to teeth data segmented from the upper jaw (maxilla). Using methods familiar to those skilled in cephalometric measurement and analysis, derived lower jaw plane 702 is similarly computed according to the teeth data segmented from the lower jaw (mandibular).

For an exemplary computation of a 3-D plane from the teeth data, an inertia tensor is formed by using the 3-D position vectors and code values of voxels of all teeth in a jaw (as described in the cited publications by Treil); eigen-vectors are then computed from the inertia tensor. These eigenvectors mathematically describe the orientation of the jaw in the t-reference system 612. A 3-D plane can be formed using two of the eigenvectors, or using one of the eigenvectors as the plane normal.

Figure 10C:
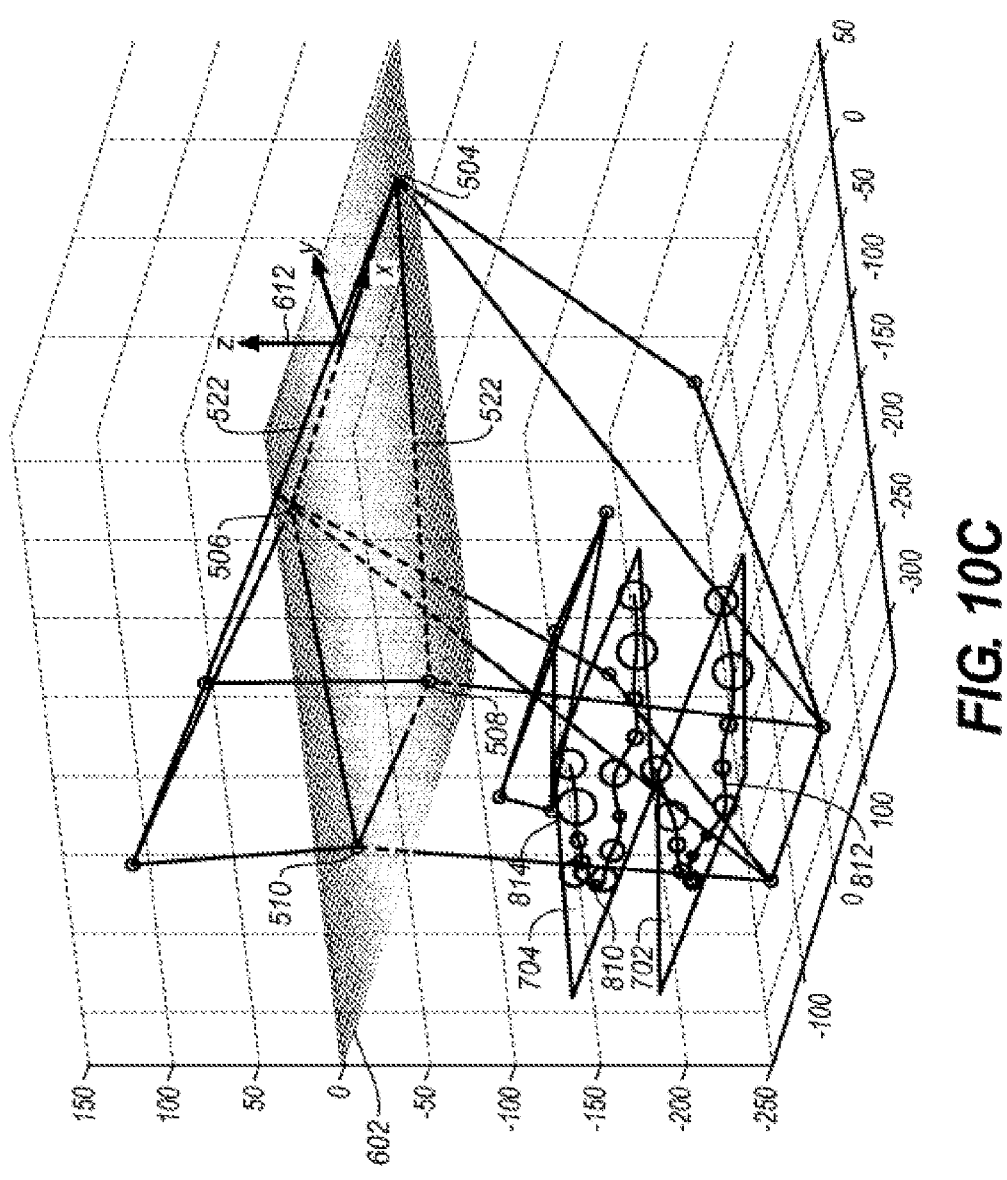

Referring to FIG. 10C, further derived parameters are shown. For each jaw, jaw curves are computed as derived parameters. An upper jaw curve 810 is computed for the upper jaw; a lower jaw curve 812 is derived for the lower jaw. The jaw curve is constructed to intersect with the mass center of each tooth in the respective jaw and to lie in the corresponding jaw plane. The mass center of the tooth can be calculated, in turn, using the 3-D position list and the code value list for the segmented teeth.

The mass of a tooth is also a derived cephalometric parameter computed from the code value list of a tooth. In FIG. 10C, an exemplary tooth mass is displayed as a circle 814 or other type of shape for an upper jaw tooth. According to an embodiment of the present disclosure, one or more of the relative dimensions of the shape, such as the circle radius, for example, indicates relative mass value, the mass value of the particular tooth in relation to the mass of other teeth in the jaw. For example, the first molar of the upper jaw has a mass value larger than the neighboring teeth mass values.

According to an embodiment of the present disclosure, for each tooth, an eigenvector system is also computed. An inertia tensor is initially formed by using the 3-D position vectors and code values of voxels of a tooth, as described in the cited publications by Treil. Eigenvectors are then com-puted as derived cephalometric parameters from the inertia tensor. These eigenvectors mathematically describe the ori-entation of a tooth in the t-reference system.

Figure 10D:
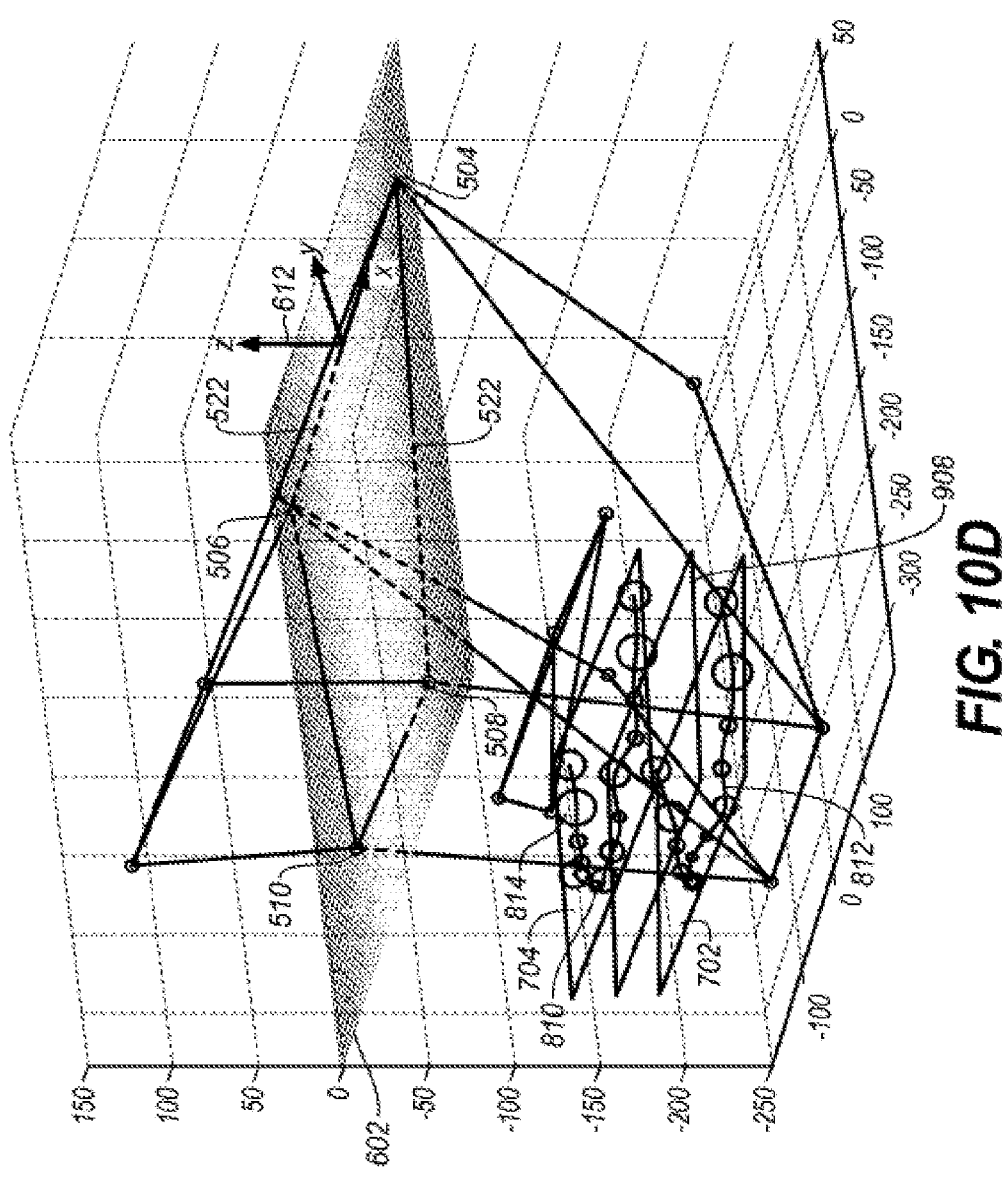

As shown in FIG. 10D, another derived parameter, an occlusal plane, 3-D plane 908, is computed from the two jaw planes 702 and 704. Occlusal plane, 3-D plane 908, lies between the two jaw planes 702 and 704. The normal of plane 908 is the average of the normal of plane 702 and normal of plane 704.

Figure 10E:
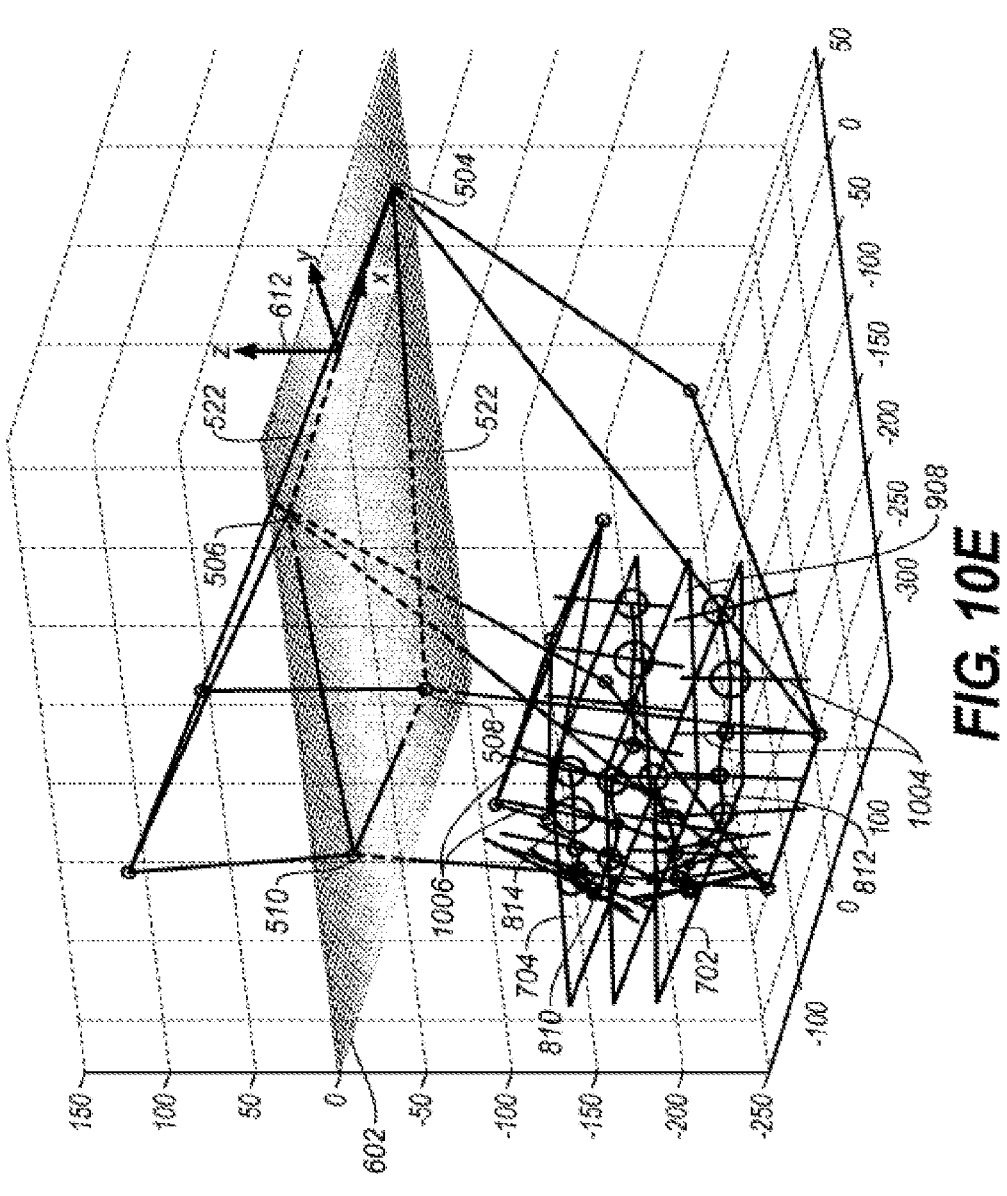

For an individual tooth, in general, the eigenvector cor-responding to the largest computed eigenvalue is another derived cephalometric parameter that indicates the medial axis of the tooth. FIG. 10E shows two types of exemplary medial axes for teeth: medial axes 1006 for upper incisors and medial axes 1004 for lower incisors.

The calculated length of the medial axis of a tooth is a useful cephalometric parameter in cephalometric analysis and treatment planning along with other derived parameters. It should be noted that, instead of using the eigenvalue to set the length of the axis as proposed in the cited publication by Triel, embodiments of the present disclosure compute the actual medial axis length as a derived parameter using a different approach. A first intersection point of the medial axis with the bottom slice of the tooth volume is initially located. Then, a second intersection point of the medial axis with the top slice of the tooth volume is identified. An embodiment of the present disclosure then computes the length between the two intersection points.

Figure 11:
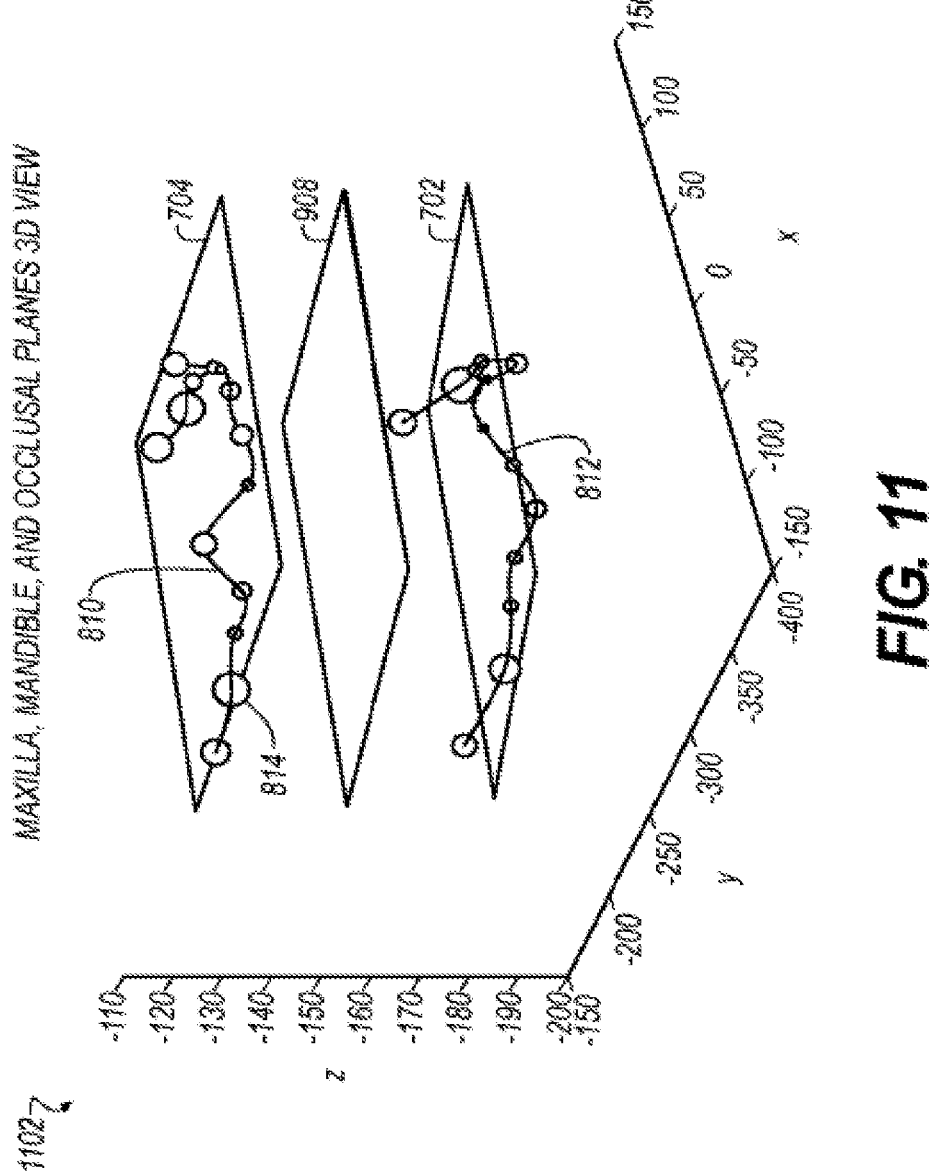
FIG. 11 is a 3-D graph showing a number of derived cephalometric parameters from segmented teeth data.

FIG. 11 shows a graph 1102 that provides a closeup view that isolates the occlusal plane 908 in relation to upper jaw plane 704 and lower jaw plane 702 and shows the relative positions and curvature of jaw curves 810 and 812.

Figure 12:
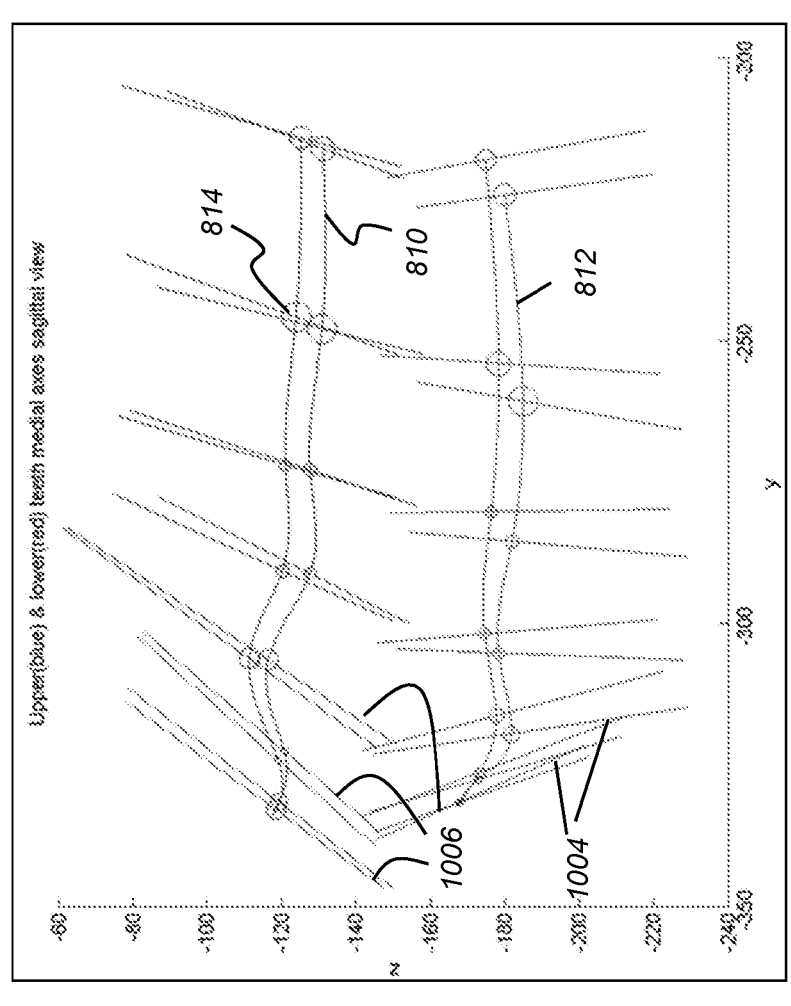
FIG. 12 is a 2-D graph showing the derived cephalometric parameters from segmented teeth data.

FIG. 12 shows a graph 1202 that shows the positional and angular relationships between the upper teeth medial axes 1006 and the lower teeth medial axes 1004.

As noted in the preceding descriptions and shown in the corresponding figures, there are a number of cephalometric parameters that can be derived from the combined volume image data, including dentition element segmentation, and operator-entered reference marks. These are computed in a computer-aided cephalometric analysis step S110 (FIG. 2).

One exemplary 3-D cephalometric analysis procedure in step S110 that can be particularly valuable relates to the relative parallelism of the maxilla (upper jaw) and mandibular (lower jaw) planes 702 and 704. Both upper and lower jaw planes 702 and 704, respectively, are derived parameters, as noted previously. The assessment can be done using the following sequence:

Project the x axis of the maxilla inertia system (that is, the eigenvectors) to the x-z plane of the t-reference system and compute an angle MX1_RF between the z axis of the t-reference system and the projection;

Project the x axis of the mandibular inertia system (that is, the eigenvectors) to the x-z plane of the t-reference system and compute an angle MD1_RF between the z axis of the t-reference system and the projection;

MX1_MD1_RF=MX1_RF−MD1_RF gives a parallelism assessment of upper and lower jaws in the x-z plane of the t-reference system;

Project the y axis of the maxilla inertia system (that is, the eigenvectors) to the y-z plane of the t-reference system and compute the angle MX2_RS between the y axis of the t-reference system and the projection;

Project the y axis of the mandibular inertia system (that is, the eigenvectors) to the y-z plane of the t-reference system and compute an angle MD2_RS between the y axis of the t-reference system and the projection;

MX2_MD2_RS=MX2_RS−MD2_RS gives a parallelism assessment of upper and lower jaws in the y-z plane of the t-reference system.

Another exemplary 3-D cephalometric analysis procedure that is executed in step S110 is assessing the angular property between the maxilla (upper jaw) incisor and mandible (lower jaw) incisor using medial axes 1006 and 1004 (FIGS. 10E, 12). The assessment can be done using the following sequence:

Project the upper incisor medial axis 1006 to the x-z plane of the t-reference system and compute an angle MX1_AF between the z axis of the t-reference system and the projection;

Project the lower incisor medial axis 1004 to the x-z plane of the t-reference system and compute an angle MD1_AF between the z axis of the t-reference system and the projection;

MX1_ MD1_AF=MX1_AF−MD1_AF gives the angular property assessment of the upper and lower incisors in the x-z plane of the t-reference system;

Project the upper incisor medial axis 1006 to the y-z plane of the t-reference system and compute an angle MX2_AS between the y axis of the t-reference system and the projection;

Project the lower incisor medial axis 1004 to the y-z plane of the t-reference system and compute an angle MD2_AS between the y axis of the t-reference system and the projection;

MX2_MD2_AS=MX2_AS−MD2_AS gives the angular property assessment of upper and lower incisors in the y-z plane of the t-reference system.

Figure 13:
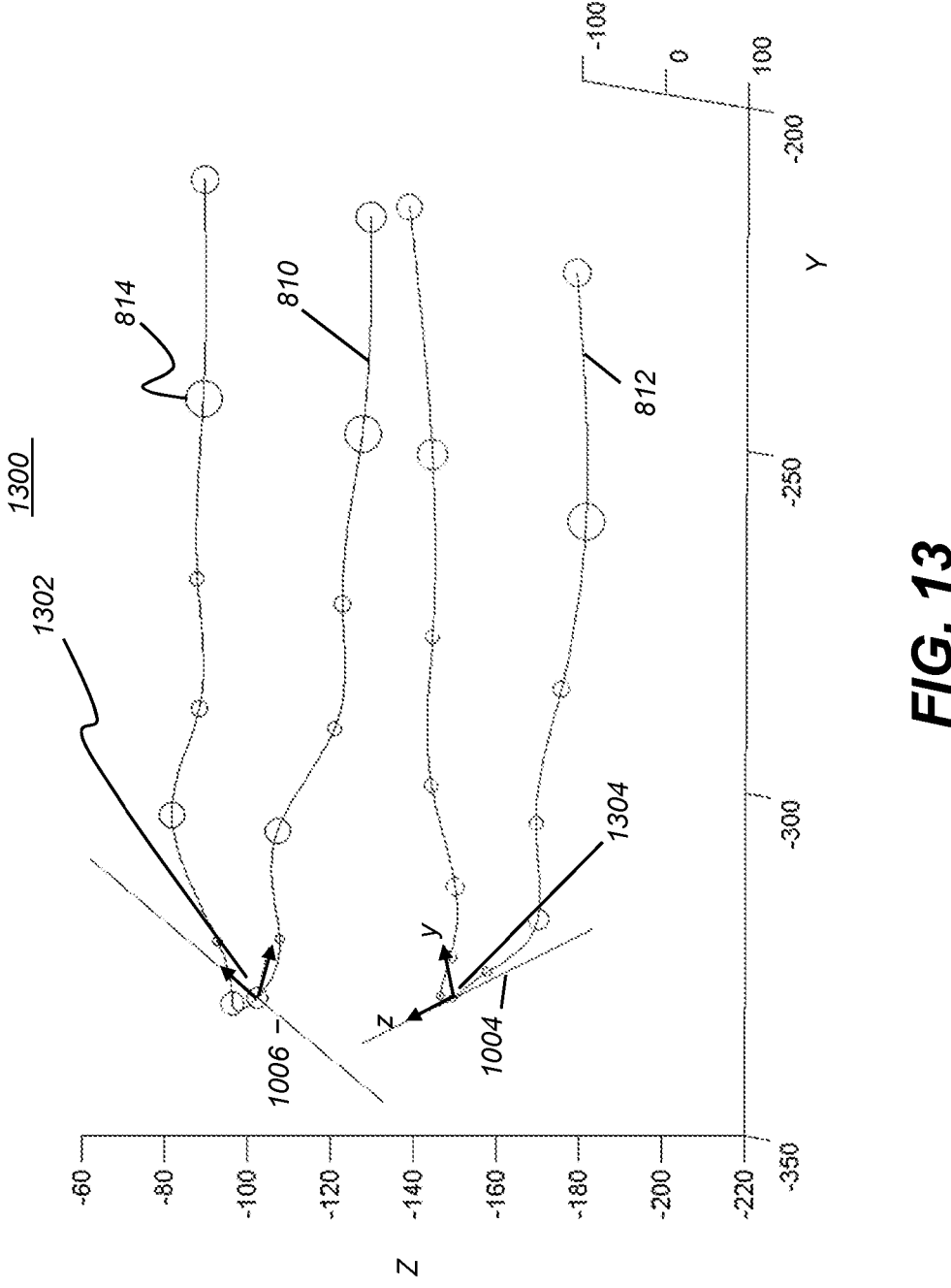
FIG. 13 is another 3-D graph showing the derived cephalometric parameters from segmented teeth data.

FIG. 13 shows a graph 1300 that shows a local x-y-z coordinate system 1302 for an upper incisor, and a local x-y-z coordinate system 1304 for a lower incisor. The local axes of the x-y-z coordinate system align with the eigenvectors associated with that particular tooth. The x axis is not shown but satisfies the right-hand system rule.

In FIG. 13, the origin of system 1302 can be selected at any place along axis 1006. An exemplary origin for system 1302 is the mass center of the tooth that is associated with axis 1006. Similarly, the origin of system 1304 can be selected at any place along axis 1004. An exemplary origin for system 1304 is the mass center of the tooth that is associated with axis 1004.

Figure 14:
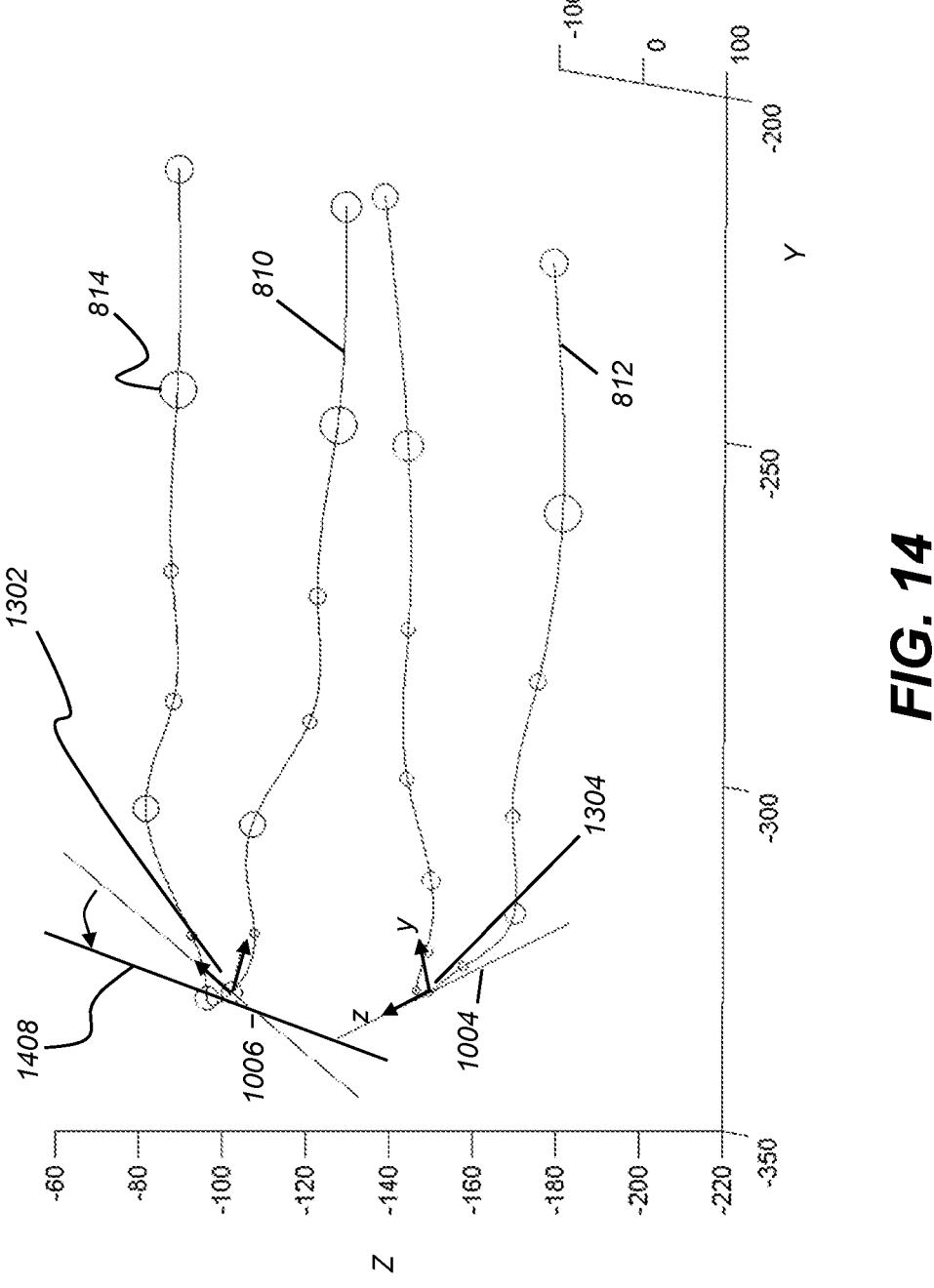
FIG. 14 is a graph showing the derived cephalometric parameters from segmented teeth data and treatment parameter.

Based on the analysis performed in Step S110 (FIG. 2), an adjustment or treatment plan is arranged in a planning step S112. An exemplary treatment plan is to rotate the upper incisor counter clockwise at a 3-D point, such as at its local coordinate system origin, and about an arbitrary 3-D axis, such as about the x axis of the local x-y-z system. The graph of FIG. 14 shows rotation to an axis position 1408.

In a treatment step S114 of FIG. 2, treatment is performed based on the planning, for example, based on upper incisor rotation. The treatment planning can be tested and verified visually in a visualization step S116 before the actual treatment takes place.

Referring back to FIG. 2, there is shown a line 120 from Step S114 to Step S102. This indicates that there is a feedback loop in the sequence 200 workflow. After the patient undergoes treatment, an immediate evaluation or, alternately, a scheduled evaluation of the treatment can be performed by entering relevant data as input to the system. Exemplary relevant data for this purpose can include results from optical, radiographic, MRI, or ultrasound imaging and/or any meaningful related measurements or results.

Figure 15:
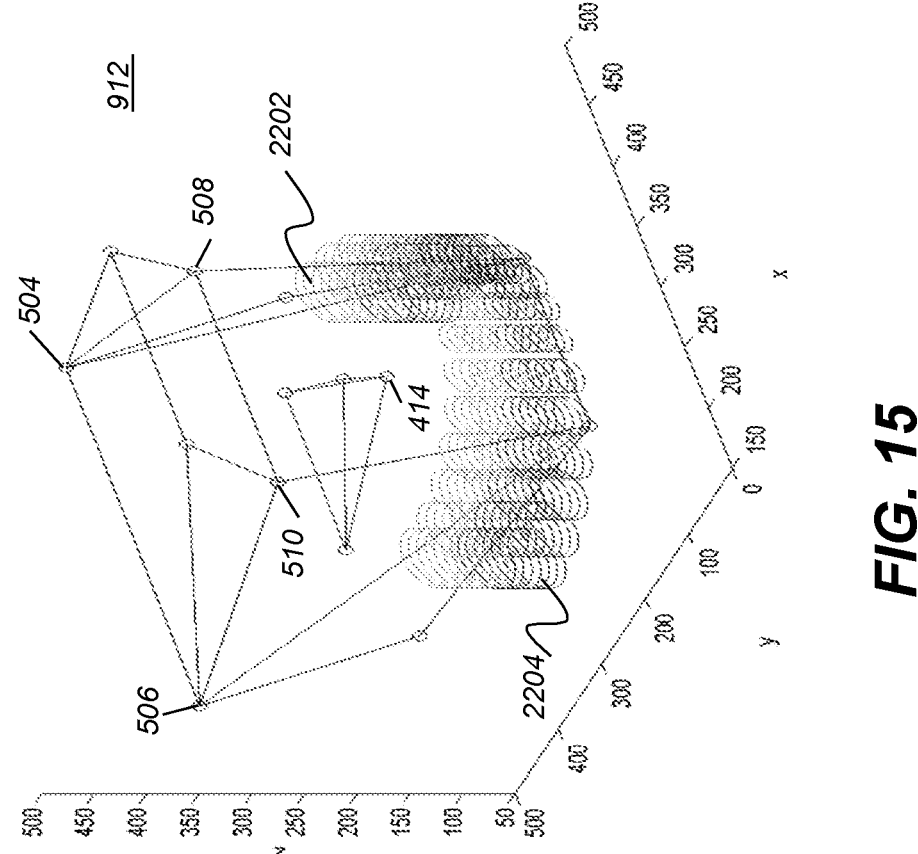
FIG. 15 is a 3-D graph that shows how tooth exclusion is learned by the system.

An optional tooth exclusion step S124 is also shown in sequence 200 of FIG. 2. For example, if the patient has had one or more teeth removed, then the teeth that complement the removed teeth can be excluded. For this step, the operator specifies one or more teeth, if any, to be excluded from the rest of the processing steps based on Treil's theory of jaw planes parallelism. The graph of FIG. 15 shows how tooth exclusion can be learned by the system, using a virtual or digital phantom 912. Digital phantom 912 is a virtual model used for computation and display that is constructed using a set of landmarks and a set of upper teeth of a digital model of an upper jaw and a set of lower teeth of a digital model of a lower jaw. Digital phantom 912 is a 3-D or volume image data model that is representative of image data that is obtained from patient anatomy and is generated using the landmark and other anatomical information provided and can be stored for reference or may be generated for use as needed. The use of various types of digital phantom is well known to those skilled in the digital radiography arts. The landmarks such as reference marks 504, 506, 508 and 510 of the digital phantom 912 correspond to the actual reference marks identified from the CBCT volume 202 (FIG. 3). These landmarks are used to compute the t-reference system 612 (FIGS. 10A-10E).

The operator can exclude one or more teeth by selecting the teeth from a display or by entering information that identifies the excluded teeth on the display.

In the FIG. 15 representation, the upper and lower teeth, such as digital teeth 2202 and 2204 of digital phantom 912 are digitally generated. The exemplary shape of a digital tooth is a cylinder, as shown. The exemplary voxel value for a digital tooth in this example is 255. It can be appreciated that other shapes and values can be used for phantom 912 representation and processing.

Figure 16B:
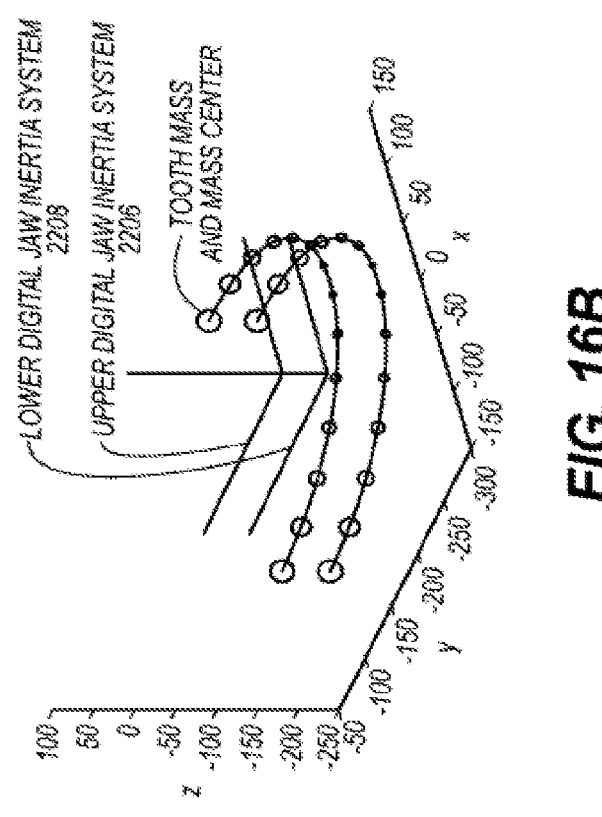
FIG. 16B is a 3-D graph showing computed axes of inertia systems for upper and lower jaws.
Figure 16A:
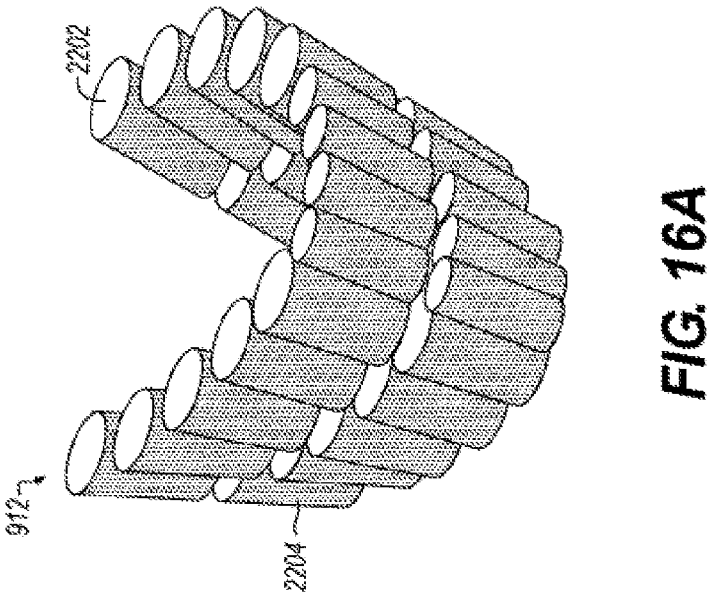
FIG. 16A is a perspective view that shows teeth of a digital phantom.

FIG. 16A shows digital teeth 2202 and 2204 of digital phantom 912. The corresponding digital teeth in the upper digital jaw and lower digital jaw are generated in a same way, with the same size and same code value.

To assess parallelism of the upper and lower digital jaws, an inertia tensor for each digital jaw is formed by using the 3-D position vectors and code values of voxels of all digital teeth in a digital jaw (see the Treil publications, cited previously). Eigenvectors are then computed from the inertia tensor. These eigenvectors, as an inertial system, mathematically describe the orientation of the jaw in the t-reference system 612 (FIG. 10A). As noted earlier, the eigenvectors, computed from the inertial tensor data, are one type of derived cephalometric parameter.

Figure 17B:
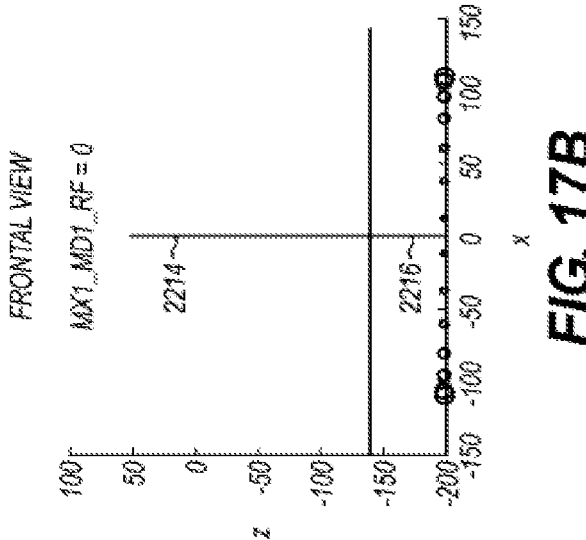
FIG. 17B is a graph showing parallelism for specific tooth structures.
Figure 17A:
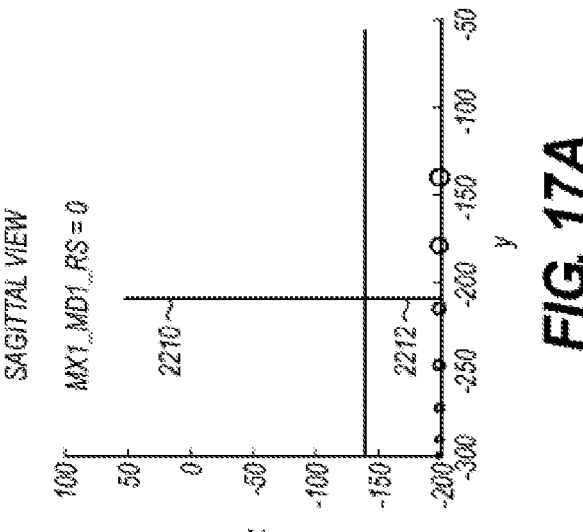
FIG. 17A is a graph showing parallelism for specific tooth structures.

As shown in FIG. 16B, the computed axes of an upper digital jaw inertia system 2206 and a lower digital jaw inertia system 2208 are in parallel for the generated digital phantom 912 as expected, since the upper and lower jaw teeth are created in the same way. FIG. 17A shows this parallelism in the sagittal view along a line 2210 for the upper jaw and along a line 2212 for the lower jaw; FIG. 17B shows parallelism in the frontal (coronal) view at a line 2214 for the upper jaw and at a line 2216 for the lower jaw.

Figures 18A, 18B:
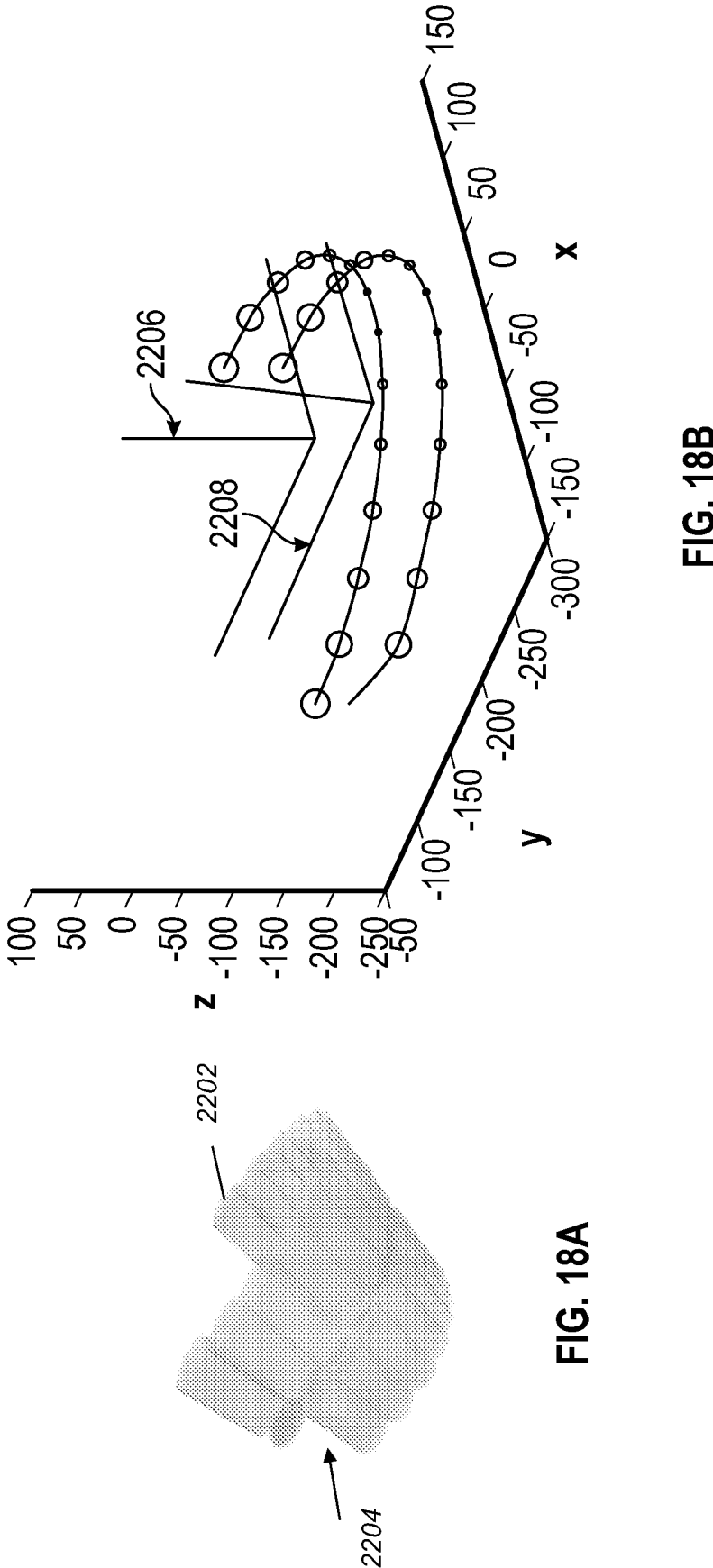
FIG. 18A is a perspective view that shows teeth of a digital phantom with a tooth missing.
FIG. 18B is a graph showing computed axes of inertia systems for upper and lower jaws for the example of FIG. 18A.
Figure 19B:
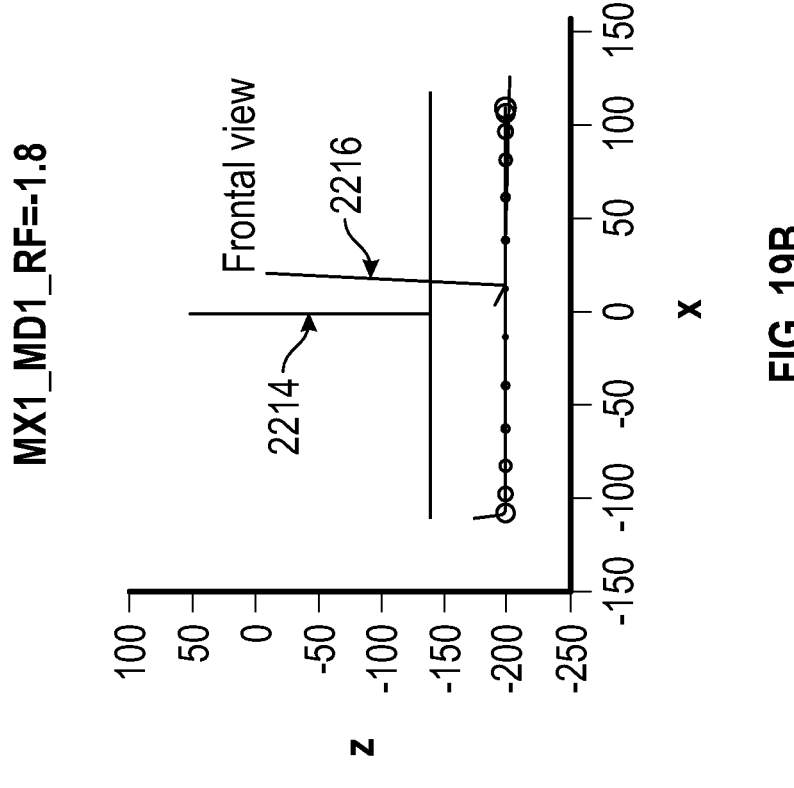
FIG. 19B is a graph showing lack of parallelism for specific tooth structures.
Figure 19A:
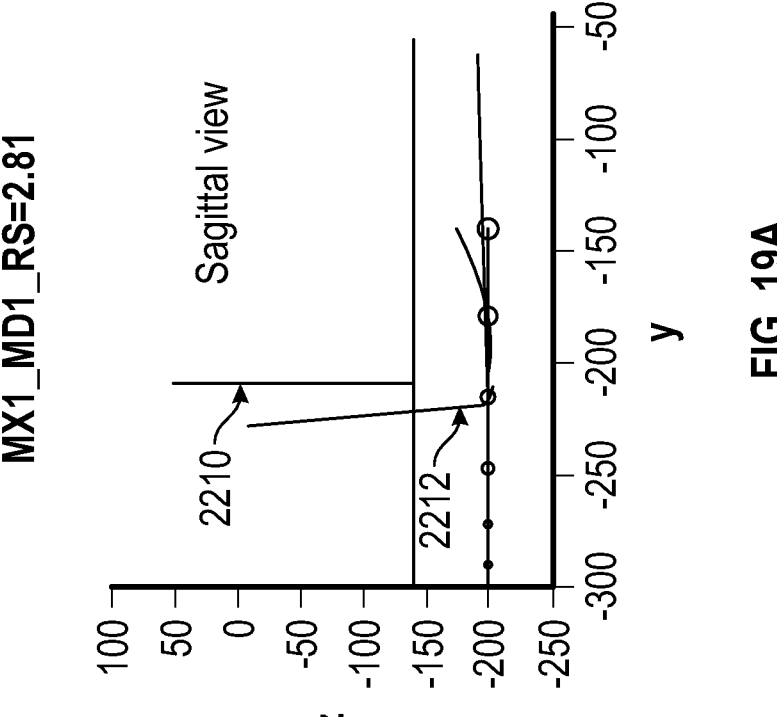
FIG. 19A is a graph showing lack of parallelism for specific tooth structures.
Figures 20A, 20B:
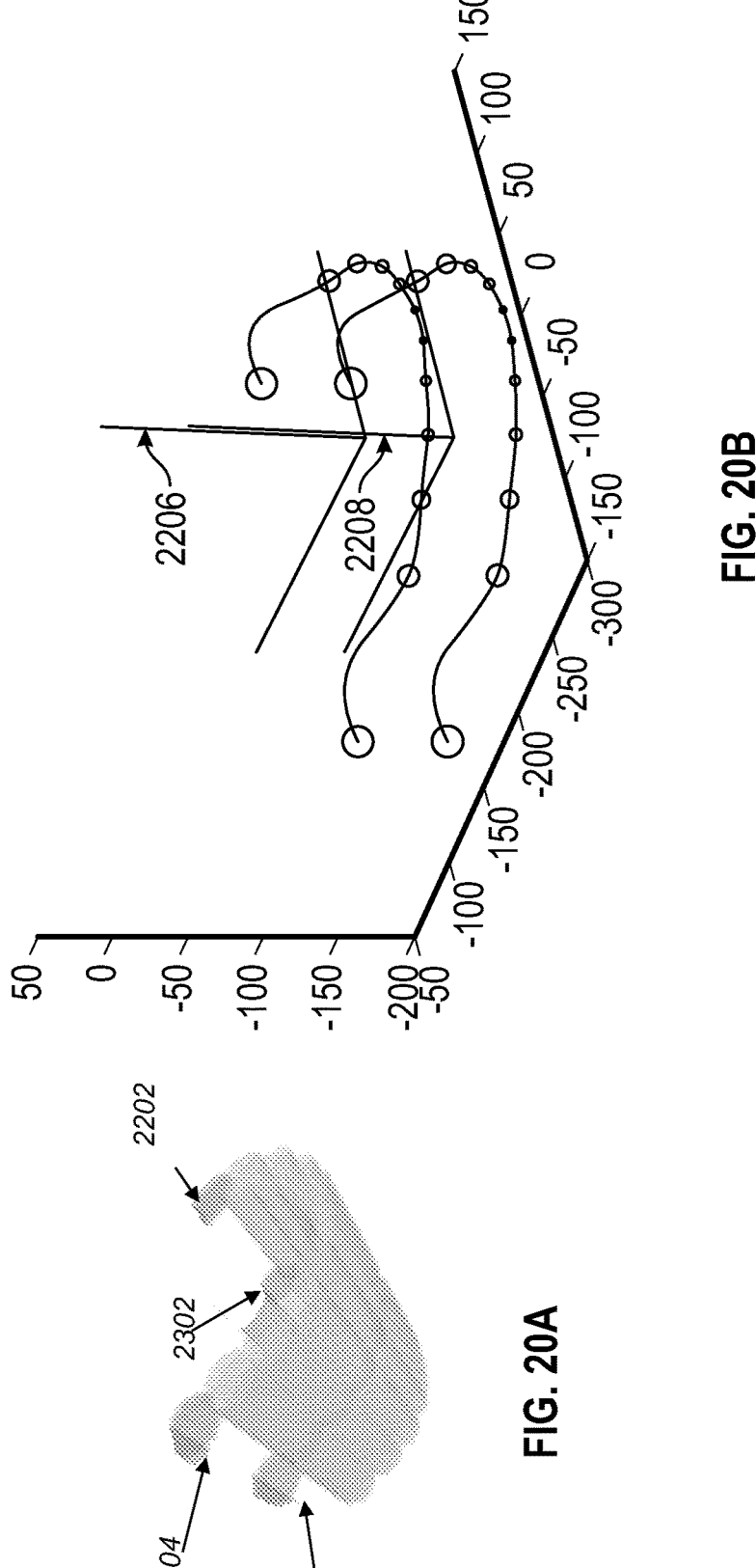
FIG. 20A is a perspective view that shows teeth of a digital phantom with tooth exclusion.
FIG. 20B is a graph showing computed axes of inertia systems for upper and lower jaws for the example of FIG. 20A.

Referring to FIGS. 18A and 18B, there is shown a case in which digital tooth 2204 is missing. The computed axes of upper digital jaw inertia system 2206 and lower digital jaw inertia system 2208 are no longer in parallel. In corresponding FIGS. 19A and 19B, this misalignment can also be examined in a sagittal view along a line 2210 for the upper jaw and a line 2212 for the lower jaw; in the frontal view along a line 2214 for the upper jaw and a line 2216 for the lower jaw. According to an embodiment of the present disclosure, this type of misalignment of upper and lower jaw planes (inertia system) due to one or more missing teeth can be corrected by excluding companion teeth of each missing tooth as illustrated in FIGS. 20A and 20B. The companion teeth for tooth 2204 are teeth 2304, 2302 and 2202. Tooth 2304 is the corresponding tooth in the upper jaw for tooth 2204. Teeth 2202 and 2302 are the corresponding teeth at the other side for the teeth 2304 and 2204. After excluding the companion teeth for the missing tooth 2204, the computed axes of inertia system 2206 for the upper jaw and inertia system 2208 for the lower jaw are back in parallel.

Figures 21A, 21B:
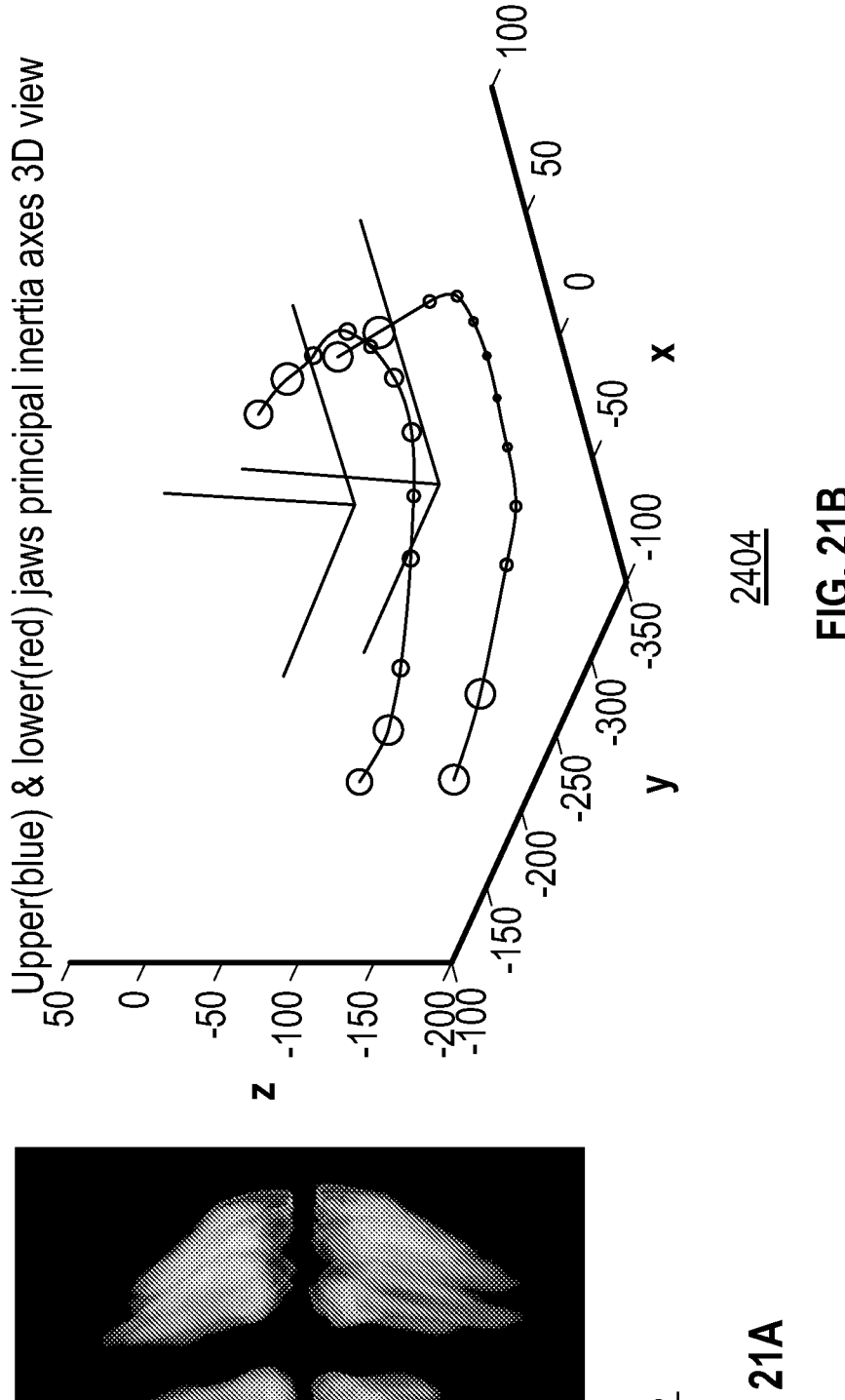
FIG. 21A is an example showing tooth exclusion for a missing tooth.
FIG. 21B is a graph showing computed axes of inertia systems for upper and lower jaws for the example of FIG. 21A.

FIGS. 21A and 21B illustrate segmented teeth from a CBCT volume in a case where companion teeth are excluded for a missing tooth. The segmentation results are shown in an image 2402. The computed axes of inertia systems for the upper and lower jaws are in parallel as demonstrated in a graph 2404.

Figure 22A:
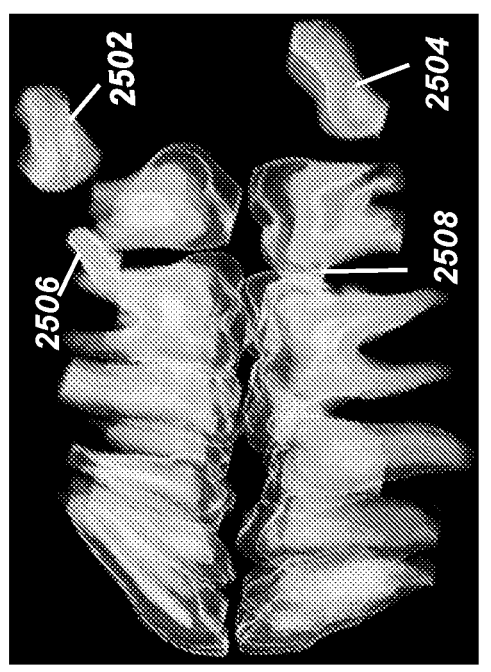
FIG. 22A is an example showing tooth exclusion for a missing tooth.
Figure 22B:
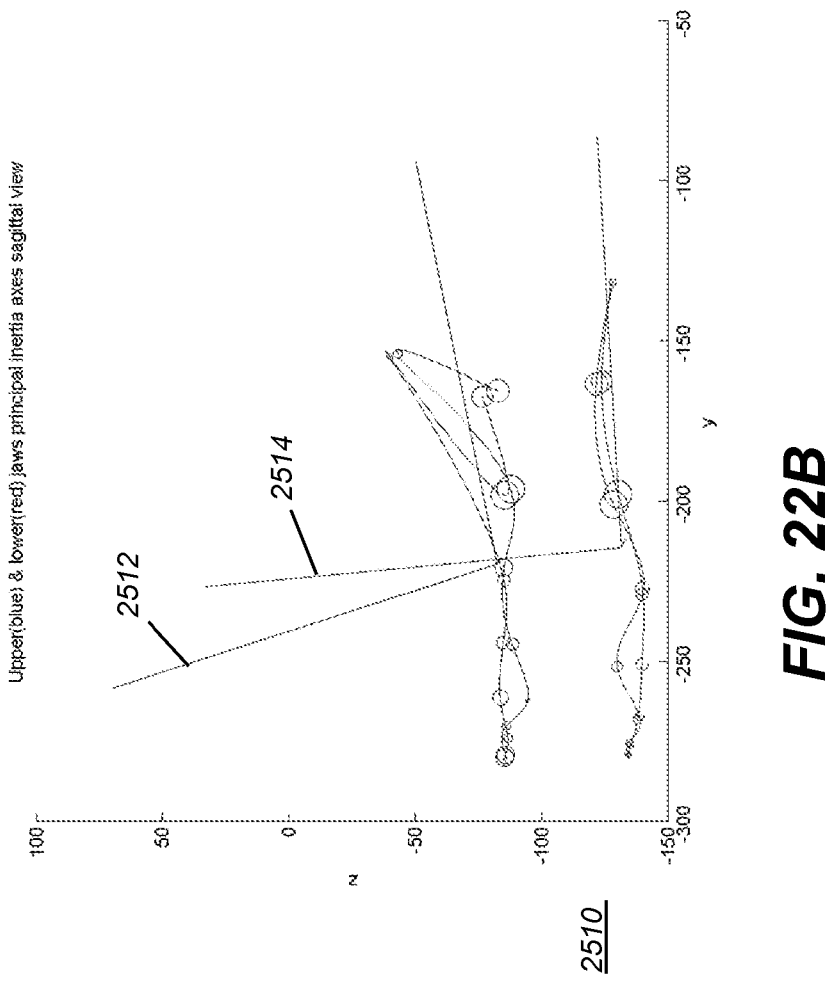
FIG. 22B is a graph showing computed axes of inertia systems for upper and lower jaws for the example of FIG. 22A.

FIGS. 22A and 22B show the method of exclusion of companion teeth applied to another patient using tooth exclusion step S124 (FIG. 2). As shown in an image 2500, teeth 2502, 2504, 2506 and 2508 are not fully developed. Their positioning, size, and orientation severely distort the physical properties of the upper jaw and lower jaw in terms of inertia system computation. A graph 2510 in FIG. 22B depicts the situation where upper jaw inertia system 2512 and lower jaw inertia system 2514 are severely misaligned (not in parallel).

Figures 23A, 23B:
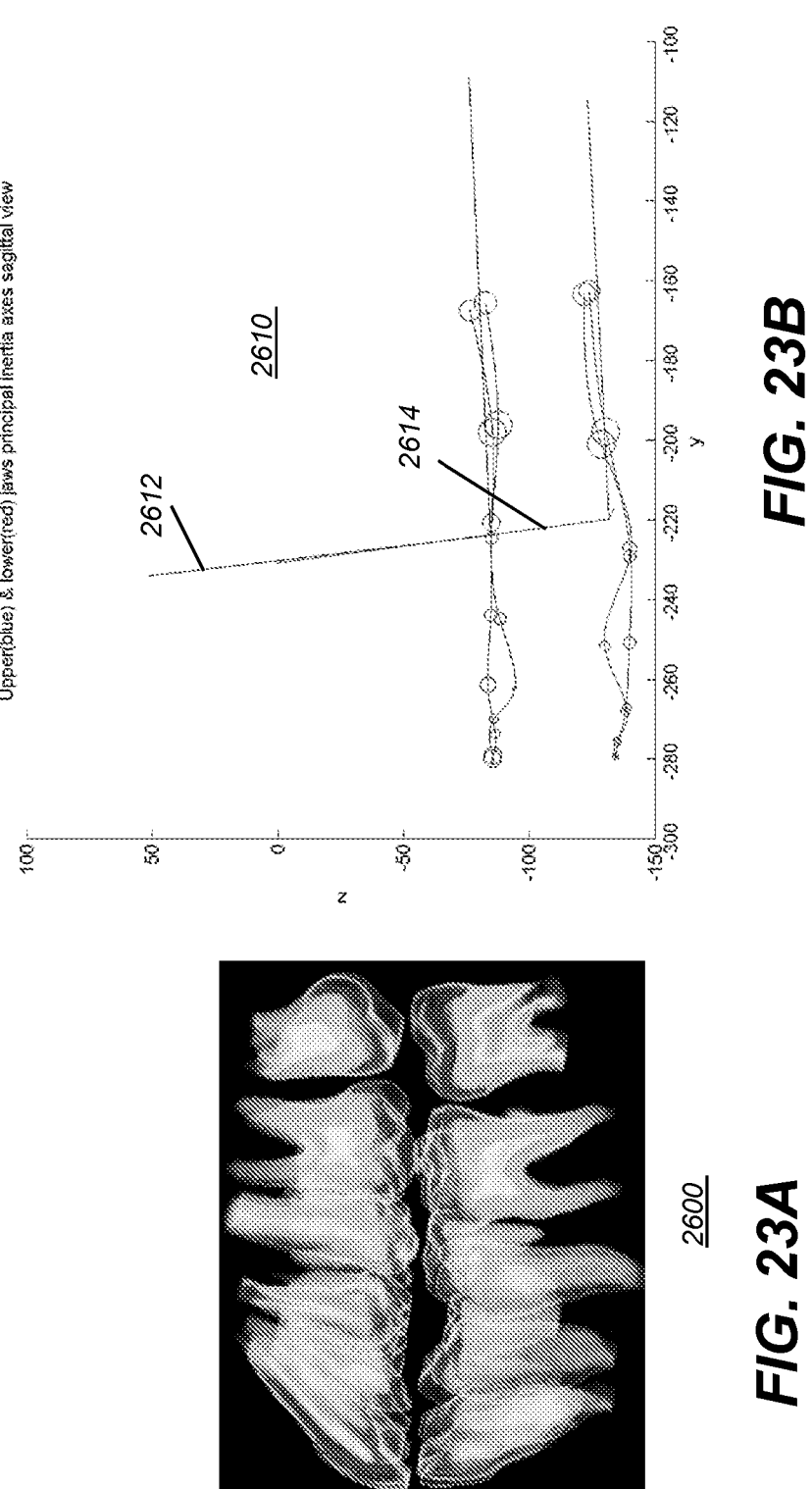
FIG. 23A is an image that shows the results of excluding specific teeth.
FIG. 23B is a graph showing computed axes of inertia systems for upper and lower jaws for the example of FIG. 23A.

FIGS. 23A and 23B show the results of excluding specific teeth from the image. An image 2600 shows the results of excluding teeth 2502, 2504, 2506 and 2508 from image 2500 of FIG. 22A. Without the disturbance of these teeth, the axes of inertia system 2612 of the upper jaw and inertia system 2614 lower jaw of the teeth shown in image 2600 are in parallel as depicted in a graph 2610.

Biometry Computation

Given the entered landmark data for anatomic reference points, segmentation of dentition elements such as teeth, implants, and jaws and related support structures, and the computed parameters obtained as described previously, detailed biometry computation can be performed and its results used to assist setup of a treatment plan and monitoring ongoing treatment progress. Referring back to FIG. 8, the biometry computation described subsequently gives more details about step S250 for analyzing and displaying parameters generated from the recorded reference marks.

Figure 24:
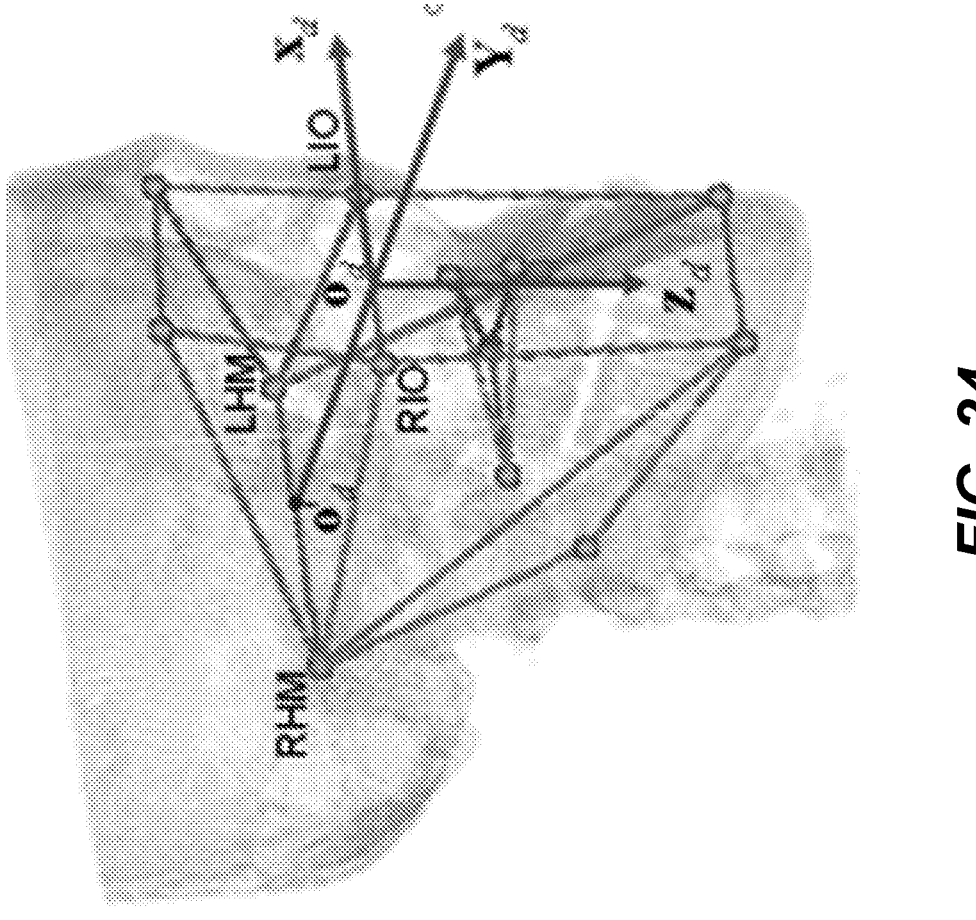
FIG. 24 shows a number of landmarks and coordinate axes or vectors of the DOL reference system.

According to an embodiment of the present disclosure, the entered landmarks and computed inertia systems of teeth are transformed from the original CBCT image voxel space to an alternate reference system, termed the direct orthogonal landmark (DOL) reference system, with coordinates ($x_d$, $y_d$, $z_d$). FIG. 24 shows a number of landmarks and coordinate axes or vectors of the DOL reference system. Landmarks RIO and LIO indicate the infraorbital foramen; landmarks RHM and LHM mark the malleus. The origin $o_d$ of ($x_d$, $y_d$, $z_d$) is selected at the middle of the line connecting landmarks RIO and LIO. Vector $x_d$ direction is defined from landmark RIO to LIO. A YZ plane is orthogonal to vector $x_d$ at point $o_d$. There is an intersection point $o'_d$ of plane YZ and the line connecting RHM and LHM. Vector $y_d$ direction is from $o'_d$ to $o_d$. Vector $z_d$ is the cross product of $x_d$ and $y_d$.

Figure 26:
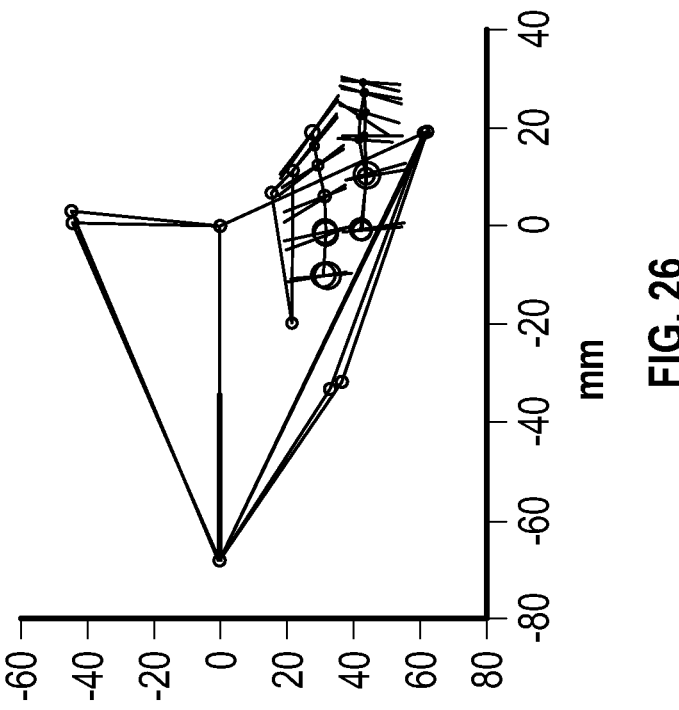
FIG. 26 shows, from a side view, an example with transformed teeth inertia systems using this re-mapping.
Figure 25:
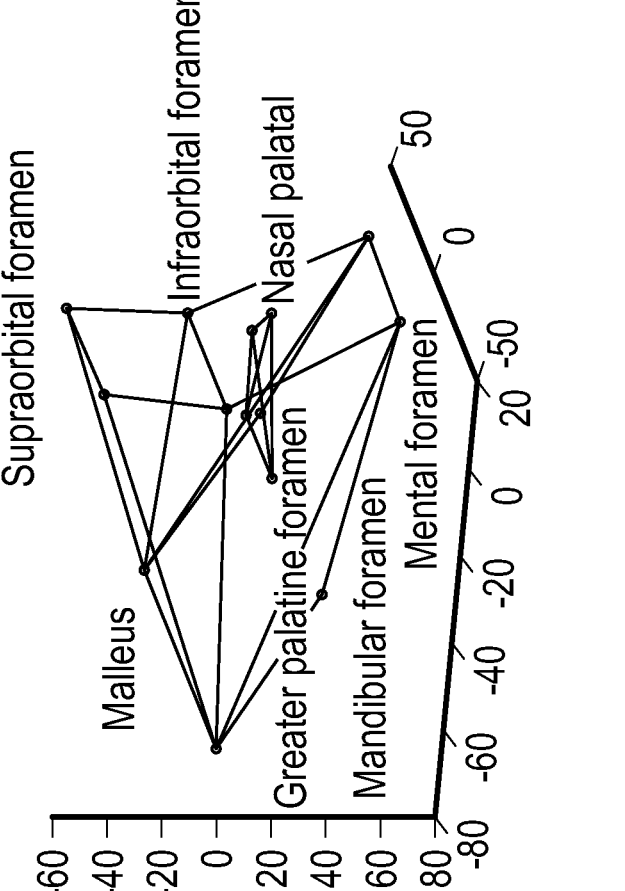
FIG. 25 shows landmark remapping to the alternate space of the DOL reference system.

Using this transformation, the identified landmarks can be re-mapped to the coordinate space shown in FIG. 25. FIG. 26 shows, from a side view, an example with transformed inertia systems using this re-mapping.

By way of example, and not of limitation, the following listing identifies a number of individual data parameters that can be calculated and used for further analysis using the transformed landmark, dentition segmentation, and inertial system data.

A first grouping of data parameters that can be calculated using landmarks in the transformed space gives antero-posterior values:

1. Antero-posterior.alveolar.GIM-Gim: y position difference between the mean centers of inertia of upper and lower incisors.
2. Antero-posterior.alveolar.GM-Gm: difference between the mean centers of inertia of upper and lower teeth.
3. Antero-posterior.alveolar.TqIM: mean torque of upper incisors.
4. Antero-posterior.alveolar.Tqim: mean torque of lower incisors.
5. Antero-posterior.alveolar.(GIM+Gim)/2: average y position of GIM and Gim.
6. Antero-posterior.basis.MNP-MM: y position difference between mean nasal palatal and mean mental foramen.
7. Antero-posterior.basis.MFM-MM: actual distance between mean mandibular foramen and mean mental foramen.
8. Antero-posterior.architecture.MMy: y position of mean mental foramen.
9. Antero-posterior.architecture.MHM-MM: actual distance between mean malleus and mean mental foramen.

A second grouping gives vertical values:

10. Vertical.alveolar.Gdz: z position of inertial center of all teeth.

11. Vertical.alveolar.MxII-MdII: difference between the angles of second axes of upper and lower arches.

12. Vertical.basis.<MHM-MIO,MFM-MM>: angle difference between the vectors MHM-MIO and MFM-MM.

13. Vertical. architecture.MMz: z position of mean mental foramen.

14. Vertical. architecture.13: angle difference between the vectors MHM-MIO and MHM-MM.

Transverse values are also provided:

15. Transverse.alveolar.dM-dm: difference between upper right/left molars distance and lower right/left molars distance 16. Transverse.alveolar.TqM-Tqm: difference between torque of upper $1^{st}$ & $2^{nd}$ molars and torque of lower $1^{st}$ & $2^{nd}$ molars.

17. Transverse.basis.(RGP-LGP)/(RFM-LFM): ratio of right/left greater palatine distance and mandibular foramen distance.

18. Transverse.architecture.(RIO-LIO)/(RM-LM): ratio of right/left infraorbital foramen and mental foramen distances.

Other calculated or "deduced" values are given as follows:

19. Deduced.hidden.GIM: mean upper incisors y position.

20. Deduced.hidden.Gim: mean lower incisors y position.

21. Deduced.hidden.(TqIM+Tqim)/2: average of mean torque of upper incisors and mean torque of lower incisors.

22. Deduced.hidden.TqIM−Tqim: difference of mean torque of upper incisors and mean torque of lower incisors.

23. Deduced.hidden.MNPy: mean nasal palatal y position.

24. Deduced.hidden.GIM-MNP(y): difference of mean upper incisors y position and mean nasal palatal y position.

25. Deduced.hidden.Gim-MM(y): mean mental foramen y position.

26. Deduced.hidden.Gdz/(MMz-Gdz): ratio between value of Gdz and value of MMz-Gdz.

It should be noted that this listing is exemplary and can be enlarged, edited, or changed in some other way within the scope of the present disclosure.

In the exemplary listing given above, there are 9 parameters in the anterior-posterior category, 5 parameters in the vertical category and 4 parameters in the transverse category. Each of the above categories, in turn, has three types: alveolar, basis, and architectural. Additionally, there are 8 deduced parameters that may not represent a particular spatial position or relationship but that are used in subsequent computation. These parameters can be further labeled as normal or abnormal.

Normal parameters have a positive relationship with anterior-posterior disharmony, that is, in terms of their values:

Class III<Class I<Class II.

wherein Class I values indicate a normal relationship between the upper teeth, lower teeth and jaws or balanced bite; Class II values indicate that the lower first molar is posterior with respect to the upper first molar; Class III values indicate that the lower first molar is anterior with respect to the upper first molar.

Abnormal parameters have a negative relationship with anterior-posterior disharmony, that is, in terms of their bite-related values:

Class II<Class I<Class III.

Embodiments of the present disclosure can use an analysis engine in order to compute sets of probable conditions that can be used for interpretation and as guides to treatment planning. FIGS. 27-38 show various aspects of analysis engine operation and organization and some of the text, tabular, and graphical results generated by the analysis engine. It should be noted that a computer, workstation, or host processor can be configured as an analysis engine according to a set of preprogrammed instructions that accomplish the requisite tasks and functions.

Figure 27:
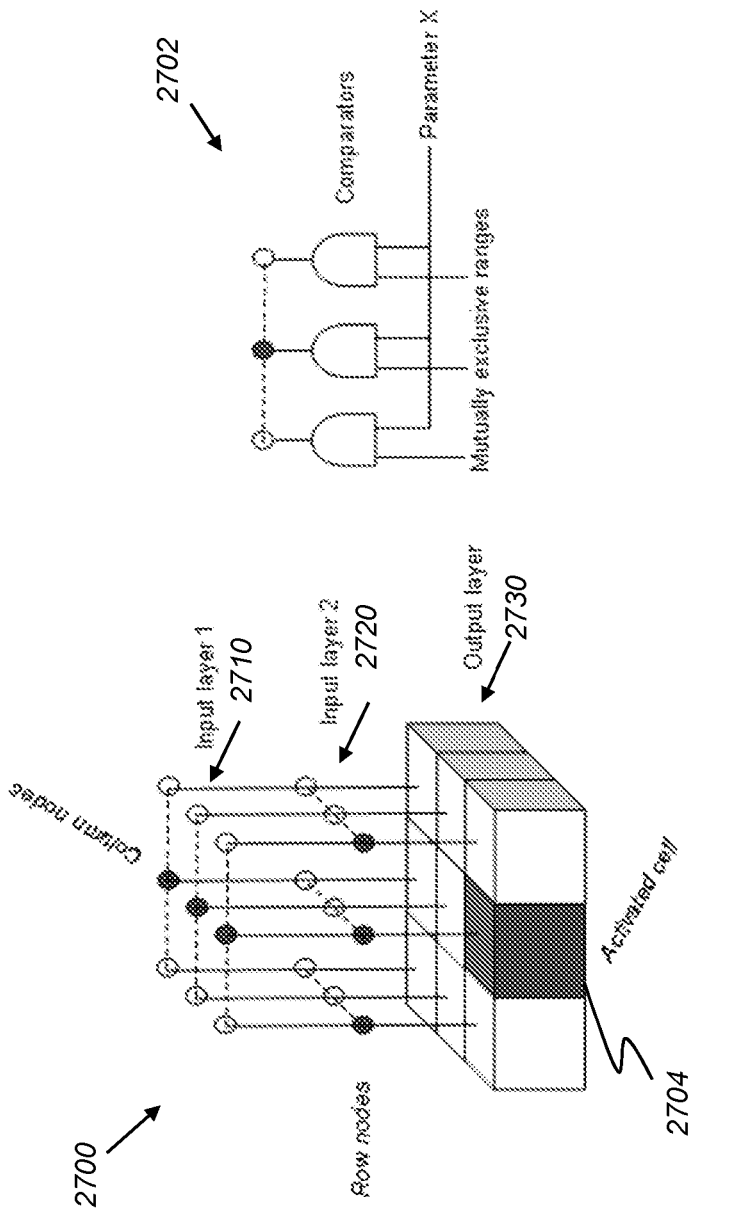
FIG. 27 is a schematic diagram that shows an independent network for the analysis engine according to an embodiment of the present disclosure.

According to an embodiment of the present disclosure, an analysis engine can be modeled as a three-layer network 2700 as shown in FIG. 27. In this model, row and column node inputs can be considered to be directed to a set of comparators 2702 that provide a binary output based on the row and column input signals. One output cell 2704 is activated for each set of possible input conditions, as shown. In the example shown, an input layer 1 2710 is fed with one of the 26 parameters listed previously and an input layer 2 2720 is fed with another one of the 26 parameters. An output layer 2730 contains 9 cells each one of which represents one probable analysis if the two inputs meet certain criterion, that is, when their values are within particular ranges.

According to an embodiment of the present disclosure, the analysis engine has thirteen networks. These include independent networks similar to that shown in FIG. 27 and coupled networks 2800 and 2810 as shown in FIG. 28.

An algorithm shown in FIG. 29 describes the operation of an independent analysis network, such as that shown in the example of FIG. 27. Here, values x and y are the input parameter values; m represents the network index; D(i,j) is the output cell. The steps of "evaluate vector $c_m$" for column values and "evaluate vector $r_m$" for row values check to determine what evaluation criterion the input values meet. For example, in the following formula, if $-\infty < x_m \leq \mu_{x_m}$ then $c_m = $ [true, false, false].

Figure 28:
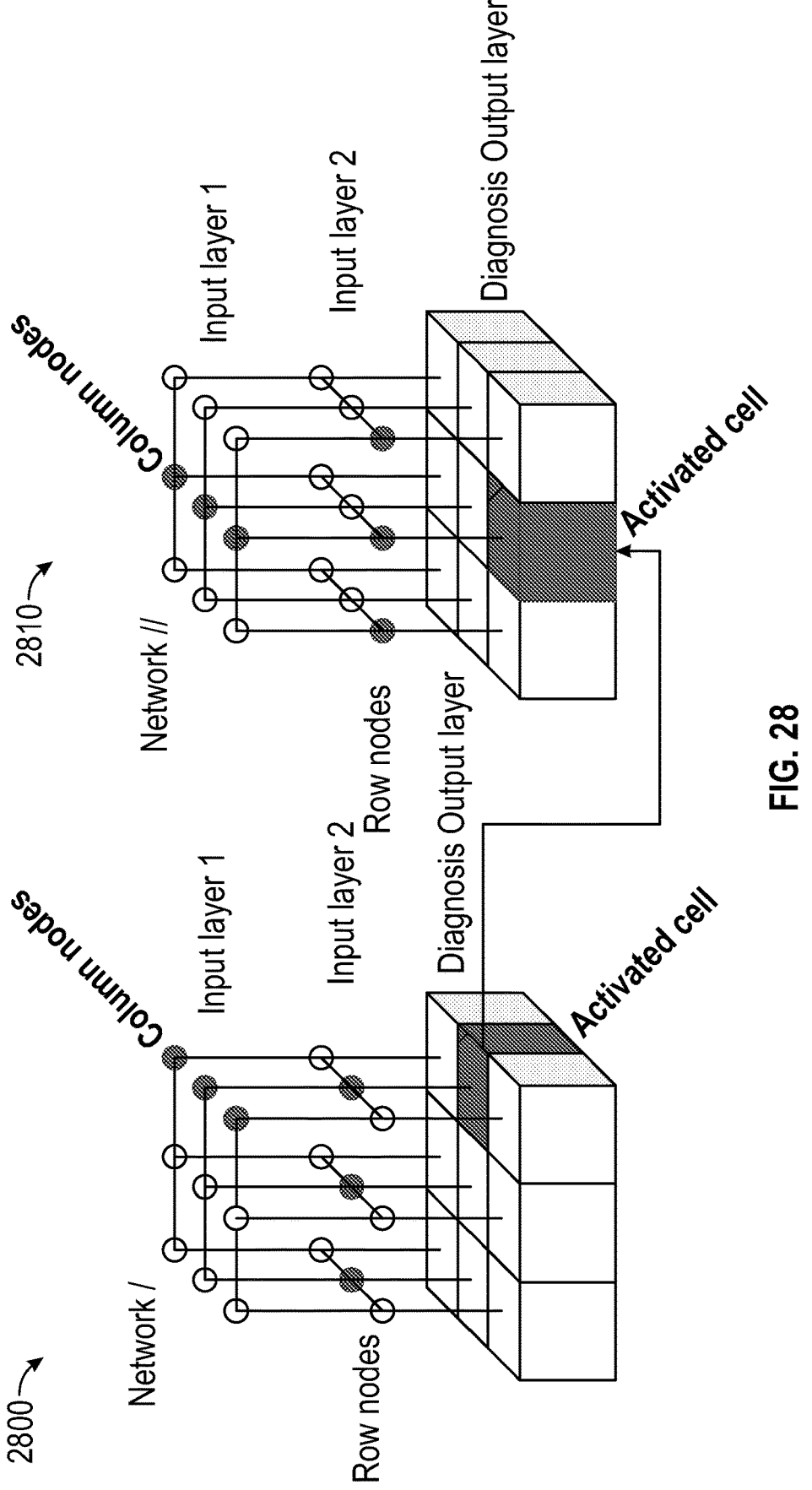
FIG. 28 is a schematic diagram that shows a dependent or coupled network for the analysis engine according to an embodiment of the present disclosure.

The coupled network of FIG. 28 combines results from two other networks and can operate as described by the algorithm in FIG. 30. Again, values x and y are the input values; m represents the network index; D(i,j) is the output cell. The steps of "evaluate vector $c_k$" for column values and "evaluate vector $r_k$" for row values check to determine what evaluation criterion the input values meet.

In a broader aspect, the overall arrangement of networks using the independent network model described with reference to FIG. 27 or the coupled network model described with reference to FIG. 28 allow analysis to examine, compare, and combine various metrics in order to provide useful results that can be reported to the practitioner and used for treatment planning.

Figure 31B:
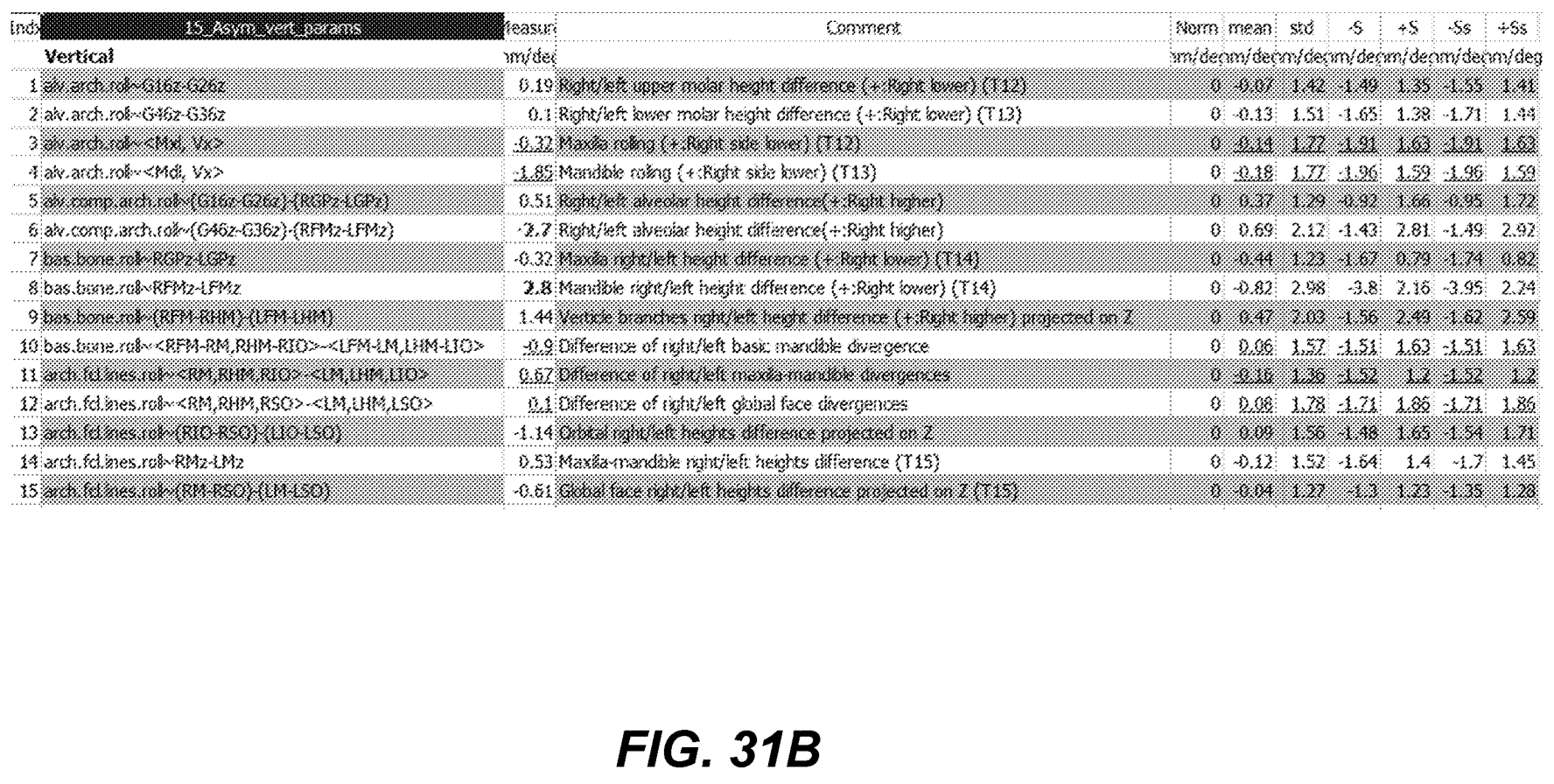

FIG. 31A lists, for a particular patient, example parameters as numerical values and their interpretation with respect mainly to malocclusion of teeth, based on the listing of 26 parameters given previously. FIGS. 31B, 31C and 31D list, for a particular patient, example parameters as numerical values and their interpretation with respect to maxilofacial asymmetry, based on the listing of total 63 parameters given in an exemplary embodiment of this application. FIG. 32A shows exemplary tabulated results 3200 for a particular example with bite analysis and arches angle characteristics. In the example of FIG. 32A, the columns indicate an underjet, normal incisors relation, or overjet condition. Rows represent occlusal classes and arches angle conditions. As FIG. 32A shows, highlighting can be used to accentuate the display of information that indicates an abnormal condition or other condition of particular interest. For the particular patient in the FIG. 32A example, analysis indicates, as a result, an underjet condition with Class III bite characteristics. This result can be used to drive treatment planning, depending on severity and practitioner judgment.

FIG. 32B shows exemplary tabulated results 3200 for another example with analysis of torque for upper and lower incisors, using parameters 3 and 4 from the listing given previously.

FIG. 32C shows exemplary tabulated results 3200 for another example with assessment of biretrusion or biprotrusion using calculated parameters given earlier as parameters (5) and (21).

FIG. 32D shows an exemplary summary listing of results for cephalometric analysis of a particular patient. The listing that is shown refers to analysis indications taken relative to parameters 1-26 listed previously. In the particular example of FIG. 32D, there are 13 results for parameter comparisons using biometric parameters and dentition information derived as described herein. Additional or fewer results could be provided in practice. FIG. 32E shows a detailed listing for one of the conditions reported in a tabular listing with a table 3292 with cells 3294 as shown subsequently (FIG. 35A).

Results information from the biometry computation can be provided for the practitioner in various different formats. Tabular information such as that shown in FIGS. 31A-32E can be provided in file form, such as in a comma-separated value (CSV) form that is compatible for display and further calculation in tabular spreadsheet arrangement, or may be indicated in other forms, such as by providing a text message. A graphical display, such as that shown in FIG. 26, can alternately be provided as output, with particular results highlighted, such as by accentuating the intensity or color of the display for features where measured and calculated parameters show abnormal biometric relations, such as overjet, underjet, and other conditions.

The computed biometric parameters can be used in an analysis sequence in which related parameters are processed in combination, providing results that can be compared against statistical information gathered from a patient population. The comparison can then be used to indicate abnormal relationships between various features. This relationship information can help to show how different parameters affect each other in the case of a particular patient and can provide resultant information that is used to guide treatment planning. In one embodiment, the resultant information can be reported in an exemplary format shown in FIG. 35A. In another embodiment, the resultant information can be reported in an exemplary format shown in FIG. 46.

Referring back to FIG. 1, memory 132 can be used to store a statistical database of cephalometric information gathered from a population of patients. Various items of biometric data that provides dimensional information about teeth and related supporting structures, with added information on bite, occlusion, and interrelationships of parts of the head and mouth based on this data can be stored from the patient population and analyzed. The analysis results can themselves be stored, providing a database of predetermined values capable of yielding a significant amount of useful information for treatment of individual patients. According to an embodiment of the present disclosure, the parameter data listed in FIGS. 31A and 31B are computed and stored for each patient, and may be stored for a few hundred patients or for at least a statistically significant group of patients. The stored information includes information useful for determining ranges that are considered normal or abnormal and in need of correction. Then, in the case of an individual patient, comparison between biometric data from the patient and stored values calculated from the database can help to provide direction for an effective treatment plan.

As is well known to those skilled in the orthodontic and related arts, the relationships between various biometric parameters measured and calculated for various patients can be complex, so that multiple variables must be computed and compared in order to properly assess the need for corrective action. The analysis engine described in simple form with respect to FIGS. 27 and 28 compares different pairs of parameters and provides a series of binary output values. In practice, however, more complex processing can be performed, taking into account the range of conditions and values that are seen in the patient population.

Highlighting particular measured or calculated biometric parameters and results provides useful data that can guide development of a treatment plan for the patient.

Figure 33:
FIG. 33 shows a system display with a recommendation message based on analysis results.
Figure 34:
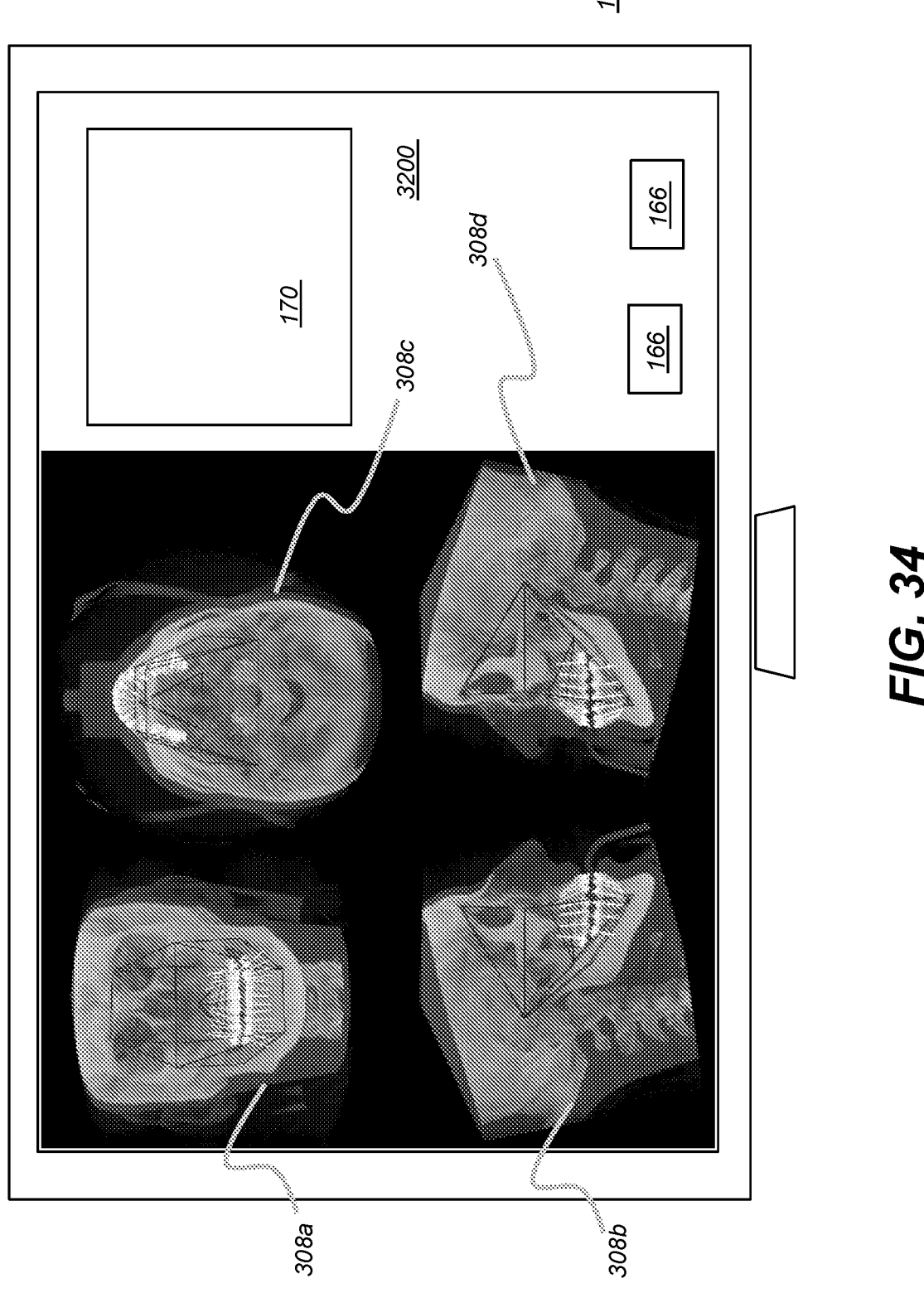
FIG. 34 shows a system display with a graphical depiction to aid analysis results.

FIG. 33 shows a system display of results 3200 with a recommendation message 170 based on analysis results and highlighting features of the patient anatomy related to the recommendation. FIG. 34 shows a system display 108 with a graphical depiction of analysis results 3200. Annotated 3-D views (e.g., 308a-308d) are shown, arranged at different angles, along with recommendation message 170 and controls 166.

Certain exemplary method and/or apparatus embodiments according to the present disclosure can address the need for objective metrics and displayed data that can be used to help evaluate asymmetric facial/dental anatomic structure. Advantageously, exemplary method and/or apparatus embodiments present measured and analyzed results displayed in multiple formats suitable for assessment by the practitioner.

FIG. 35A shows an exemplary text report for maxillofacial/dental asymmetry assessment according to an embodiment of the present disclosure. The report lists a set of assessment tables (T1-T19) available from the system, with cell entries (denoted by C with row and column indices, C(row, column)) providing maxillofacial/dental structural asymmetry property assessment comments organized based on the calculations related to relationships between obtained parameters, such as parameters P1-P15 in FIG. 31B. An exemplary assessment table 3292 is depicted in FIG. 32E, having four rows and four columns.

In one embodiment, for each exemplary assessment table (e.g., 19 assessment tables), only one cell 3294 can be activated at a time; the activated cell content is highlighted, such as by being displayed in red font. In the exemplary table 3292, the activated cell is C(2,2) (3294) with a content "0" indicating that asymmetry is not found for the property of incisors and molars upper/lower deviations.

For a quick reference to the exemplary assessment tables, the system of the present disclosure generates a checklist type concise summary page (e.g., FIG. 35A) that provides information with respect to table numbers (Tn), parameter numbers (Pk, j), cell indices (Cs, t), and actual assessment comments from assessment tables T1-T19. The information obtained from this type of text report can be helpful for the practitioner, providing at least some objective metrics that can be useful in developing a treatment plan for a particular patient or evaluating treatment progress. Further beneficial to the practitioner can be cumulative summative evaluations directed to overall condition assessments of a patient. This can be the situation, in particular, when numbers of conditional reference points and relationships therebetween utilized to determine asymmetric facial/dental anatomic structures or relationships for a patient involve large numbers of view-oriented and 3D-oriented treatment conditions, with variable underlying causes.

In one exemplary asymmetric determination table embodiment, 19 assessment tables can be included with hundreds of reference points and several hundreds of relationships therebetween. In this exemplary asymmetric determination table embodiment, tables include:

T1: Asymmetric matching incisors and molars upper/lower deviations;

T2: Arch rotation;

T3: Upper/lower arch right rotation and upper or lower arch responsibility;

T4: Asymmetric matching incisors upper/lower deviations with upper inc transverse deviation, response of upper or lower arch in the upper/lower incisors trans deviation;

T5: Asymmetric matching incisors upper/lower deviations with anterior bases transverse deviation, response of upper or lower arch anterior deviation in the upper/lower incisors trans deviation;

T6: Asymmetric matching incisors upper/lower molar deviations with upper molars transverse deviation, response of upper or lower molars trans deviation;

T7: Asymmetric matching incisors upper/lower molar deviations with lower molars transverse deviation;

T8: Asymmetric matching basic bones upper/lower deviations;

T9: Asymmetric matching basic bones upper/lower anterior relations with anterior maxilla deviation;

T10: Asymmetric matching basic bones upper/lower anterior relations with anterior mandible deviation;

T11: Asymmetric matching incisors upper/lower deviations with anterior bases transverse deviation;

T12: Vertical asymmetric comparing L/R molars altitudes difference with maxillary arch rolling;

T13: Asymmetric comparing L/R molars altitudes difference with mandible arch rolling;

T14: Vertical asymmetric comparing basic bones R/L posterior differences (maxillary & mandible);

T15: Vertical asymmetric comparing L/R difference at mental points level (measuring maxilla-facial area and global face);

T16: Anterior-posterior asymmetric comparing R/L upper/lower molars anterior-posterior difference with lower ones;

T17: Anterior-posterior asymmetric comparing R/L upper/lower molars anterior-posterior relationship difference with lower ones;

T18: Anterior-posterior asymmetric comparing L/R upper basis lateral landmarks anterior-posterior difference with lower ones;

T19: Anterior-posterior asymmetric matching mandibular horizontal branch with R/L global hemifaces;

In such complex asymmetric facial/dental anatomic structures or relationships determinations according to this application, optional cumulative summative evaluations directed to overall condition assessments of a patient are preferably used. In some embodiments, exemplary cumulative summative or overall diagnosis comments can include: Asymmetry anterior posterior direction (AP comment or S1), Asymmetry vertical direction (VT comment or S2), and Asymmetry Transverse direction (TRANS comment or S3). Still further, highest level evaluation score(s) can be used by using one or more or combining S1, S2 and S3 to determine an Asymmetry global score (Asymmetry Global determination). For example, the exemplary Asymmetry global score can be a summary (e.g., overall class I, II, III), broken into few, limited, categories (e.g., normal, limited evaluation, detailed assessment suggested) or represented/characterized by dominant asymmetry condition (e.g., S1, S2, S3).

As shown in FIG. 35A, the exemplary text report also presents S1 anterior-posterior direction "synthetic" asymmetry comment, S2 vertical direction synthetic asymmetry comment, and S3 transversal direction synthetic asymmetry comment.

The "synthetic" terminology is derived in this application to form a pair of tables in each direction. In certain exemplary embodiments, the "synthetic" terminology can be determined from a combination of a plurality of tables from each assessment type (e.g., AP, V, Trans involving or representing substantial (e.g., >50%) portions of the skull) or a pair of tables in each direction.

For example, S1 synthetic comment is derived from Table 17 and Table 19. The derivation first assigns a score to each of the cells of Table 17 and Table 19. An exemplary score assignment is explained as follows For Table 17, C(1,3)=−2; C(1,2)=C(2,3)=−1; C(2,1)=C(3, 2)=1; C(3,1)=2; other cells are assigned with a value 0.

For Table 19, C(1,1)=−2; C(1,2)=C(2,1)=−1; C(2,3)=C(3, 2)=1; C(3,3)=2; other cells are assigned with a value 0.

The derivation of S1 synthetic comment evaluates the combined score by adding the scores from Table 17 and Table 19.

For instance, if C(1,3) in Table 17 is activated and C(1,1) in Table 19 is activated then the combined score will be the summation of the scores of C(1,3) of Table 17 and C(1,1) of Table 19. Since C(1,3) in Table 17 is assigned with a value −2 and C(1,1) in Table 19 is assigned with a value −2, therefore, the combined the score is −4. Obviously, the possible combined sore values for S1 are −4, −3, −2, −1, 0, 1, 2, 3 and 4.

The exemplary S1 synthetic comments can be based on the combined score value are summarized below.

If the combined score=−4 or −3, the S1 synthetic comment=strong left anterior-posterior excess.

If the combined score=−2, the S1 synthetic comment=left anterior-posterior excess tendency.

If the combined score=2, the S1 synthetic comment=right anterior-posterior excess tendency.

If the combined score=4 or 3, the S1 synthetic comment=strong right anterior-posterior excess.

If the combined score=0, no comment. Similar synthetic comment derivations are applied to the vertical direction and transversal direction.

Referring back to FIG. 35A, the exemplary text report displays S1=strong right anteroposterior excess, S2=none and S3=left upper deviation tendency.

In very rare cases, synthetic comments show up in all three directions, or the comments present some type of mixture of synthetic comments, which can prompt further extended diagnosis and/or treatment.

Further, selected exemplary method and/or apparatus embodiments according to the application can also provide a quick visual assessment of the asymmetry property of the maxillofacial/dental structural of a patient.

Figure 36:
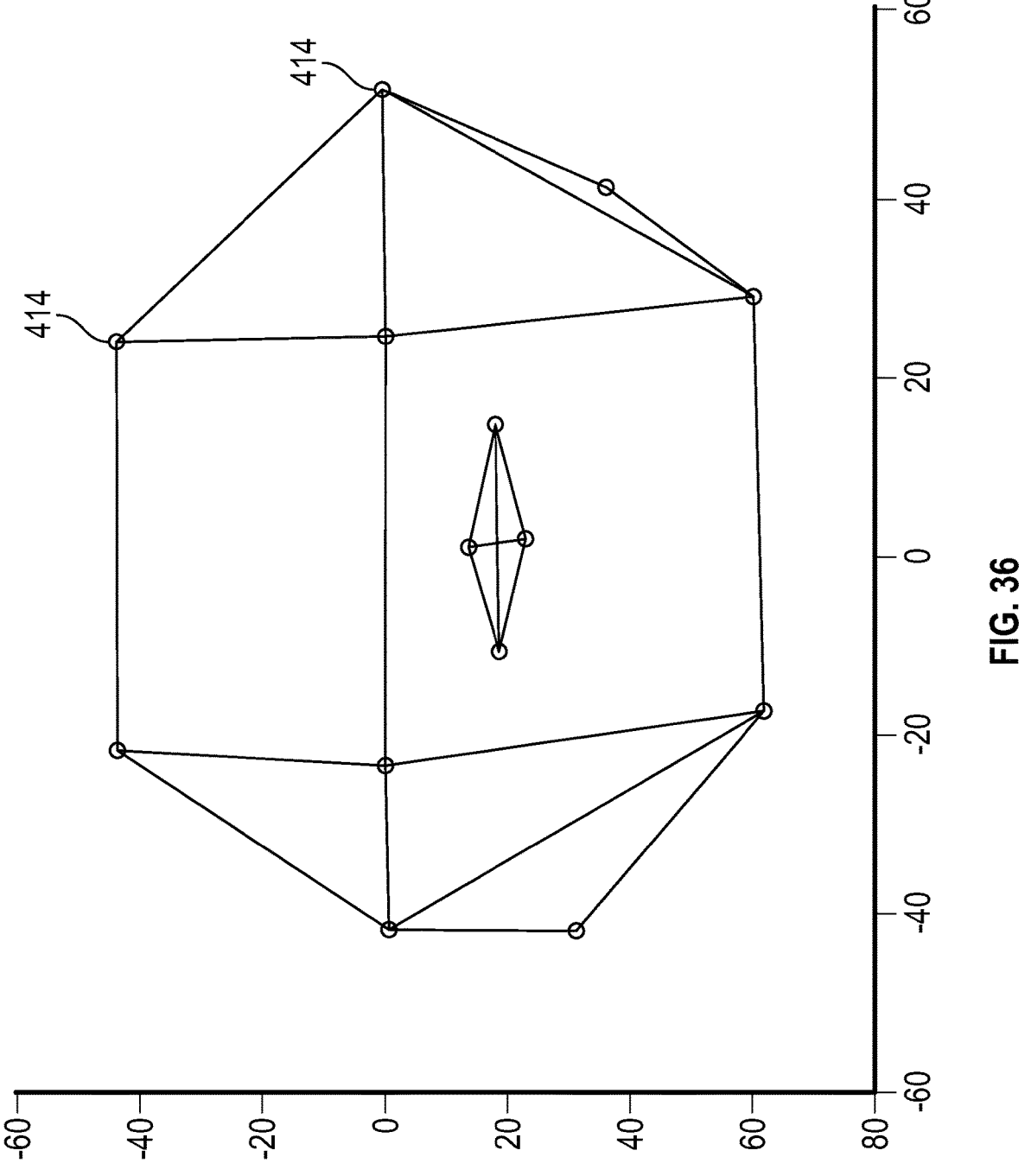
FIG. 36 is a graph that shows relative left-right asymmetry for a patient in a front view.

FIG. 36 is a plot or graph that shows the maxillofacial/dental structural features for a patient with respect to a front view, plotted using the landmarks, reference marks 414, selected by the operator (see FIG. 5). This type of displayed plot clearly shows asymmetry (left vs. right) in an objective fashion for this exemplary patient.

Figure 37:
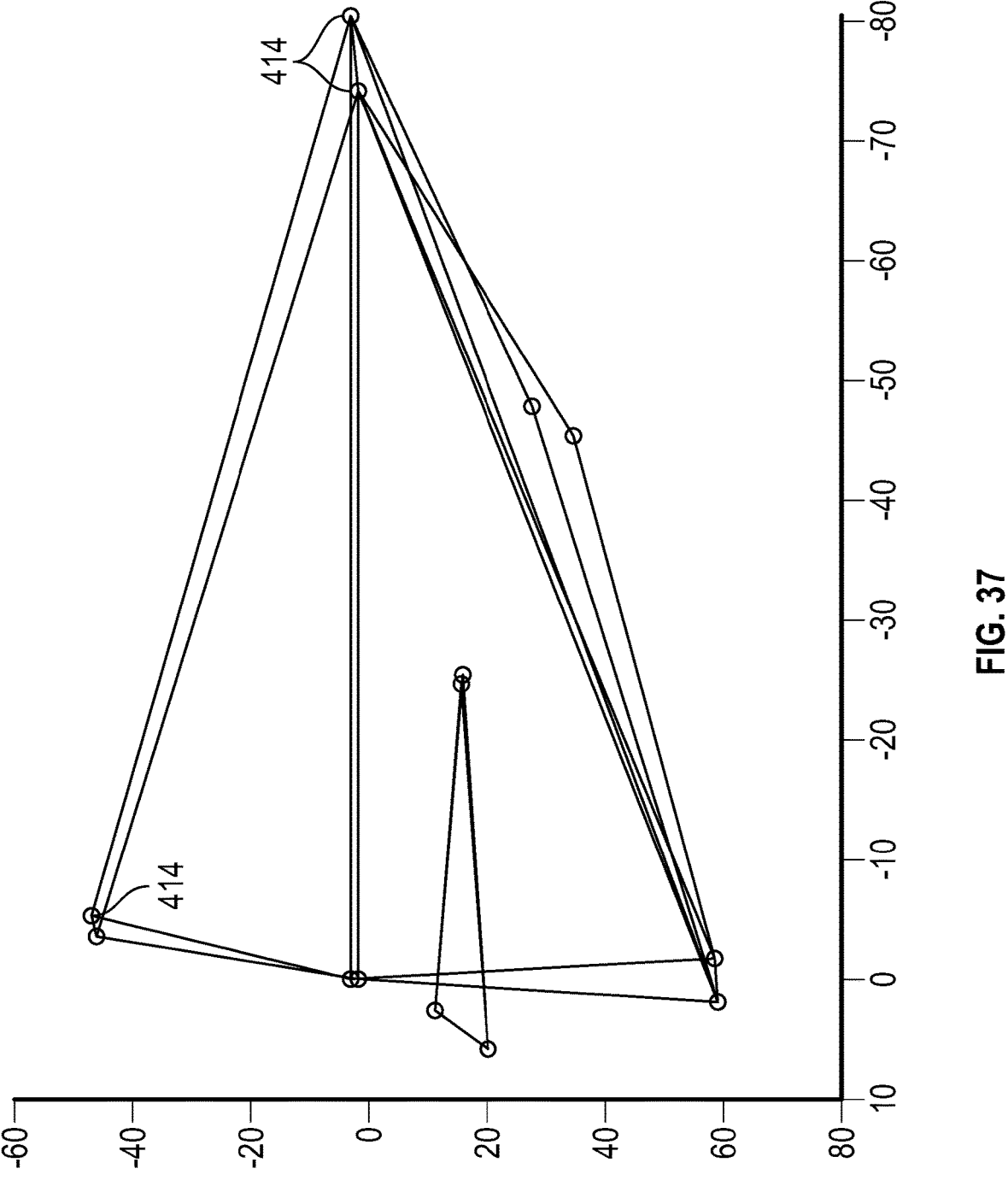
FIG. 37 is a graph showing relative overlap of left and right sides of a patient's face.

Likewise, FIG. 37 is a plot or graph of a sagittal view, with reference marks 414 showing how closely the left and right sides of a patient's face overlap, as another objective indicator of asymmetry.

Figure 38:
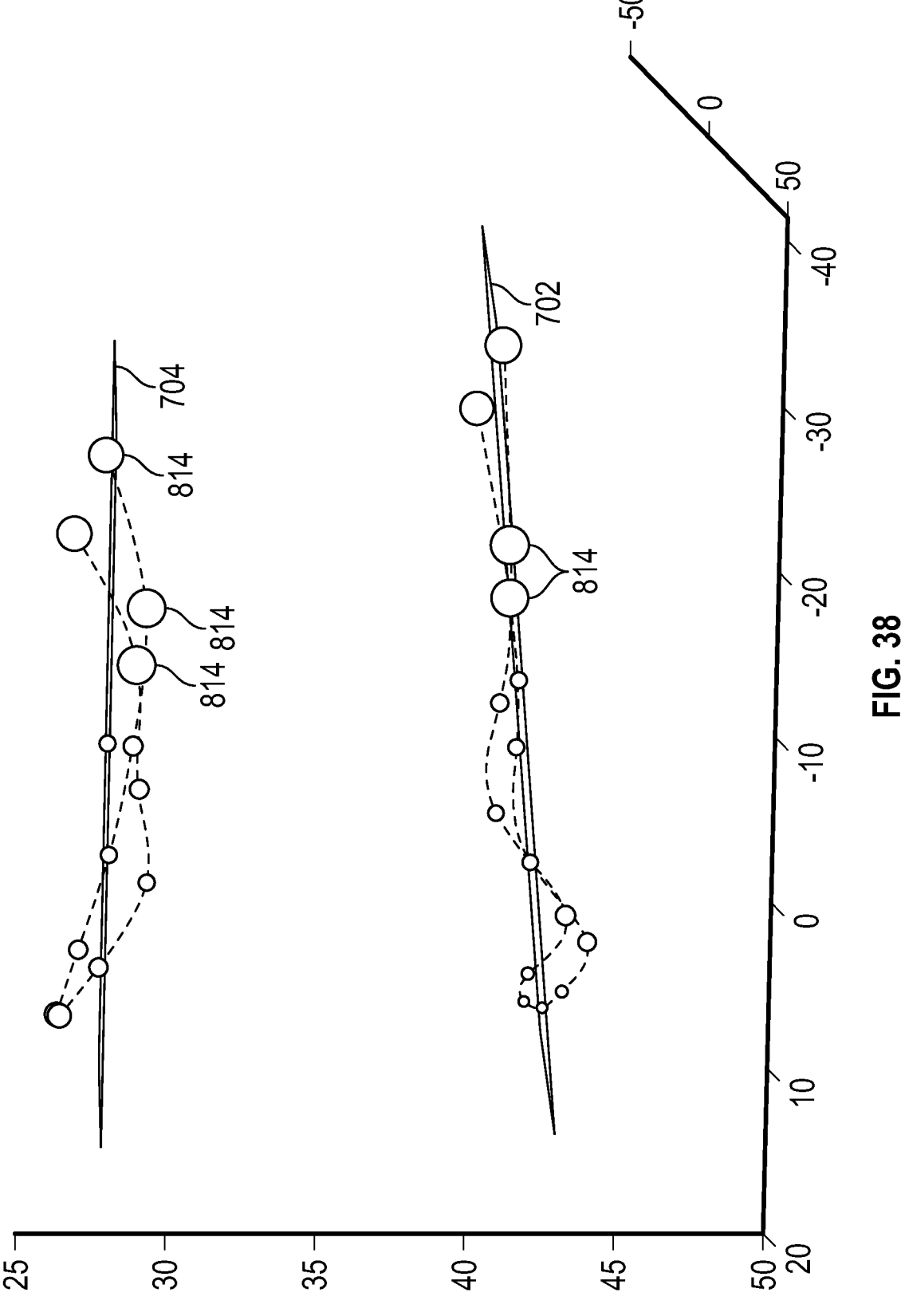
FIG. 38 is a graph showing facial divergence.

FIG. 38 is a plot or graph providing a quick visual assessment of noticeable improper alignment of the bite of a patient in a sagittal view of upper and lower jaw planes 704 and 702. Jaw plane 704 is computed based on the derived upper jaw marks 814, lower jaw plane 702 is computed based on the derived lower jaw marks 814. Derived marks 814 are computed based on the segmented teeth 304 shown in FIG. 4 and show the location of the tooth. The example shown in FIG. 38 depicts exemplary visual cues for a patient with a hyperdivergent pattern.

Similar arrangement of tables is also available for disharmony or off-asymmetry analysis.

For a quick reference to the exemplary assessment tables, the system of the present disclosure generates a checklist type concise summary page (e.g., FIG. 35B) that provides information with respect to table numbers (Tn), parameter numbers (Pk, j), cell indices (Cs, t), and actual disharmony assessment comments from assessment tables T1-T16 shown in FIG. 35B. The information obtained from this type of text report can be helpful for the practitioner, providing at least some objective metrics that can be useful in developing a treatment plan for a particular patient or evaluating treatment progress. Further beneficial to the practitioner can be cumulative summative evaluations directed to overall condition assessments of a patient. This can be the situation, in particular, when numbers of conditional reference points and relationships therebetween utilized to determine asymmetric facial/dental anatomic structures or relationships for a patient involve large numbers of view-oriented and 3D-oriented treatment conditions, with variable underlying causes.

In one exemplary off-asymmetric determination table embodiment, 16 assessment tables can be included with hundreds of reference points and several hundreds of relationships therebetween. In this exemplary off-asymmetric determination table embodiment, tables include:

T1: Matching incisors and global arches anterior-posterior upper/lower discrepancy;

T2: Matching incisors discrepancy and separate linear upper (and lower) incisors positions;

T3: Matching incisors discrepancy and separate linear (upper and) lower incisors positions;

T4: Matching incisors gap & upper-lower Class 2 torque differential (Class 3 compensation);

T5: Upper-lower separate responsibilities concerning upper-lower Class 2 torque difference (Class 3 compensation);

T6: Matching alveolar and basic upper/lower relationship;

T7: Upper/lower separate responsibilities concerning skeletal Class 2 and Class 3;

T8: Linear and angular biretrusion/biprotrusion;

T9: Global linear facial vertical height and its distribution;

T10: Facial height and facial divergence;

T11: Alveolar and basic divergences;

T12: Transverse linear and angular upper/lower alveolar relationship;

T13: Transverse linear and angular upper/lower basic relationship;

T14: Corpus/global mandible size;

T15: Class 2 division;

T16: Facial divergence and global dentition divergence.

Certain exemplary method and/or apparatus embodiments according to the present disclosure can address the need for objective metrics and displayed data that can be used to help evaluate cephalometric facial/dental anatomic structure (e.g., asymmetric). Advantageously, exemplary method and/or apparatus embodiments use measured and analyzed results as controls for a plurality of composition logic processors to compose patient specific indicative reports, which can include combined descriptive statements, preferably tabulated into 3-axis orientations (e.g., DOL reference system) suitable for assessment by the practitioner (e.g., treatment planning)

An exemplary data-driven 3D orthodontic biometry analysis reporting system can use a biometrics analysis processor or analysis engine that receives both population biometry data and patient specific biometry data to produce a plurality of descriptive statements that are organized (e.g., through a composition mechanism) and presented to the end user (doctors/patients). An exemplary biometrics analysis processor, using artificial intelligence (AI) algorithms and related machine-learning approaches, generates diagnostic orthodontic information (e.g., composed descriptive statements) that can be useful for patient assessment and ongoing treatment. In one embodiment, the resultant diagnostic orthodontic information can be reported in an exemplary format shown in FIG. 46 and/or FIG. 48.

Figure 39:
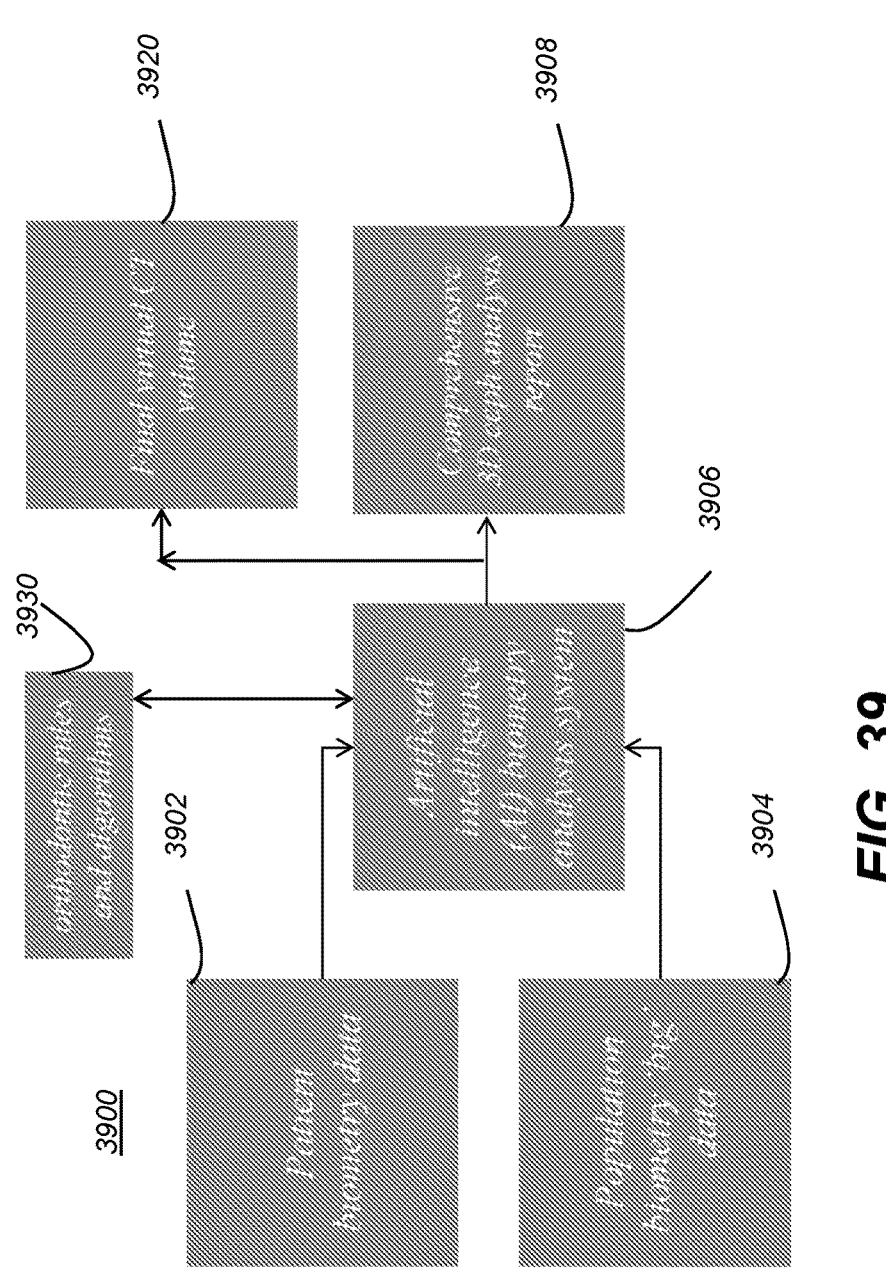
FIG. 39 is a diagram that shows exemplary logic processing mechanisms and data according to certain exemplary embodiments that can be used for providing assessment and guidance to support orthodontic applications.

FIG. 39 shows exemplary logic processing mechanisms and data that can be used for providing assessment and guidance to support orthodontic applications. An exemplary method embodiment 3900 shown in FIG. 39 can be implemented within systems such as the system 100 or methods such as sequence 200 described herein. As shown in FIG. 39, patient specific biometry data 3902 and population data 3904, e.g., computed based on the raw data (such as segmented teeth and landmarks described previously) obtained from CBCT, optical scanning, or other source, is input to a biometrics analysis engine 3906. In response, biometrics analysis engine 3906, performs calculations as described herein and generates control signals for composition logic circuits that output descriptive statements organized into comprehensive 3D cephalometric analysis reports 3908 identifying one or more dental/maxillofacial abnormalities. According to an exemplary embodiment of the present disclosure, descriptive statements describing one or more dental/maxillofacial abnormalities can include, encompass or supplement some of those given previously in FIGS. 31A-32D, 35A, 35B or preferably 46.

As described herein, memory within or coupled to biometrics analysis engine 3906 such as memory 132 can be used to store the patient specific data 3902 and the population data 3904 (e.g., the statistical database of cephalometric information gathered from a population of patients). Preferably, the population biometry 3904 and patient specific data 3902 are categorized in the form of data trees, for example, as shown in FIGS. 40 and 41.

Figure 40:
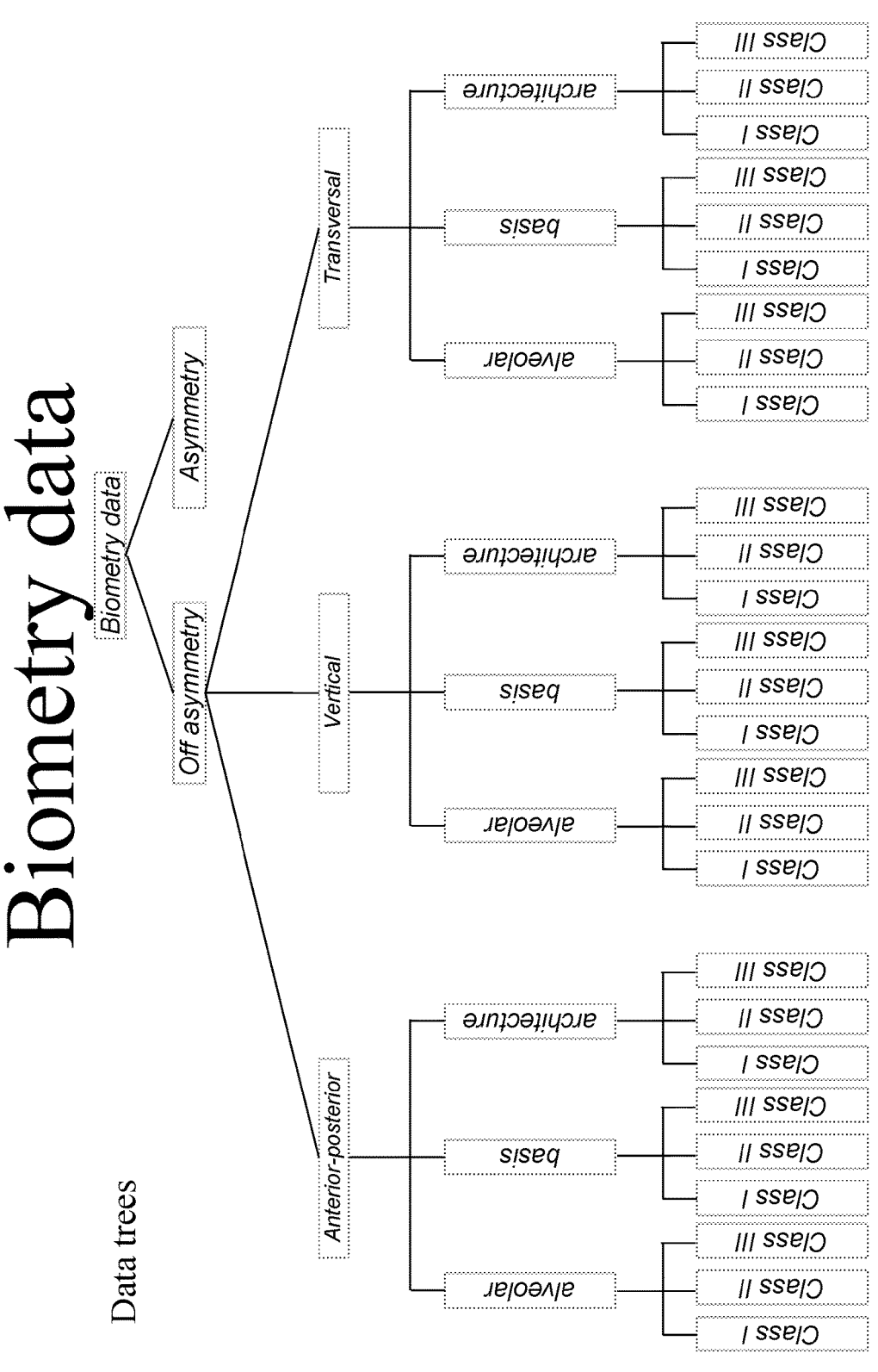
FIG. 40 is a diagram that shows an exemplary tree structure for "off asymmetry" or "disharmony" data that contain the information regarding structural "disharmony" of dentition and maxillofacial anatomy.
Figure 41:
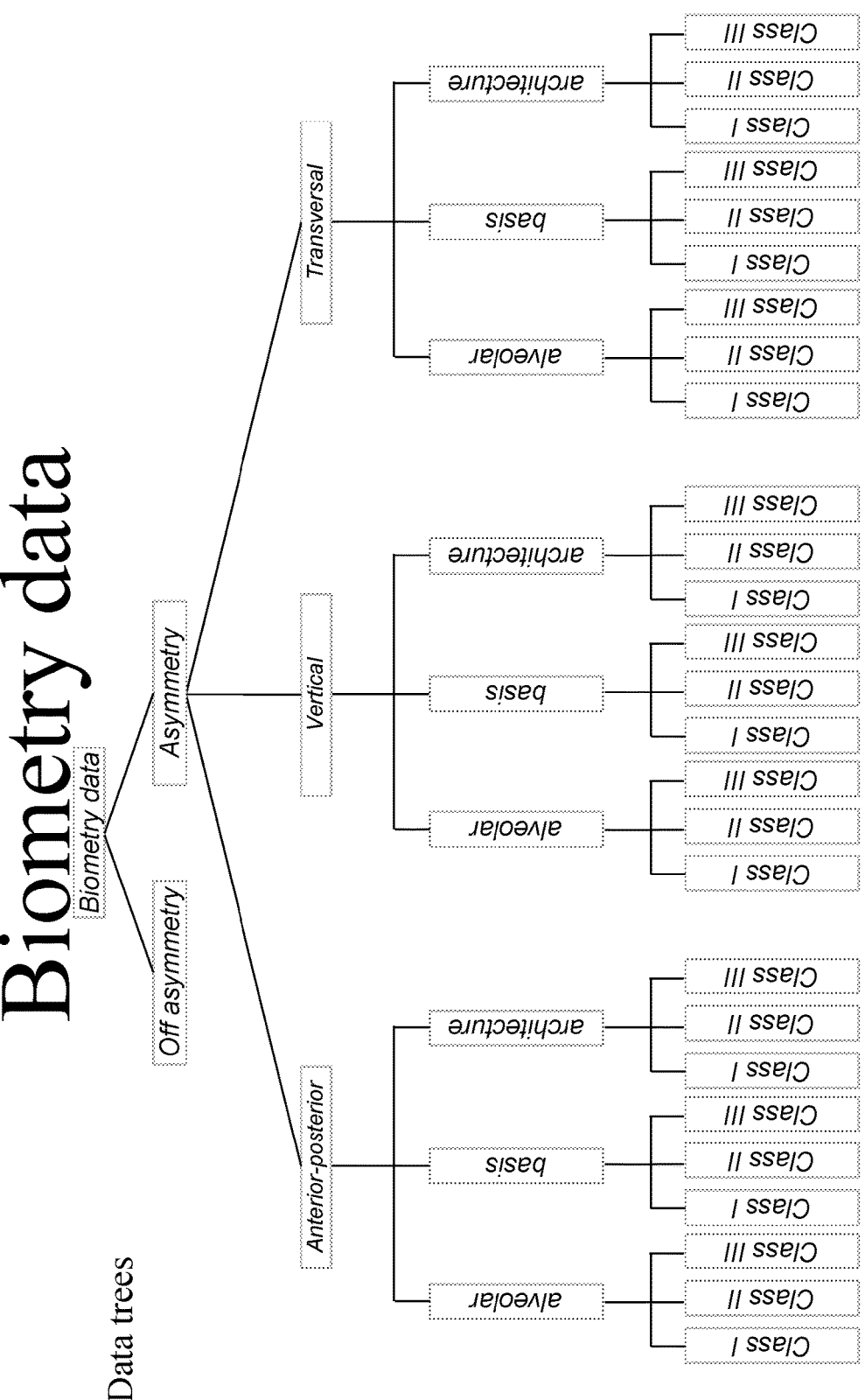
FIG. 41 is a diagram that shows an exemplary tree structure for "asymmetry" data that contain the information regarding structural asymmetry of dentition and maxillofacial anatomy.

FIG. 40 is a diagram that shows an exemplary tree structure for "off asymmetry" or "disharmony" or "dental-facial deformity" data that contain the information regarding structural "disharmony" of dentition and maxillofacial anatomy. Said "disharmony" data further is branched into three directional data containing clinical information specialized in three spatially orthogonal directions, namely, anterior-posterior (front-back), vertical (up-down), and transversal (side-side).

Further, said directional data itself covers structural "harmony" or "disharmony" information in three different levels that can be alveolar level, basis level and architecture level. Exemplary alveolar data include teeth positions, teeth torques, and jaw inertia centers. Exemplary basis data include corpus length, pseudo FMA (Frankfort mandibular plane angle), and mandible foramen right/left position difference. Exemplary architecture data include the average coordinate of mental foramen, the ratio of infra-orbital width and anterior mandible width, and maxilla-mandible height.

Still further, said data at each of the three alveolar level, basis level and architecture level are further classified, if necessary, as Class I, Class II and Class III. Said Class I indicates neutrocclusion, Class II indicates distocclusion and Class III indicates Mesiocclusion,. These classifications are familiar to the people skilled in the art.

FIG. 41 is a diagram that shows an exemplary tree structure for "asymmetry" or "dentalfacial asymmetry" data that contain the information regarding structural asymmetry of dentition and maxillofacial anatomy. Said "asymmetry" data is further branched into three directional data containing clinical information specialized in three spatially orthogonal directions, namely, anterior-posterior (front-back), vertical (up-down), and transversal (side-side).

Further, said directional data itself covers structural asymmetry information in three different levels that can be alveolar level, basis level and architecture level. Exemplary alveolar data include upper incisors transversal deviation, upper arch transversal deviation and arch rotation. Exemplary basis data include maxilla right-left height difference, mandible right-left height difference, and upper/lower arch right/left deviation. Exemplary architecture data include facial depth right/left difference, anterior-posterior mental foramen right/left position difference, and difference of right/left maxilla-mandible divergences.

Still further, said data at each of the three alveolar level, basis level and architecture level is further classified, if necessary, as Class I, Class II and Class III. Said Class I indicates neutrocclusion, Class II indicates distocclusion and Class III indicates Mesiocclusion,. These classifications are familiar to the people skilled in the art.

Figure 42:
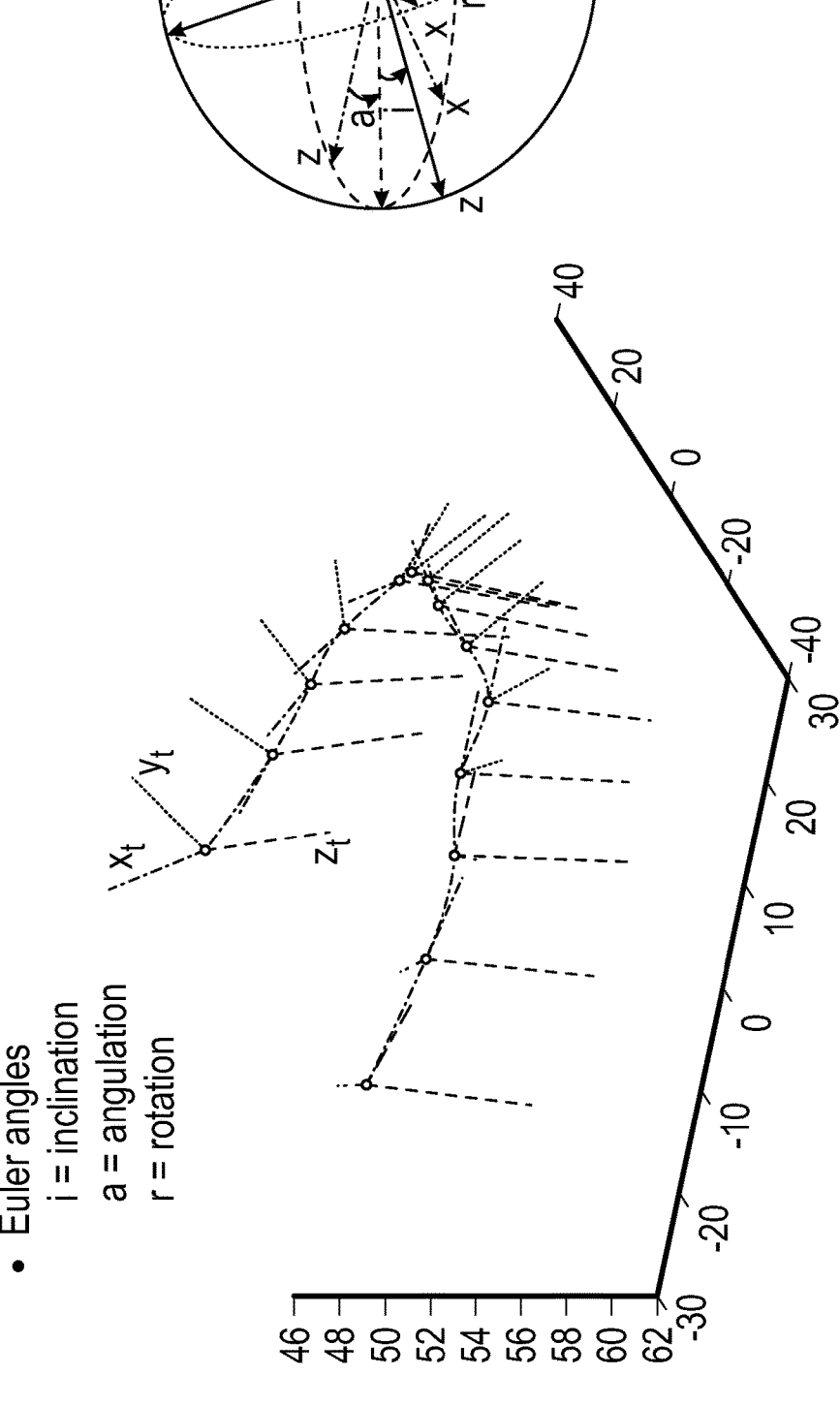
Figure 43:
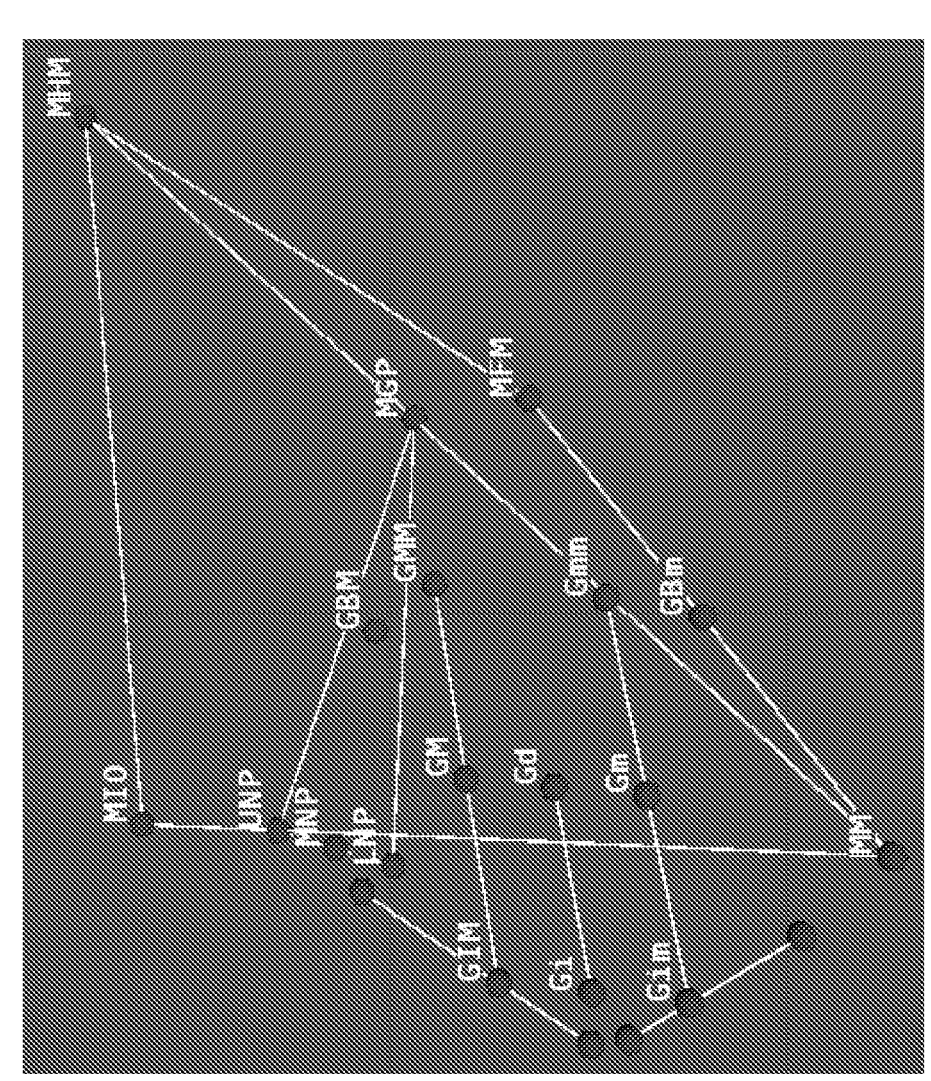
Figure 44:
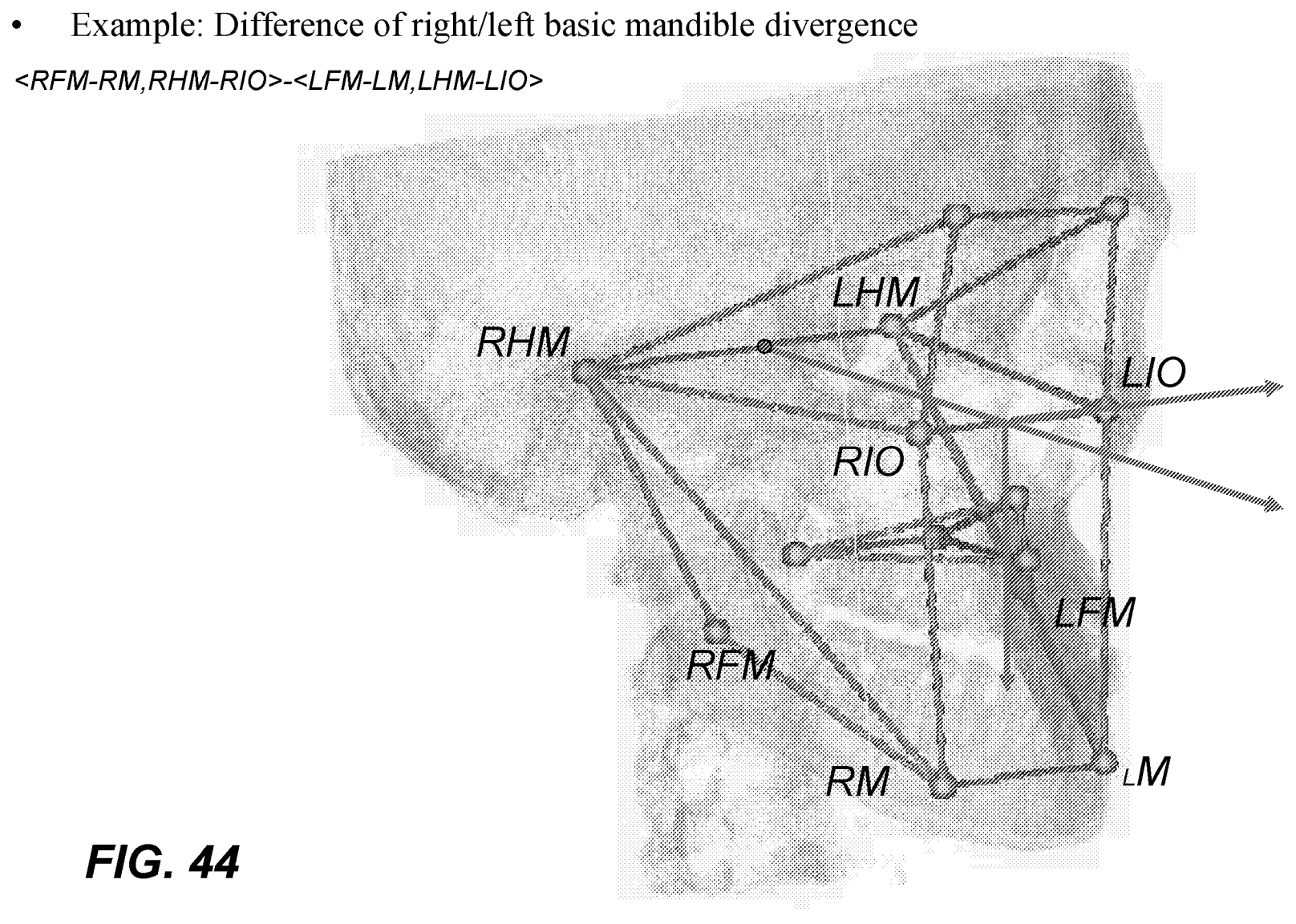

FIGS. 42, 43, and 44 are diagrams that illustrate exemplary data terms: that include tooth Euler angles, Pseudo FMA, and Difference of right/left basic mandible divergence, respectively.

Figure 45:
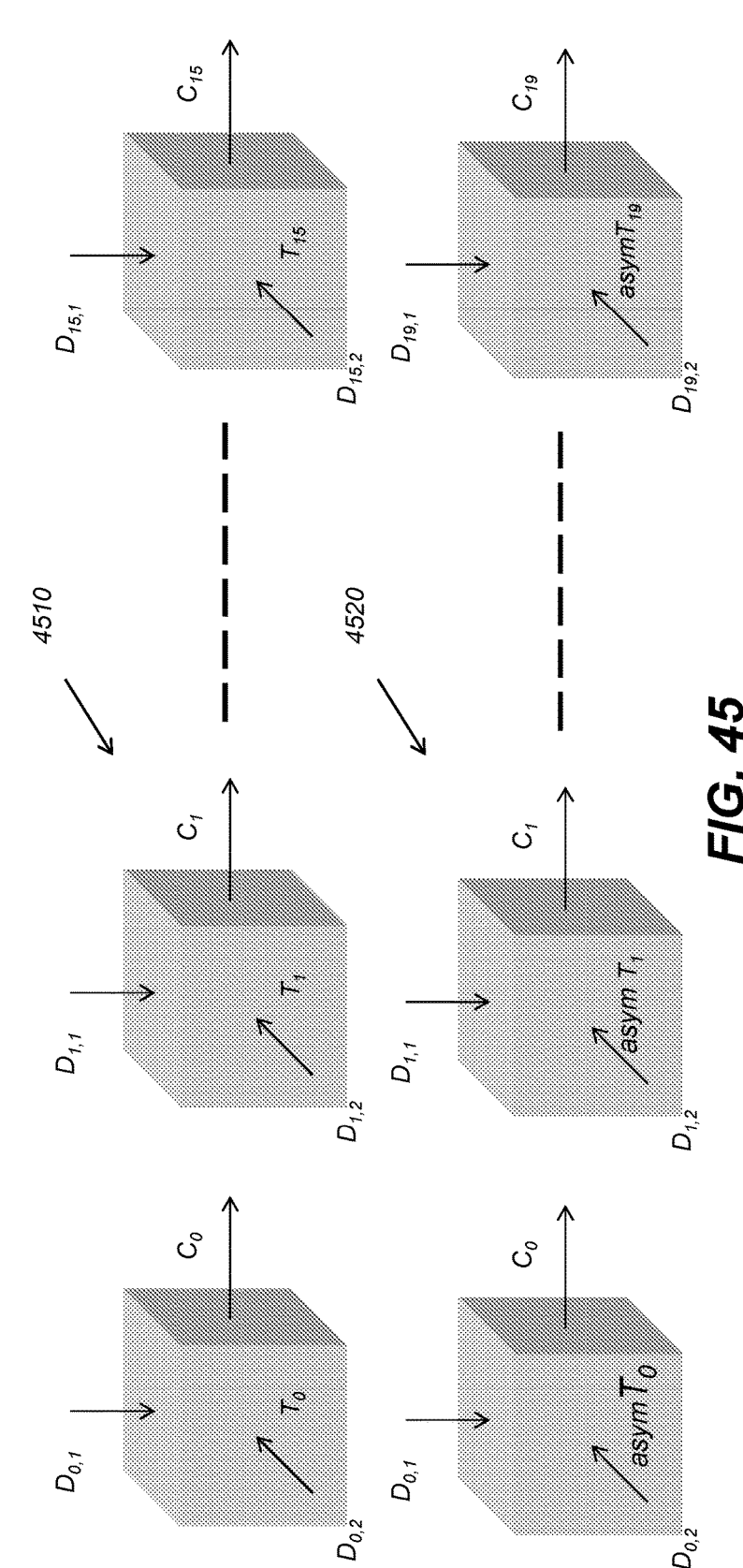
FIG. 45 is a diagram that illustrates an exemplary analysis engine system for maxillofacial/dental off-asymmetry and asymmetry analysis according to certain exemplary embodiments.

FIG. 45 is a diagram that illustrates an exemplary Ai engine 4510 for disharmony (e.g., Off asymmetry) analysis and an exemplary Ai engine 4520 for asymmetry analysis. As shown in FIG. 45, exemplary disharmony (Off asymmetry) analysis 4510 can include 16 AI engines, where each AI engine receives various biometric data as inputs and generates various diagnosis comment outputs. Exemplary asymmetry analysis 4520 can include 19 AI engines, where each AI engine receives various biometric data as inputs and generates various diagnosis comment outputs.

FIG. 27 is a diagram that illustrates exemplary components of an AI engine that can implement the disharmony (Off asymmetry) analysis 4510 and asymmetry analysis 4520.

FIG. 46 presents an exemplary biometry analysis report generated through a machine intelligence mechanism according to exemplary method and/or apparatus embodiments of this application. As shown in FIG. 46, biometry analysis report 4600 can be generated using a plurality of composition logic circuits driven by control signals from patient specific maxillofacial/dental abnormalities analysis, that is to be elaborated next.

As shown in FIGS. 47-48, an exemplary Anterior-posterior description 4602 for the Off Asymmetry Diagnosis includes at least one descriptive statement and as shown includes a plurality of 4 descriptive statements. As shown in FIGS. 47-48, statement A of Anterior-posterior description 4602 includes up to 3 descriptive comments.

Figure 50:
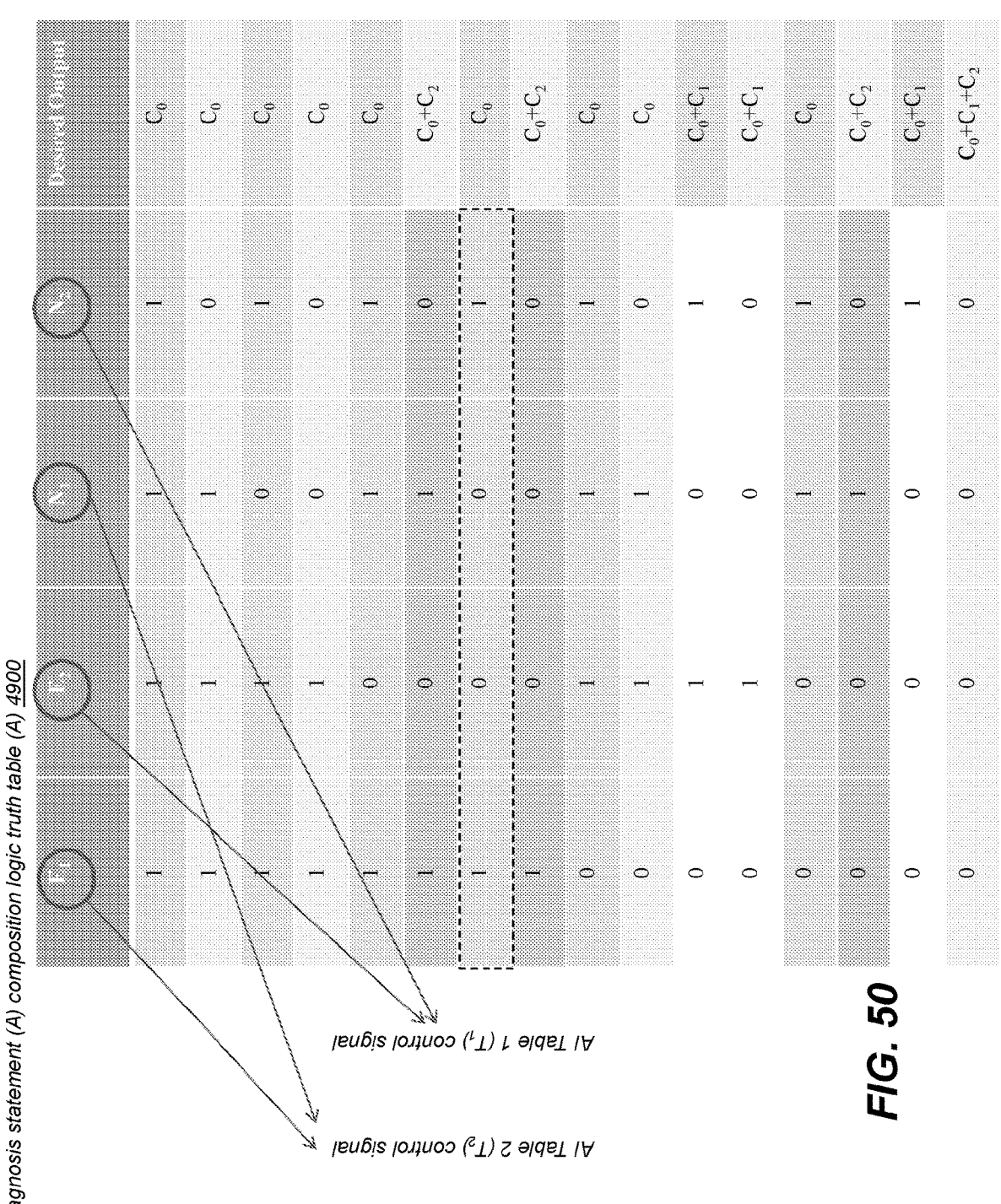

Referring to FIG. 47, a portion of the final report 4600 of a patient displays an exemplary composite statement (A) that can be decomposed into three separable comments derived from three AI tables:

Comment $C_0$ from AI Table 0 ($T_0$) as shown in FIG. 48
Comment $C_1$ from AI Table 1 ($T_1$) as shown in FIG. 48
Comment $C_2$ from AI Table 2 (T2) as shown in FIG. 48
As shown, this exemplary statement (A) contains at least one comment. The determination of the presence of a comment in said statement (A) is controlled by an intelligent mechanism that is illustrated in FIG. 49 with a composition logic truth table (A) 4900 for statement (A). The last column of the composition logic truth table (A) 4900 lists sixteen possible outputs (e.g., combinations of comments C0, C1 and C2), one of which is to be presented as a part of Anterior-posterior description 4602 in the final report shown in FIG. 4600. The determination of which output is to be presented by the composition logic truth table (A) 4900 is controlled by the pattern of four control signals E1, N1 (control signals for Table 1, see FIGS. 50), E2 and N2 (control signals for Table 2, see FIG. 50). For example, as shown by a dashed box in FIG. 49, a pattern of 0000 in composition logic truth table (A) 4900 produces output C0+C1+C2. Further for example, a pattern 1001 produces C0 as shown by a dashed box in FIG. 50.

Figure 51:
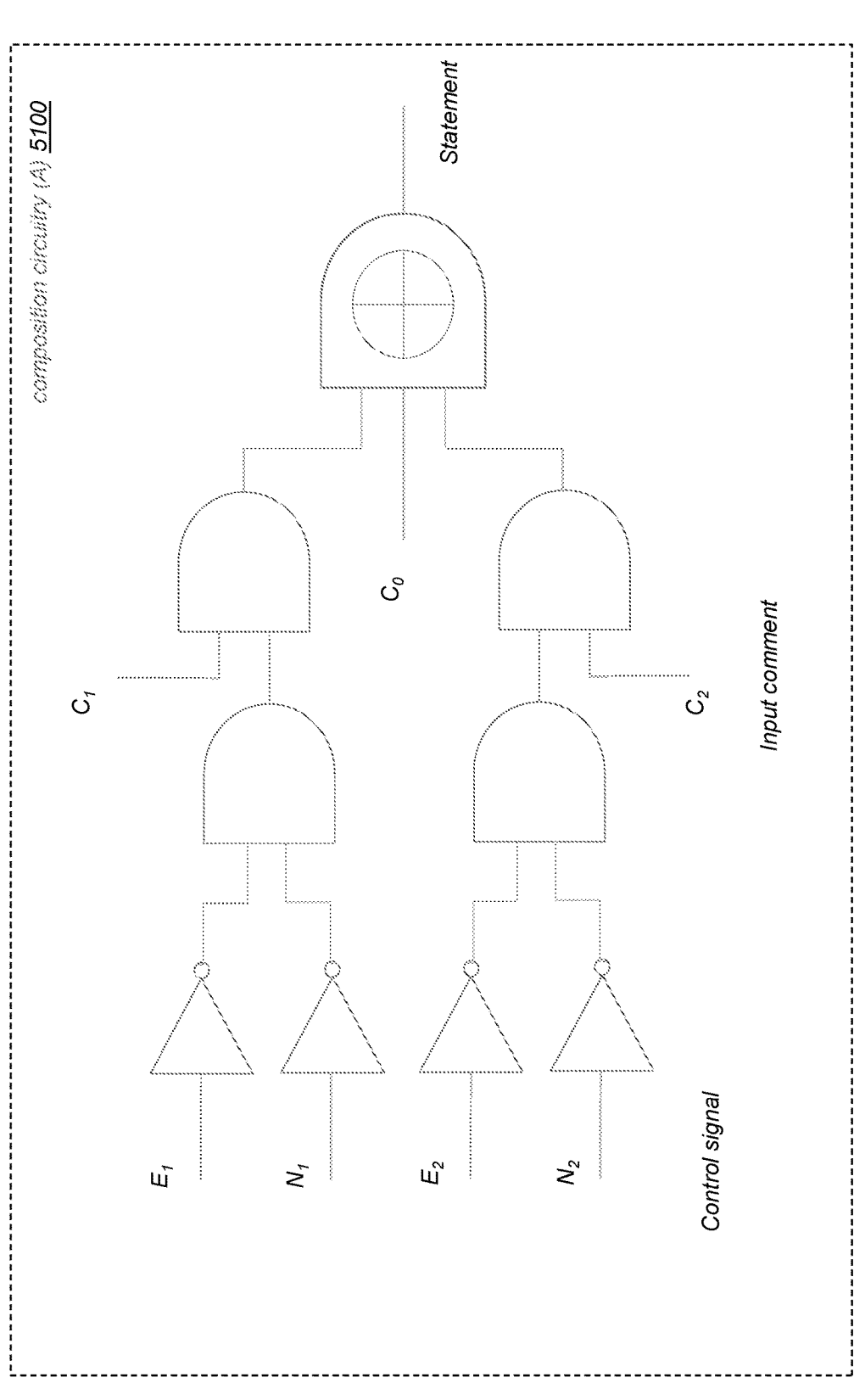
FIG. 51 is an exemplary hardware configuration for controlling the intelligent reporting system

Composition logic truth table (A) 4900 can be readily mapped to a composite circuit that is constructed with logic gates. An exemplary composite circuit (A) 5100 including AND gates, inverters, and ADD gate can implement the composition logic truth table (A) 4900 as shown in FIG. 51. As can be appreciated by those skilled in automated writing arts, such composite circuits can be implemented by using software code or a combination of hardware and software.

FIG. 52 is a diagram that shows that statement (B) that can be produced by the similar circuit mechanism used to generate to statement (A) described above.

In FIG. 46, the exemplary anterior-posterior description 4602 includes four descriptive statements, which each can be generated by a composition circuit.

Figure 53:
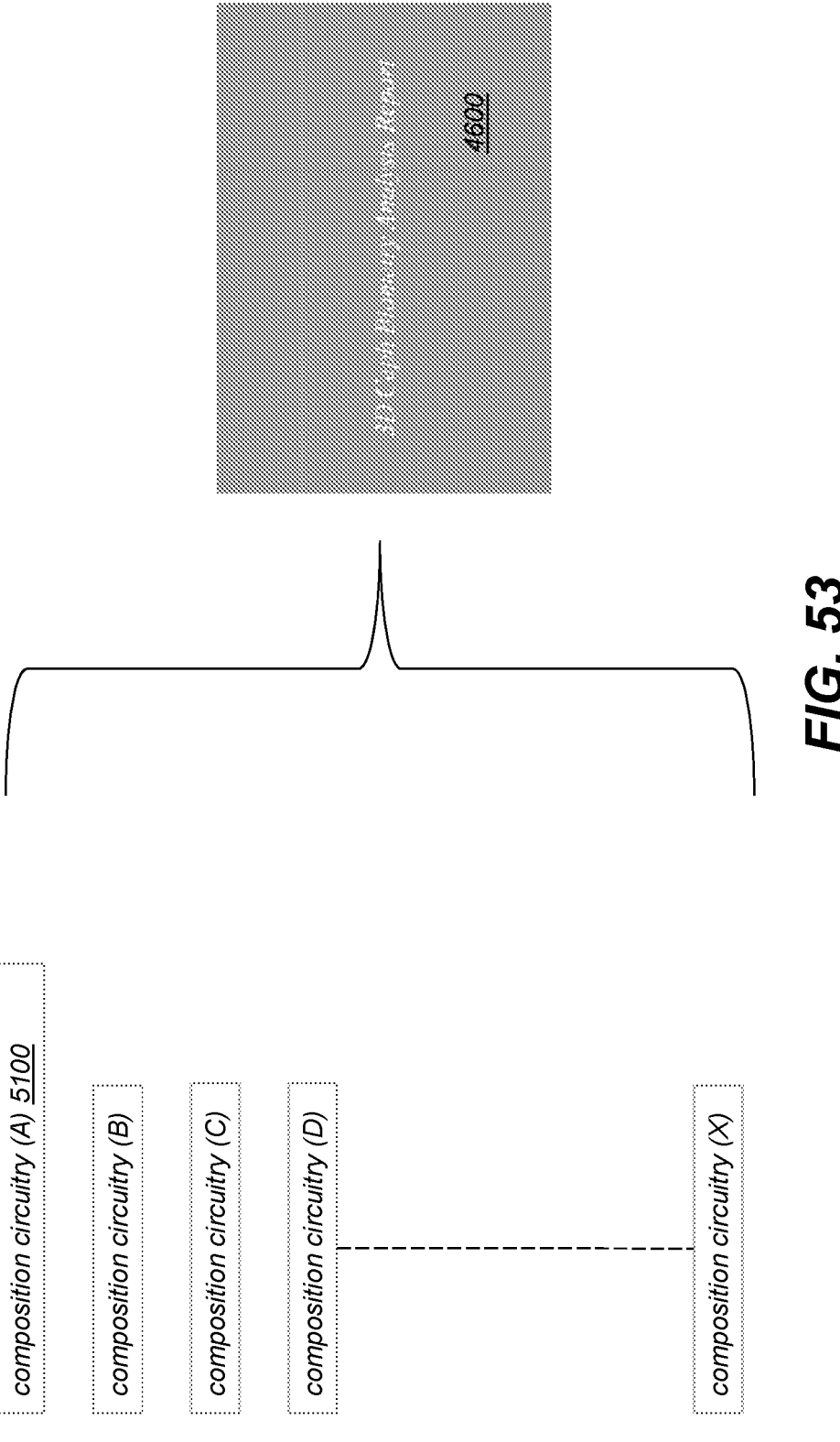
FIG. 53 is a diagram that illustrates an exemplary final report, according to embodiments of this application, can be formed by combining a plurality of outputs from a plurality of composition circuits.

FIG. 53 is a diagram that illustrates an exemplary final report of the according to embodiments of this application can be formed by combining a plurality of outputs from composition circuit A through composition circuit X for the entire report 4600 shown in FIG. 46.

Figure 54:
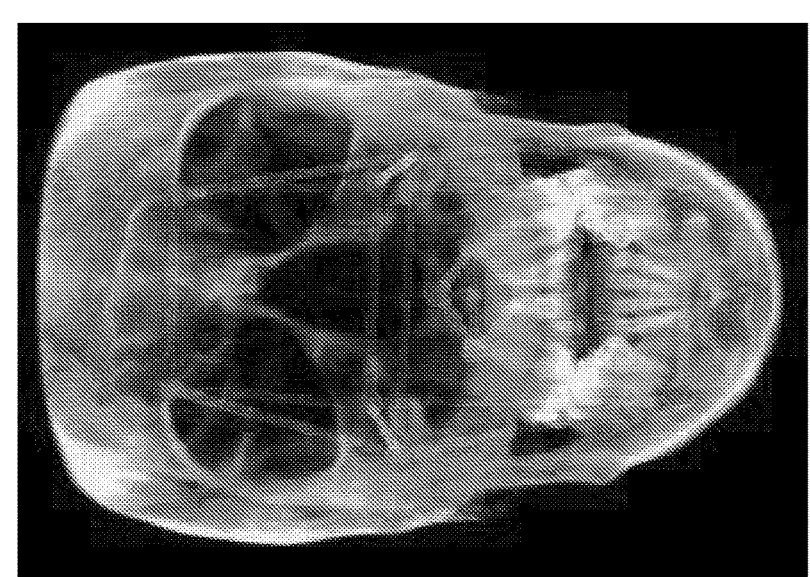
FIG. 54 is a diagram that shows another exemplary statement contained in the exemplary final report and an underlying patient specific maxillofacial/dental abnormality in original CBCT data.
Figure 55:
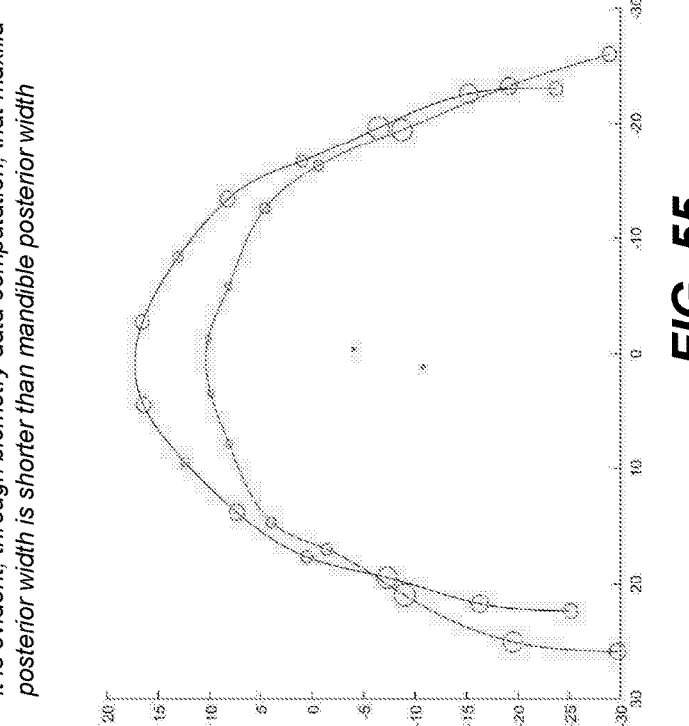
FIGS. 55 shows an underlying patient specific maxillofacial/dental abnormality in representative graphical form selected via an exemplary final report.

FIG. 54 is a diagram that shows another exemplary statement (Statement E) contained in the exemplary final report 4600, which each can be generated by a composition circuit. FIGS. 54 shows an underlying patient specific maxillofacial/dental abnormality (transformed to Statement E in final report 4600) in original CBCT data. FIG. 54 demonstrates that said exemplary Statement E is not obviously observable just through CBCT volume examination. In contrast, FIGS. 46 and 55 illustrate the clinical usefulness of the automatically generated analysis report 4600. Said Statement E is evident, through biometry data computation in FIG. 55, that maxilla posterior width is shorter than mandible posterior width as readable in the analysis report 4600. In one exemplary embodiment, operator selection of a composite statement (e.g., statement (E) for Off Asymmetry Diagnosis, Transversal description) brings up at least one 2D/3D view of a graphical depiction of the underlying patient specific maxillofacial/dental abnormality (e.g., FIG. 55). In one embodiment, selectable comments of the composite statements (e.g., individual comments $C_0, \ldots, C_n$ of statement (A) of Anterior-posterior description 4602), when selected, brings up at least one preset 2D/3D view of a graphical depiction of the underlying patient specific maxillofacial/dental abnormality. In one embodiment, selectable composite statements (e.g., statement A, . . . , statement N) of a section of the biometry analysis report 4600, when selected, brings up at least one preset 2D/3D view or a graphical depiction of the selected underlying patient specific maxillofacial/dental abnormality. In one embodiment, selectable sections (e.g., anterior-posterior, . . . , traversal) of the biometry analysis report 4600, when selected, brings up at least one preset 2D/3D view or a graphical depiction of the selected underlying patient specific maxillofacial/dental abnormality. In one embodiment, selection of a disharmony section or a asymmetry section (e.g., Off Asymmetry Diagnosis or Asymmetry Diagnosis) of the biometry analysis report 4600 brings up at least one preset 2D/3D view or a graphical depiction of the selected underlying patient specific maxillofacial/dental abnormality. In one embodiment, exemplary preset at least one 2D/3D view or a graphical depiction of the selected underlying patient specific maxillofacial/dental abnormality can be modified, and saved as a future preset, by an operator.

As shown in FIG. 46, in certain exemplary embodiments the biometry analysis report 4600 (e.g., 3D maxilla-facial biometry analysis report) can include a patient identifier, an asymmetry patient specific description divided into one or more of an anterior-posterior composite statement, a vertical composite statement, and a transversal composite statement, and a disharmony patient specific description divided into one or more of an anterior-posterior composite statement, a vertical composite statement, and a transversal composite statement, where the statements are compound descriptive (diagnostic) phrases combinable according to a patient specific biometry data (e.g., from a computed tomographic scan of a patient's head) that summarize a patient's current facial/dental anatomic structure (e.g., maxillofacial/dental abnormalities). In one embodiment, an asymmetry patient specific description and a disharmony patient specific description each of the asymmetry patient specific description and the disharmony patient specific description can include a synthetic composite statement.

Described herein is a computer-executed method and/or apparatus embodiments for 3-D cephalometric analysis of maxillofacial asymmetry for a patient. Certain exemplary method and/or apparatus embodiments can acquire and display reconstructed volume image data of a patient's head including one or more segmented dentition elements within the mouth of the patient. Optional additional operator provided reference marks can be added to the reconstructed volume image data. Exemplary method and/or apparatus embodiments can compute and display cephalometric parameters for the patient according to reconstructed volume image data and population biometry data, and then computes, using the computed cephalometric parameters, one or more results indicative of maxillofacial/dental asymmetry. Certain exemplary method and/or apparatus embodiments can then generate a report including composite statements representative of patient specific maxillofacial/dental asymmetry using a plurality of composition logic circuits.

Described herein is a computer-executed method and/or apparatus embodiments for 3-D cephalometric analysis of maxillofacial structure for a patient for producing a final virtual CT volume ($CT_{end}$), preferably corresponding to an orthodontic treatment outcome including at least the segmented teeth (e.g., crowns and/or roots). After acquiring initial reconstructed volume image data of a patient's head including one or more segmented dentition elements, exemplary method and/or apparatus embodiments can compute and display a final (target) virtual CT volume for the patient according to the initial reconstructed volume image and population biometry data, and then compute, one or more results indicative of corrections to (e.g., reduce or minimize) maxillofacial/dental asymmetry. Exemplary method and/or apparatus embodiments can compute and display cephalometric parameters for the patient according to initial reconstructed volume image data and population biometry data, and then compute, cephalometric parameters indicative of maxillofacial/dental asymmetry, and then one or more results indicative of corrections to the maxillofacial/dental asymmetry. Exemplary results indicative of corrections to maxillofacial/dental asymmetry include a final tooth arrangement in the final virtual CT volume that reduces or minimizes disharmony and/or asymmetry in the maxillofacial/dental structure. Preferably, such one or more results indicative of corrections to maxillofacial/dental asymmetry further comply with treatment plans (e.g., from an orthodontic practitioner) and/or orthodontic treatment guidelines (e.g., with or without surgery). According to other method and/or apparatus embodiments for 3-D cephalometric analysis of maxillofacial/dental structure, one or more aligners can be generated to incrementally move dentition toward the final tooth arrangement in final virtual CT volume ($CT_{end}$).

Again, FIG. 39 shows exemplary logic processing mechanisms and data that can be used for providing assessment and guidance to support orthodontic applications. As shown in FIG. 39, patient specific biometry data 3902 and population data 3904, e.g., computed based on the raw data (such as 3D reconstructed segmented head including teeth and landmarks described previously) obtained from imaging systems such as dental x-ray imaging apparatus (e.g., CBCT), depth resolved imaging, optical scanning, or other source, is input to a biometrics analysis engine 3906. In one embodiment, patient specific biometry data 3902 is a reconstructed CT volume of the patient's head (e.g., dental CBCT volume 202). In response, biometrics analysis engine 3906, performs calculations as described identifying one or more dental/maxillofacial abnormalities. According to exemplary embodiments of the present disclosure, biometrics analysis engine 3906 can then generate a target or final virtual CT volume, which preferably results from bone/teeth movement/adjustment to address or compensate/correct the one or more dental/maxillofacial abnormalities. In one embodiment, patient specific final virtual CT volume is a reconstructed CT volume of the patient's head (e.g., dental CBCT volume 202). Also, the biometrics analysis engine 3906 can be coupled to access orthodontic rules and algorithms 3930 that can provide guidelines or requirements for automatically repositioning teeth or user assisted repositioning in accordance with therapeutic treatments (or aesthetic). Preferably, the final virtual CT volume implements therapeutic orthodontic requirement and/or guidelines such as incremental and cumulative individual maximum tooth rotation, maximum tooth movement etc.

Figure 57:
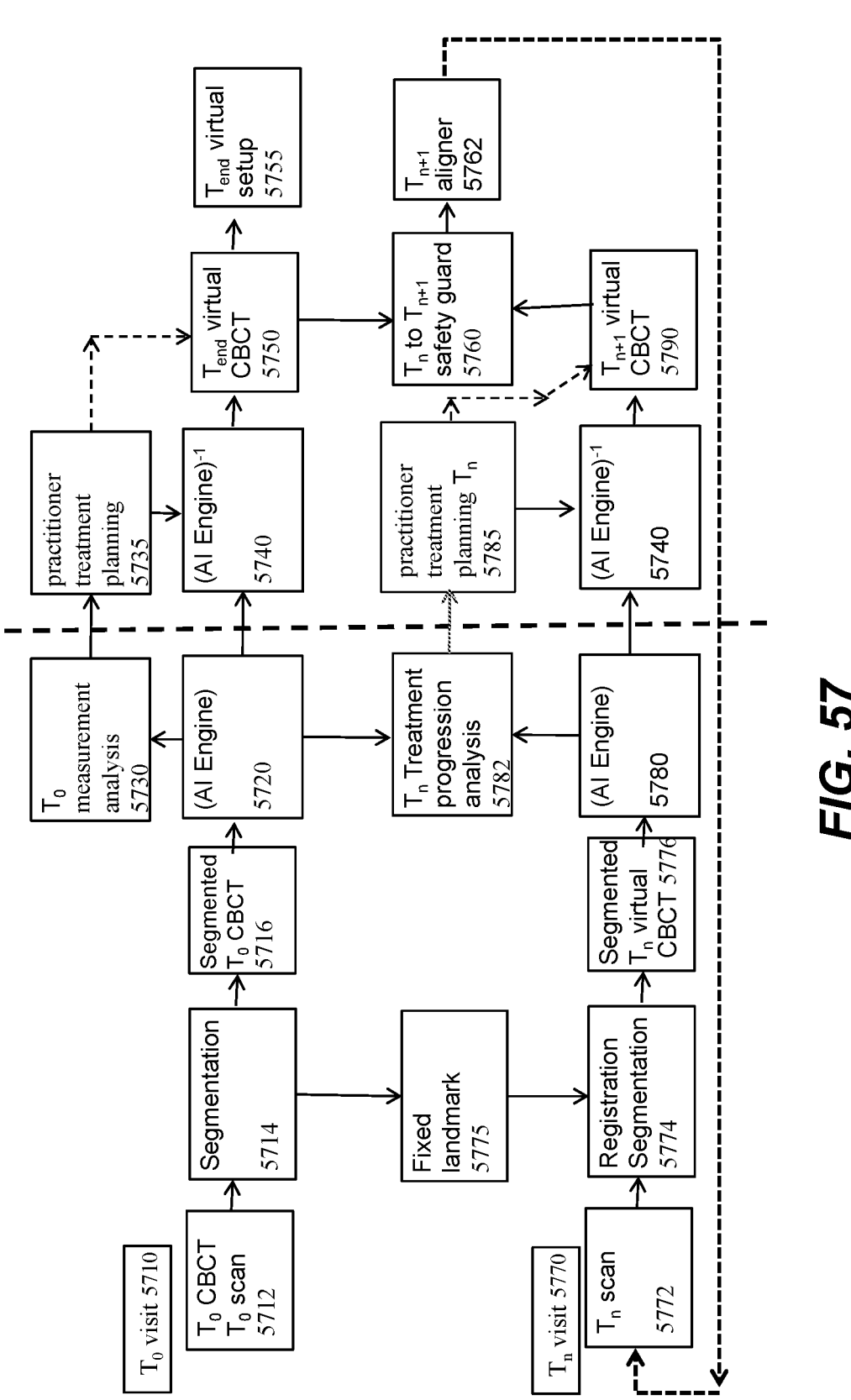
FIG. 57 is a diagram that shows exemplary flowchart according to certain exemplary embodiments to generate a final virtual CT Volume or generating one or more aligners to move toward a final tooth arrangement in the final virtual CT Volume to reduce/correct a maxillofacial/dental abnormality.

Referring now to FIG. 57, an exemplary method embodiment can generate a final virtual CT volume, which preferably results from calculated dental/maxillofacial movement to address or compensate/correct one or more dental abnormalities with respect to all or selected parts of the dental/maxillofacial structure. Further in FIG. 57, an overall method embodiment can produce aligners for use to reposition (e.g., incrementally) at least the patient's teeth to an arrangement in the final virtual CT volume that results from reducing asymmetry and disharmony in dental/maxillofacial structure.

As shown in FIG. 57, an initial CT volume (e.g., 3D reconstructed volume) representing an initial dental/maxillofacial arrangement (e.g., including an initial tooth arrangement) is obtained, referred to hereinafter as the Segmented $T_0$ scan or Segmented $T_0$ CBCT (block 5716). The Segmented To CBCT may be obtained in a variety of ways. For example, the patient's skull including teeth may be scanned or imaged using well known technology. Then, the dental/maxillofacial structure (dentition, bones and cephalometric parameters) can be segmented, identified and labeled.

In one exemplary embodiment, the Segmented $T_0$ CBCT is obtained during a $T_0$ visit (e.g., initial visit) by the patient to a dental practitioner such as an orthodontist (block 5710). During the $T_0$ visit, a dental extra-oral x-ray CBCT imaging apparatus can perform a preset exposure pattern or scan to obtain projection data to reconstruct a 3D volume image according to known techniques (block 5712). Preferably, to simplify registration and/or segmentation, an intra-oral (IO) scan to create a 3D mesh of the dentition (e.g., crowns and gums and invariant landmark such as palatine rugae) is also created during the $T_0$ visit (block 5712), which allows subsequent IO scans at visit $T_n$ to be registered with $T_0$ IO scan in the condition that the $T_0$ IO scan is already registered with $T_0$ CSBT scan, which is simplier to accomplish. The 3D volume image can then be segmented into individual bones and teeth or individual bones and teeth including crowns and roots (block 5714). The segmented 3D volume including at least one identified dental invariant landmark can be input to the biometrics analysis engine 3906 (block 5716). Determination of the dental invariant landmark can be based on methods such as anatomical (e.g., palatine rugae), surgical (e.g., micro implants), imaging (e.g., 2D or 3D Optical Coherence Tomography (OCT) such as blood vasculature imaging on gums or bone foramens), using ultrasound, opto-acoustics or x-ray, etc. According to exemplary method and/or apparatus embodiments for 3-D cephalometric analysis of dental/maxillofacial structure are used to generate a patient specific final virtual CT volume including a desired or final dental/maxillofacial arrangement including segmented teeth that addresses or is in balance with the dental/maxillofacial structure.

As shown in FIG. 57, biometrics analysis engine 3906 can position an label a chosen set of cephalometric parameters in the Segmented $T_0$ CBCT by computation using the dimensions of the reconstructed 3-D image itself and later known information about anatomical features. Then, the biometrics analysis engine 3906 can use the Segmented To CBCT to perform a dental/maxillofacial analysis (block 5720) to generate a To measurement analysis such as a dental/maxillofacial abnormalities summary or report 4600 (block 5730), which can be used by an orthodontic dentist for practitioner treatment planning (block 5735) for treating the patient.

Alternatively, the biometrics analysis engine 3906 can use the Segmented $T_0$ CBCT to perform a dental/maxillofacial analysis and then generate a $T_{end}$ virtual CBCT that corrects at least one dental/maxillofacial abnormalities. Preferably, the biometrics analysis engine 3906 performs a dental/maxillofacial analysis (block 5740) that corrects most dental/maxillofacial abnormalities based on a set of dental orthodontic rules (e.g., tooth movement rules, tooth rotation rules, safety rules, etc. or practitioner treatment planning/diagnosis) to generate the $T_{end}$ virtual CBCT (block 5750). In one embodiment, the biometrics analysis engine 3906 performs a dental/maxillofacial analysis (block 5740) that corrects all dental/maxillofacial abnormalities (block 5720) to harmonized as best as possible the segmented teeth within the dental/maxillofacial structure to generate the $T_{end}$ virtual CBCT (block 5750). This "corrective" dental/maxillofacial analysis by the biometrics analysis engine 3906 can be called operating the biometrics analysis engine 3906 in an inverse fashion or an inverse dental/maxillofacial analysis. It should be noted that the practitioner treatment planning/ diagnosis, the dental orthodontic rules can include surgery, for example, for removal of one or more teeth (before or after eruption), for tooth shaving to reduce volume or shape at least one tooth, or to modify or expand a dental arch before or during (e.g., stage $T_n$) the treatment. Optionally, as shown in FIG. 57, practitioner treatment planning (block 5735) can be used to modify/finalize the $T_{end}$ virtual CBCT.

According to certain exemplary embodiments of the application, the a patient's teeth are repositioned (e.g., incrementally) from an initial tooth arrangement in the Segmented $T_0$ CBCT to a final tooth arrangement in the final virtual CT volume by placing a series of aligners (e.g., dental appliances) in the patient's mouth. Conventionally, the aligners can be fixed to the teeth and a plurality of visits at times ($T_0$, $T_1$, . . . $T_n$, $T_{n+1}$, . . . , $T_{end}$) to the dental practitioner are used to repeatedly validate a current tooth arrangement/positions and/or install a new or updated aligners. Also conventionally, certain aligners are not affixed and the patient may place and replace an aligner in a series of aligners at any time ($T_0$, $T_1$, . . . $T_n$, $T_{n+1}$, $T_{end}$) during the procedure (e.g., with or without a visit to the dental practitioner). Further, a combination of such exemplary type of aligners can be used (e.g., braces and removable elastic devices or retainers).

Generally, a first aligner of the series of incremental dentition adjustment aligners will have a geometry selected to reposition the teeth from the initial tooth arrangement to a first intermediate arrangement. After the first intermediate arrangement is approached or achieved, one or more additional (intermediate) aligners can be successively placed on the teeth, where such additional aligners have geometries/applied force configurations (e.g., elastic) selected to progressively reposition teeth from the first intermediate arrangement through successive intermediate arrangement(s). For example, a plurality of intermediate arrangements can be produced by determining positional differences between a first $T_{initial}$ virtual setup and the $T_{end}$ virtual setup and interpolating said differences (e.g., between 2 to more the 50 stages), linear or non-linear interpolation, between selected I-frames, or the like. An orthodontic or other dental treatment plan can be completed by placing a final aligner in the patient's mouth, where the final aligner has a configurations selected to progressively reposition teeth from the last intermediate arrangement to the final tooth arrangement set by the $T_{end}$ virtual setup (block 5755).

Thus, as shown in FIG. 57, a $T_{end}$ virtual setup (block 5755) can be used to plan or model one or more aligners to move the patient's teeth toward a final tooth arrangement. Thus, in one exemplary embodiment a complete set of progressive clear removable aligners can be generated at block 5755.

Alternatively, in another exemplary embodiment, a dental practitioner can repeatedly produce one or more aligners of a series of incremental aligners to move from an initial tooth arrangement (e.g., incrementally) at least the patient's teeth toward an arrangement in the final virtual CT volume that results from reducing asymmetry and disharmony in dental/maxillofacial structure. In this case as shown in FIG. 57, with the $T_0$ Segmented CBCT and the final virtual CT volume or $T_{end}$ segmented virtual CBCT, a first or initial $T_1$ aligner can be conventionally designed (block 5762), preferably at the $T_0$ visit. Optionally, a safety guard analysis can be performed again by the biometrics analysis engine 3906 using an evaluation of tooth movement from the $T_0$ to $T_1$ (e.g., $T_n$ to $T_{n+1}$ incremental dentition position adjustment) against the selected set of dental orthodontic rules (block 5760). For example, safety guard analysis can include fenestration risk, root collision risk, stage and cumulative tooth movement risk in six degrees of freedom and the like. Block 5760 can also depend on a specific type of aligner used because different types of aligners can apply correspondingly different types, magnitudes and/or even directions and the like of force/tooth movement. In this case, control can jump from $T_0$ visit back to a $T_n$ visit, as shown in FIG. 57 (block 5770)

Again, in one exemplary embodiment, a Segmented $T_n$ CBCT is obtained during a subsequent $T_n$ visit by the patient to the dental practitioner (block 5770). Preferably, during the $T_n$ visit, a dental intra-oral imaging apparatus (e.g., IO scanner) can acquire a 3D mesh of the crowns of the teeth and gums (e.g., upper jaw and lower jaw) and invariant landmark according to known techniques (block 5772). The 3D mesh can then be segmented into individual crowns and gums and then registered to a previous or the Segmented $T_0$ CBCT preferably using the invariant landmark to form a Segmented Tn virtual CBCT (block 5774). The segmented $T_n$ virtual CBCT including the at least one identified dental invariant landmark can be input to the biometrics analysis engine 3906 (block 5776). In one exemplary embodiment, an additional x-ray CBCT scan by a dental extra-oral x-ray CBCT imaging apparatus can be used to reconstruct a $T_n$ 3D volume image according to known techniques (block 5772), which can be registered to a previous or the Segmented $T_0$ CBCT. After registration, the $T_n$ 3D volume image can be segmented.

Alternative scanning and scanning devices for the $T_n$ visit include a depth-resolved volume imaging for obtaining signals that characterize the surfaces of teeth, gum tissue, and other intraoral features. Depth-resolved imaging techniques are capable of mapping surfaces as well as subsurface structures up to a certain depth. Although described using an intra-oral scanner/camera to obtain a dentition surface 3D mesh (e.g., teeth and gums and invariant landmark such as palatine rugae) at each treatment stage (e.g., $T_0$, . . . , $T_n$, . . . , $T_{end}$), exemplary method and/or apparatus embodiments herein can also be implemented using depth-resolved volume imaging techniques such as optical coherence tomography imaging systems, photo-acoustic imaging systems or ultrasound imaging systems. In one exemplary embodiment, depth-resolved volume imaging can image through soft tissue to detect invariant landmarks not detectable by an IO scanner.

Preferably, the biometrics analysis engine 3906 performs a dental/maxillofacial analysis (block 5780) to generate a $T_n$ Treatment progression analysis or report (block 5782), which can be used by the dental practitioner to compare to expected intermediate tooth arrangement (or $T_n$ virtual CBCT) for this particular time period and visit, and then, if desired or needed, an update to the treatment planning can be made (block 5785). Further, the biometrics analysis engine 3906 can use the Segmented $T_n$ CBCT to generate the $T_{n+1}$ virtual CBCT that incrementally corrects selected dental/maxillofacial abnormalities progressively on track to the final tooth arrangement in the final virtual CT volume (block 5740). The $T_{n+1}$ virtual CBCT can be stored, displayed or transmitted remotely (block 5790). Again, a safety guard analysis can be performed by the biometrics analysis engine 3906 (block 5760), and the $T_{n+1}$ virtual CBCT can be used to conventionally generate the $T_{n+1}$ aligner (block 5762). Such aligners can be produced by proprietary factories, printed, molded, prepared at the practitioner's office/chairside, ordered from labs, or the like. As shown in FIG. 57, blocks 5770 (e.g., 5772, 5774, 5776), 5775, 5780, 5740, 5790, 5780, 5782, 5740, 5760, 5762 can be repeated until (i)

treatment is completed, (ii) a determination at block 5782 is positive, and/or (iii) a dental/maxillofacial structure has achieved prescribed orthodontic goals.

Thus, in an exemplary $T_n$ visit, a 3D mesh can be acquired, a segmented $T_n$ virtual CBCT can be determined, and then a determination of fixed and derived cephalometric parameters (e.g., chin, ear bones, forehead, etc.) and measurements of segmented teeth relative position to same can allow situational assessment analysis from teeth and bones to class and distances or situational treatment analysis from class and distance analysis to teeth and bone target position, and generating orthodontic aligners to effectuate the same.

Based on measurement of relative positions of crowns, roots and bones (e.g., dental/maxillofacial structure), exemplary method and/or apparatus embodiments for 3-D cephalometric analysis can use maxillofacial biometrics analysis algorithms (MFBA) to provide and/or determine measurements (e.g., features or derived cephalometric parameters) and provide analysis of the initial patient specific orthodontic and maxillofacial configuration using dental/maxillofacial population data and an invariant landmark to produce a final virtual CT volume including a final tooth arrangement, preferably corresponding to a treatment plan having reduced dental/maxillofacial asymmetry. In one exemplary embodiment, the MFBA can determine treatment (e.g., for initial tooth arrangement) applicability (e.g., indication/viability of successful outcome) to various type of aligners (e.g., wire braces or progressive clear removable aligners). In one embodiment, MFBA can be a maxillofacial artificial intelligence engine for biometric analysis such as biometrics analysis engine 3906. In certain exemplary method and/or apparatus embodiments, MFBA can be used to reposition or move crowns and roots within relative to bones in the skull to reduce dental/maxillofacial asymmetry and/or to reach prescribed orthodontic goals (e.g., dental/maxillofacial balance, class, margins, etc.).

Figure 56:
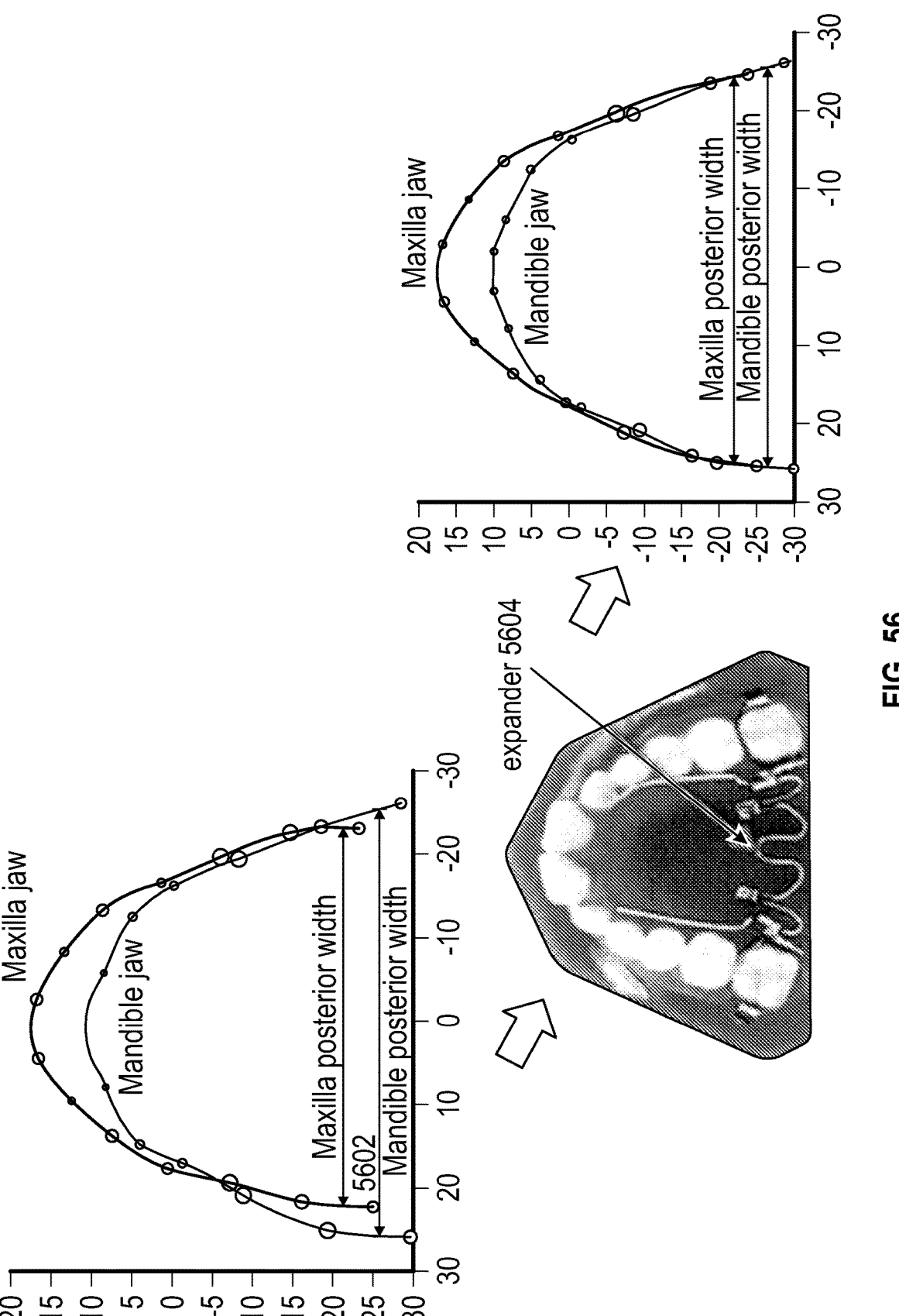
FIG. 56 shows an underlying patient specific aligner to correct a maxillofacial/dental abnormality.

In one example as shown in FIG. 56, the MFBA, receiving a first set of dental/maxillofacial quantitative data (biometry) such as an initial 3D reconstruction of a patient's head, can produce a cephalometric analysis of the condition (e.g., diagnosis) of the dental/maxillofacial structure such as a plurality of descriptive statements (e.g., biometry analysis report 4600) describing a plurality of dental/maxillofacial abnormalities. Then, the MFBA, performing in a reverse or inverse operation, can receive an input of the dental/maxillofacial abnormalities such as the biometry analysis report 4600 and can produce a second set of quantitative dental/maxillofacial data that are used for the development of a plurality of corrective devices such as aligners that in turn mitigate the input plurality of dental/maxillofacial abnormalities. Alternatively, the second set of quantitative dental/maxillofacial data can be used for the development of a corrected (or abnormality reduced) virtual CT volume that can be used for the development of the plurality of corrective devices such as aligners that in turn mitigate the input plurality of dental/maxillofacial abnormalities. As known to one skilled in the art, various aligner types can apply different type of force, e.g., to the teeth, and thus, different types of aligners can address different types of dental/maxillofacial abnormalities.

As shown in FIG. 56, "maxilla basic posterior deficit" evidenced by the graphs 5602 is an exemplary descriptive statement produce by the MFBA to describe the dentition abnormality based on the quantitative (biometry) data "maxilla posterior width" and "mandible posterior width". Said descriptive statement "maxilla basic posterior deficit", input to the MFBA operating in an inverse manner, causes the MFBA to use the relevant quantitative data "maxilla posterior width" and "mandible posterior width", which results in the output of corrective quantitative data that are used to design the corrective aligner, namely a denture expander 5604. Then, at a subsequent visit or treatment stage $T_n$, the patient can be examined using an intraoral scanner, which results in the graphs 5606 that can be compared to a final virtual CT volume.

Conventional orthodontic treatment planning generally "over corrects" the final or target tooth arrangement, namely, moves individual teeth beyond the tooth arrangement that has been selected as the "final" tooth arrangement. Such over correction may be desirable in order to offset potential relapse after the repositioning method has been terminated, e.g., to permit some movement of individual teeth back toward their pre-corrected positions. By coordinating orthodontic treatment planning with maxillofacial/dental structure, certain exemplary method and/or apparatus embodiments herein can provide more stable or harmonized (e.g., reduced maxillofacial/dental asymmetry and/or disharmony) final tooth arrangements that have reduced or eliminated "over correction".

One exemplary method embodiment for producing an intermediate virtual CT Volume ($CT_n$) can include obtaining an initial CT volume of a patient, whose acquisition is done at a first treatment stage $T_0$, the initial CT volume ($CT_0$) including maxilla bone and mandible bone, and crowns and roots for a plurality of teeth; determining at least one invariant landmark within the initial CT volume ($CT_0$) segmenting crowns, roots and bones out of the initial CT volume ($CT_0$)to produce an initial segmented CT volume ($SCT_0$); obtaining an intermediate intraoral digital-impression mesh of a patient ($Scan_n$), whose acquisition is done at a second treatment stage $T_n$ posterior to $T_0$, the intermediate mesh including soft tissue and crowns; segmenting crowns and soft tissues out of the intermediate intraoral digital-impression mesh to produce an intermediate segmented mesh; re-arranging the segmented crowns, roots and bones according to the segmented intermediate mesh to produce an intermediate segmented virtual CT volume ($SCT_n$), said rearrangement being done using the at least one invariant landmark; and displaying, storing or transmitting the intermediate virtual CT Volume ($CT_n$).

One exemplary method embodiment for providing a virtual set-up or an intermediate model, can include receiving a CT volume of a patient corresponding to a treatment stage Tn and at least one invariant landmark; receiving an intraoral digital impression mesh of a patient; receiving segmented soft tissues from the intraoral digital-impression mesh, the segmented soft tissues registered according to the invariant landmark; and producing the virtual set-up or the intermediate model from the CT volume corresponding to the treatment stage Tn and the registered segmented soft tissues. In one embodiment, the at least one invariant landmark is anatomical such as vascular network chin foreman, greater palatine foramina, or incisive foreman; or surgical such as stent or implant. In one embodiment, the at least one invariant landmark is visible on the CT volume and on an intraoral digital-impression mesh. In one embodiment, the at least one invariant landmark is not visible on the intraoral digital-impression mesh, and wherein the method further comprises imaging the invariant landmark and at least a portion of the surface of the mesh using a penetrating imaging scanner such as a OCT, ultrasound, or opto-acoustic scanners.

Consistent with exemplary embodiments herein, a computer program can use stored instructions that perform 3D biometric analysis on image data that is accessed from an electronic memory. As can be appreciated by those skilled in the image processing arts, a computer program for operating the imaging system and probe and acquiring image data in exemplary embodiments of the application can be utilized by a suitable, general-purpose computer system operating as control logic processors as described herein, such as a personal computer or workstation. However, many other types of computer systems can be used to execute the computer program of the present invention, including an arrangement of networked processors, for example. The computer program for performing exemplary method embodiments may be stored in a computer readable storage medium. This medium may include, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary method embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products of the application may make use of various image manipulation algorithms and processes that are well known. Additional aspects of such algorithms and systems, and hardware and/or software for producing and otherwise processing the images or co-operating with the computer program product exemplary embodiments of the application, are not specifically shown or described herein and may be selected from such algorithms, systems, hardware, components and elements known in the art.

Certain exemplary method and/or apparatus embodiments according to the application can allow the practitioner to take advantage of objective metrics and/or displayed data to help evaluate asymmetric facial/dental anatomic structure(s). Advantageously, exemplary method and/or apparatus embodiments can provide multiple graduated or heirarchical measured and analyzed results displayed in successively higher order formats suitable for assessment by the practitioner. Although embodiments of the present disclosure are illustrated using dental imaging apparatus, similar principles can be applied for other types of diagnostic imaging and for other anatomy. Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

The invention claimed is:

1. A method for 3D cephalometric analysis of a patient, the method executed at least in part on a computer processor and comprising the steps of:

displaying a reconstructed volume image from a computed tomographic scan of a patient's head from at least one 2D view or a 3D view;

displaying at least one reference mark on the displayed at least one 2D view or the 3D view;

segmenting one or more dentition elements within the reconstructed volume image;

computing and displaying a plurality of cephalometric parameters for the patient's head according to data from the at least one reference mark and the one or more segmented dentition elements;

computing, using the computed cephalometric parameters, one or more results indicative of maxillofacial/dental abnormalities;

converting said one or more computed results into a plurality of diagnostic control signals, each diagnostic control signal indicative of respective asymmetry and disharmony conditions; and composing a patient specific indicative results report through a plurality of composition logic circuits, each composition logic circuit implementing a logic truth table that receives the diagnostic control signals and outputs a composite diagnostic statement, wherein the report comprises a plurality of patient specific composite statements for asymmetry and disharmony.

2. The method of claim 1, wherein composing the patient specific indicative results report comprises constructing a plurality of composition systems each responsible for composing one of the plurality of patient specific composite statements.

3. The method of claim 2, wherein composing the patient specific indicative results report comprises constructing a plurality of composition circuits that are each responsible for composing one of a plurality of patient specific statements that in combination form one of the plurality of patient specific composite statements.

4. The method of claim 1, where the patient specific indicative results report comprises:

a patient identifier;

an asymmetry patient specific description divided into an anterior-posterior composite statement, a vertical composite statement, and a transversal composite statement; and a disharmony patient specific description divided into an anterior-posterior composite statement, a vertical composite statement, and a transversal composite statement.

5. The method of claim 4, where each of the asymmetry patient specific description and the disharmony patient specific description comprises a synthetic composite statement.

6. The method of claim 3, where the plurality of patient specific composite statements includes an asymmetry anterior-posterior composite statement, an asymmetry vertical composite statement, an asymmetry transversal composite statement, a disharmony anterior-posterior composite statement, a disharmony vertical composite statement, and a disharmony transversal composite statement.

7. The method of claim 3, where each of the plurality of patient specific statements comprises one or more selectable comments, and wherein the method further comprises the step of:

designating and storing, using the underlying computed cephalometric parameters, at least one graphical view for each of the one or more selectable comments, where the at least one graphical view includes at least 2 orthogonal graphical views or a 3D graphical view.

8. The method of claim 3, further comprising designating and storing, using the underlying computed cephalometric parameters, at least one graphical view for each of the one or more selectable patient specific statements and each of the plurality of patient specific composite statements.

9. The method of claim 8, further comprising the step of receiving and storing an operator modification of one of the at least one graphical views for one of the one or more selectable patient specific statements and one of the plurality of composite statements.

10. The method of claim 1, where computing and displaying a plurality of cephalometric parameters comprises generating a three-dimensional framework related to the computed cephalometric parameters.

11. The method of claim 1, where computing one or more results indicative of maxillofacial/dental abnormalities comprises evaluating one or more of the computed cephalometric parameters against a value calculated from a sampling of a patient population.

12. An apparatus, comprising:

a biometrics analysis engine configured to access:

(i) patient specific biometry data including segmented dentition elements and at least one reference mark within a reconstructed volume image; and (ii) population biometry data including, for each patient amongst a population of multiple patients, segmented dentition elements and a landmark within a reconstructed volume image, where the biometrics analysis engine comprises:

(i) an asymmetry analysis system that performs calculations and generates at least first diagnostic control signals; and (ii) a disharmony analysis system that performs calculations and generates at least second diagnostic control signals; and

composition logic comprising a plurality of composition logic circuits, each composition logic circuit implementing a logic truth table that receives the first diagnostic control signals and the second diagnostic control signals from the biometrics analysis engine, where the composition logic outputs descriptive statements organized into a 3D patient specific analysis report identifying one or more dental/maxillofacial abnormalities, where the 3D patient specific analysis report comprises:

a patient identifier;

an asymmetry patient specific description divided into one or more of an anterior-posterior composite statement, a vertical composite statement, and a transversal composite statement; and a disharmony patient specific description divided into one or more of an anterior-posterior composite statement, a vertical composite statement, and a transversal composite statement, wherein each composite statement is generated by a corresponding composition logic circuit of the plurality of composition logic circuits responsive to the diagnostic control signals.

\* \* \* \* \*